US012716074B1

(12) United States Patent
Mustafa et al.

(10) Patent No.: US 12,716,074 B1
(45) Date of Patent: Aug. 25, 2026

(54) RECOMBINANT RETROVIRAL VECTORS FOR GENE THERAPY

(71) Applicant: United Arab Emirates University, Al Ain (AE)

(72) Inventors: Farah Mustafa, Al Ain (AE); Tahir A. Rizvi, Al Ain (AE); Shaima Akhlaq, Al Ain (AE); Soumeya Jaballah, Al Ain (AE); Waqar Ahmad, Al Ain (AE)

(73) Assignee: United Arab Emirates University, Al Ain (AE)

( * ) Notice: Subject to any disclaimer, the term of this patent is extended or adjusted under 35 U.S.C. 154(b) by 0 days.

(21) Appl. No.: 19/277,352

(22) Filed: Jul. 22, 2025

(51) Int. Cl.
*C12N 15/86* (2006.01)

(52) U.S. Cl.
CPC .... *C12N 15/86* (2013.01); *C12N 2740/12022* (2013.01); *C12N 2740/12043* (2013.01); *C12N 2740/12045* (2013.01)

(58) Field of Classification Search
CPC .......... C12N 15/86; C12N 2740/12022; C12N 2740/12043; C12N 2740/12045
See application file for complete search history.

(56) References Cited

U.S. PATENT DOCUMENTS

| | | | |
|---|---|---|---|
| 6,808,922 | B1 | 10/2004 | Bebbington et al. |
| 6,824,770 | B1 | 11/2004 | Falck-Pedersen |
| 7,074,398 | B1 | 7/2006 | Gunzburg et al. |
| 2002/0061297 | A1 | 5/2002 | Gunzburg et al. |
| 2016/0333373 | A1 | 11/2016 | Farley et al. |
| 2024/0052366 | A1 | 2/2024 | Farley et al. |

FOREIGN PATENT DOCUMENTS

| | | | |
|---|---|---|---|
| EP | 2589661 | A1 | 5/2013 |
| WO | 2000056910 | A1 | 9/2000 |
| WO | WO 0056910 | A1 | 9/2000 |

OTHER PUBLICATIONS

Konstantoulas CJ and Indik S. Mouse mammary tumor virus-based vector transduces non-dividing cells, enters the nucleus via a TNPO3-independent pathway and integrates in a less biased fashion than other retroviruses. Retrovirology. Apr. 30, 2014;11:34. doi: 10.1186/1742-4690-11-34. PMID: 24779422) (Year: 2014).*

Throm RE. et al. Efficient construction of producer cell lines for a SIN lentiviral vector for SCID-X1 gene therapy by concatemeric array transfection. Blood. May 21, 2009;113(21):5104-10. doi: 10.1182/blood-2008-11-191049. Epub Mar. 13, 2009. PMID: 19286997; PMCID: PMC2686181 (Year: 2009).*

Zufferey R. et al. Self-inactivating lentivirus vector for safe and efficient in vivo gene delivery. J Virol. Dec. 1998;72(12):9873-80. doi: 10.1128/JVI.72.12.9873-9880.1998. PMID: 9811723; PMCID: PMC110499 (Year: 1998).*

Rizvi et al. "Role of a heterologous retroviral transport element in the development of genetic complementation assay for mouse mammary tumor virus (MMTV) replication," Virology 385 (2009) pp. 464-472.

Farah Mustafa et al., 'The bifurcated stem loop 4 (SL4) is crucial for efficient packaging of mouse mammary tumor virus (MMTV) genomic RNA', RNA Biology, 2018, vol. 15, No. 8, pp. 1047-1059.

Office Action Summary issued on Apr. 28, 2026 in related application No. UAE P2025-02440.

Said I. Ismail et al., 'Split-intron retroviral vectors: enhanced expression with improved safety', Journal of Virology, Mar. 2000, vol. 74, No. 5, pp. 2365-2371.

Search Report issued on Apr. 28, 2026 in related application No. UAE P2025-02440.

Stanislav Indik, 'Mouse mammary tumor virus-based vector for efficient & safe transgene delivery into mitotic & non-mitotic cells', Cell and Gene Therapy Insights, Dec. 1, 2016, vol. 2, No. 5, pp. 589-598.

Substantive Examination Result issued on Apr. 28, 2026 in related application No. UAE P2025-02440.

* cited by examiner

*Primary Examiner* — Tracy Vivlemore
*Assistant Examiner* — Vyoma Shubham Tiwari
(74) *Attorney, Agent, or Firm* — KNOBBE, MARTENS, OLSON & BEAR, LLP

(57) ABSTRACT

The present invention relates to Split-Intron Final Self-Inactivating (SIN) retroviral vectors which comprises a viral major splice donor (mSD) comprising mutations, a mouse mammary tumor vector long terminal repeat (MMTV-LTR) or a Type B leukemogenic virus long terminal repeat (TBLV-LTR), a eukaryotic splice acceptor (eSA), and a eukaryotic splice donor (eSD). Furthermore, the invention relation to the use and methods of uses of such vectors in gene therapy.

10 Claims, 11 Drawing Sheets
(11 of 11 Drawing Sheet(s) Filed in Color)

Specification includes a Sequence Listing.

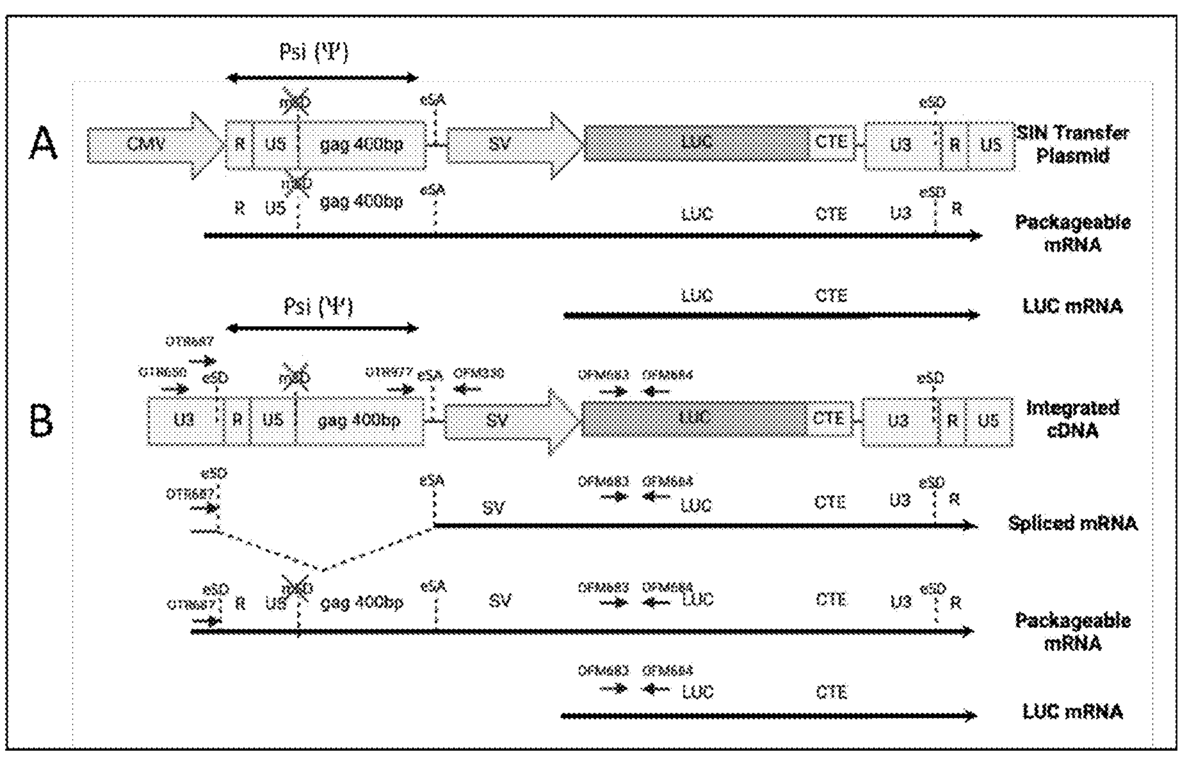

Figure 3

WT mSD Sequence:
GCCUACGGAGAAGAGGUAGGUUACGGU
GAGCCAUUGGAAAUG mSD1 Mutation:
GCCUGGGGAGAAGACCUAGGUUACGGU
GAGCCAUUGGAAAUG
Result: Good. First three of the 13 structures like wild type SL4.

mSD2 Mutation:
GCCAGGGGAGAAGAaCCUGGUUACGGUG
AGCCAUUGGAAAUG
Result: Best mutant. Seven of 9 structures with wild type SL4 (structure #1, 2, 3, 5, 7, 8, 9).

Bifurcated SL4

Gag AUG mSD

Pal II ssPurines

Figure 4

SEQUENCE LISTING

```
Sequence total quantity: 28
SEQ ID NO: 1            moltype = DNA  length = 42
FEATURE                 Location/Qualifiers
source                  1..42
                        mol_type = genomic DNA
                        organism = Mus musculus
SEQUENCE: 1
gcctacggag aagaggtagg ttacggtgag ccattggaaa tg                    42

SEQ ID NO: 2            moltype = DNA  length = 42
FEATURE                 Location/Qualifiers
source                  1..42
                        mol_type = other DNA
                        organism = synthetic construct
SEQUENCE: 2
gcctggggag aagacctagg ttacggtgag ccattggaaa tg                    42

SEQ ID NO: 3            moltype = DNA  length = 42
FEATURE                 Location/Qualifiers
source                  1..42
                        mol_type = other DNA
                        organism = synthetic construct
SEQUENCE: 3
gccaggggag aagaacctgg ttacggtgag ccattggaaa tg                    42

SEQ ID NO: 4            moltype = DNA  length = 101
FEATURE                 Location/Qualifiers
source                  1..101
                        mol_type = other DNA
                        organism = synthetic construct
SEQUENCE: 4
aactgtgctt gtcgagacag agaagactct tgcgtttctg ataggcacct attggtctta 60
ctgacatcca ctttgccttt ctctccacag gtgtccactc c                     101

SEQ ID NO: 5            moltype = DNA  length = 46
FEATURE                 Location/Qualifiers
source                  1..46
                        mol_type = other DNA
                        organism = synthetic construct
SEQUENCE: 5
cgttaacact agtaagcttg ctctaaggta aatagtcgac aggcct                46
```

```
SEQ ID NO: 6            moltype = DNA  length = 1287
FEATURE                 Location/Qualifiers
source                  1..1287
                        mol_type = genomic DNA
                        organism = Mus musculus
SEQUENCE: 6
cctaggggag aagcagccaa ggggttgttt cccaccaagg acgacccgtc tgcgcacaaa  60
cggatgagcc catcagacaa agacatattc attctctgct gcaaacttgg catagctctg  120
ctttgctggg ggccattggg ggaagttgcg gttcgtgctc gcagggctct caccccttgac  180
tcttttaata gctcttctgt gcaagattac aatctaaaca attcggagaa ctcgaccttc  240
ctcctgaggc aaggaccaca gccaacttcc tcttacaagc cgcatcgatt ttgtccttca  300
gaaatagaaa taagaatgct tgctaaaaat tatattttta ccaataagac caatccaata  360
ggtagattat tagttactat gttaagaaat gaatcattat cttttagtac tatttttact  420
caaattcaga agttagaaat gggaatagaa aatagaaaga gacgctcaac ctcaattgaa  480
gaacaggtgc aaggactatt gaccacaggc ctagaagtaa aaaagggaaa aaagagtgtt  540
tttgtcaaaa taggagacag gtggtggcaa ccagggactt ataggggacc ttacatctac  600
agaccaacag atgccccctt accatataca ggaagatatg acttaaattg ggataggtgg  660
gttacagtca atggctataa agtgttatat agatccctcc cttttcgtga aagactcgcc  720
agagctagac ctccttggtg tatgttgtct caagaagaaa aagacgacat gaaacaacag  780
gtacatgatt atatttatct aggaacagga atgcactttt ggggaaagat tttccatacc  840
aaggagggga cagtggctgg actaatagaa cattattctg caaaaactta tggcatgagt  900
tattatgaat agcctttatt ggcccaacct tgcggttccc aaggcttaag taagtttttg  960
gttacaaact gttcttaaaa cgaggatgtg agacaagtgg tttcctgact tggtttggta  1020
tcaaaggttc tgatctgagc tctgagtgtt ctattttcct atgttctttt ggaatttatc  1080
caaatcttat gtaaatgctt atgtaaacca agatataaaa gagtgctgat tttttgagta  1140
aacttgcaac agtcctaaca ttcacctctt gtgtgtttgt gtctgttcgc catcccgtct  1200
ccgctcgtca cttatccttc actttccaga gggtcccccc gcagaccccg gcgaccctca  1260
ggtcggccga ctgcggcagc ggtaccc                                      1287

SEQ ID NO: 7            moltype = DNA  length = 967
FEATURE                 Location/Qualifiers
source                  1..967
                        mol_type = genomic DNA
                        organism = Mus musculus
SEQUENCE: 7
cctaggggag aagcagccaa ggggttgttt cccaccaagg acgacccgtc tgcgcacaaa  60
cggatgagcc catcagacaa agacatattc attctctgct gcaaacttgg catagctctg  120
ctttgcctgg ggctattggg ggaagttgcg gttcgtgctc gcagggctct caccccttgac  180
tcttttaata gctcttctgt gcaagattac aatctaaaca attcggagaa ctcgaccttc  240
ctcctgaggc aaggaccaca gccaacttcc tcttacaagc cgcatcgatt ttgtccttca  300
gaaatagaga taagaatgct tgctaaaaaa tatattttta ccaataagac caatccaata  360
ggtagactat tagtcactat gttaagaaat gaatcattat cttttagtac tatttttact  420
caaattcaga agttaaaatg gaaatagaaa atagaaagag acgctcaacc tcagttgaag  480
aacaggtgcg gttcccaagg cttaagtagg tttatggtta caaactgttc ttacagttga  540
agaacaggtg cggttcccaa ggcttaagta ggtttatggt tacaaactgt tcttacagtt  600
gaagaacagg tgcggttccc aaggcttaag taagtttatg gttacaaact gttcttaaaa  660
caaggatgtg agacaagtgg tttcctgagt tggtttggta tcaaatgttc tgatctgagc  720
tctgagtgtt ctattttcct atgttctttt ggaatttatc caaatcttat gtaaatgctt  780
atgtaaacca agatataaaa gagtgctgat tttttgagta aacttgcaac agtcctaaca  840
ttcacctctt gtgtgtttgt gtctgttcgc catcccgtct ccgctcgtca cttatccttc  900
actttccaga gggtcccccc gcagaccccg gcgaccctca ggtcggccga ctgcggcagc  960
ggtaccc                                                             967

SEQ ID NO: 8            moltype = DNA  length = 237
FEATURE                 Location/Qualifiers
source                  1..237
                        mol_type = genomic DNA
                        organism = Betaretrovirus maspfimon
SEQUENCE: 8
tgtgagctag actggacagc caatgacggg taagagagtg acatttctca ctaacctaag  60
acaggagggc cgtcaaagct actgcctaat ccaatgacgg gtaatagtga caagaaatgt  120
atcactccaa cctaagacag gcgcagcctc cgagggatgt gtcttttgtt ttttataatt  180
aaaaagggtg acatgtccgg agccgtgctg cccggatgat gtcttggatc cggctag     237

SEQ ID NO: 9            moltype =   length =
SEQUENCE: 9
000

SEQ ID NO: 10           moltype = DNA  length = 5507
FEATURE                 Location/Qualifiers
source                  1..5507
                        mol_type = other DNA
                        organism = synthetic construct
SEQUENCE: 10
gccgccacca tgggtgtttc tgggtcaaag ggccaaaaac tttttgtcag cgtactgcag  60
cgactcttgt ccgagcgagg gcttcacgta aaagaaagct cagcgattga attctatcag  120
ttcctcataa aagtttcccc ctggttcccg gaggagggag ggctgaatct tcaagactgg  180
aaacgagtcg gtcgggagat gaaacgatac gcagccgagc atggaactga tagcataccc  240
```

-continued

```
aaacaagcat accctatttg gttgcaactg cgggagatac ttacagagca gagtgacctg  300
gttctcctca gcgctgaggc caaatccgtc accgaagaag agctcgagga gggtttgacc  360
ggcctgctgt caacttcttc ccaggagaaa acatatggta cgaggggcac agcttacgcc  420
gagattgaca ccgaggttga caaactcagt gagcacattt atgatgaacc ctacgaagaa  480
aaagaaaagg ctgataagaa tgaggaaaag gaccatgtaa ggaaagttaa aaaaatagta  540
cagcgcaaag agatatccga gggcaaacga aaagaaaaag accagaaagc ctttctggca  600
acggactgga acgatgacga cctgagccct gaagactggg atgacctgga ggagcaagca  660
gcccattacc acgacgacga tgaactgatc ctcccggtaa agagaaaggt agttaagaag  720
aaacctcagg cactgcgccg aaagccgctg ccaccggtcg gatttgccgg cgcaatggct  780
gaggcgagag aaaagggtga ccttactttc acattcccgg tggtatttat gggggaatct  840
gacgatgatg acactcctgt ctgggagccc ctgcctctca agacccttaa ggagttgcag  900
ctcgccgtta agactatggg cccttctgcg ccttatactt tgcaagtagt ggacatggtt  960
gcaagccagt ggctcacccc gagtgactgg caccaaacgg cgagagctac cctctcccca  1020
ggagactatg ttttgtggcg gacggagtac gaagagaaaa gtaaggagac tgtacagaaa  1080
gccgctggaa agaggaaagg gaaagtctct ttggatatgt tgctcggaac aggtcaattt  1140
ttgagcccat catctcagat aaagctcagc aaagacgtgt tgaaggacgt aacaaccaac  1200
gcggttctcg catggcgcgc aatcccaccc ccaggtgtga agaagacggt tttggcgggc  1260
cttaaacagg gaaatgaaga atcctacgag actttcatat cacgacttga agaggccgta  1320
tatcgcatga tgcctcgcgg tgaaggatct gacatcctca tcaagcagct ggcgtgggaa  1380
aacgctaatt ccctctgtca ggacttgatt aggccaatta gaaagaccgg caccatccag  1440
gattatatac gagcgtgctt ggatgcatct ccagcagtcg tgcaaggaat ggcctacgcg  1500
gcagcaatgc gaggccaaaa atactcaacc ttcgtgaaac aaacatacgg aggtgggaaa  1560
ggtgggcaag gttcagaagg acccgtttgc ttcagctgtg gaaaaacggg gcatataaaa  1620
aaagattgca aggaggagaa agggagtaag cgagcccctt ccggtctgtg tcctaggtgt  1680
aaaaaagggt atcactggaa gtcagagtgc aaatctaagt ttgacaagga cggaaatcct  1740
cttccacccc tggagaccaa tactgaaaat tcaaaaaact tgtaaagggc cagagcccgt  1800
cacctacaca gaagggagac ggggtaaaag gttccggttt gaatccggaa gcaccaccat  1860
ttactataca cgatttgcct aggggcactc ctgggagtgc gggtcttgac ctttcttcac  1920
aaaaggactt gatcctgtcc cttgaagatg gggtttcttt ggtacccaca ctggtcaaag  1980
gtaccttgcc cgagggcaca acggggctga ttataggcag atcatcaaac tacaagaaag  2040
gattggaagt gctgccgggc gtcatagatt ctgacttcca aggggaaatt aaggttatgg  2100
taaaggccgc aaaaaatgca gttataatcc acaaaggtga aaggatcgca cagcttctgc  2160
ttctgcccta cttgaaactc cccaacccca tcataaaaga ggaacgaggg agtgaaggat  2220
tcgggtctac ttctcatgtt cattgggtcc aggagatttc cgactcaagg cccatgttgc  2280
atatttcctt gaatggaaga cgcttcctcg ggttgcttga tacgggagct gacaagacct  2340
gcatagcagg tcgagactgg ccagccaact ggcctataca tcaaacggag agttcactgc  2400
agggtttggg catggcatgc ggtgtcgcaa ggagttcaca gcctcttcga tggcaacatg  2460
aggataaaag cggtattata cacccgttcg tgattccaac attgcctttc acactgtggg  2520
gccgggacat tatgaaagaa attaaagtga gacttatgac cgacagtcct gatgattcac  2580
aggatttatg ataggcgcca tagaaagtaa cttgtttgcc gaccagattt cttggaaaag  2640
tgaccaaccg gtctggctta atcaattggc cgctcaaaca agagaagttg caagcgctcc  2700
aacaactcgt cacagaacag cttcagcttg gtcatcttga ggaatccaat tctccatgga  2760
acacaccggt attcgtaata aaaaaaaaat caggtaagtg gaggcttctt caagacttgc  2820
gcgccgtcaa cgctacgatg catgacatgg gggccctgca gcccggcctt ccaagcccag  2880
tggctgtacc aaagggttgg gagataataa ttatagacct tcaggactgt tttttcaaca  2940
tcaaattgca cccggaggat tgcaagagat ttgcctttag tgttcctagc ccgaatttca  3000
agagaccgta tcagcgattc cagtggaaag tgctgcccca aggaatgaaa aattctccaa  3060
cactctgcca aaaattcgtc gacaaggcaa tcctgacggt gcgcgacaag tatcaagact  3120
cctacatcgt ccattatatg gatgatattt tgctcgctca ccccagccga agcatagtag  3180
acgaaatact cacgagcatg atccaggccc tgaataaaca cggactggtc gtaagtacgg  3240
agaaaattca gaagtatgat aatctgaaat accttggcac gcatattcaa ggggacgtag  3300
ttagttacca gaagcttcag atacgaacgg ataaactgcg aactctcaac gatttccaga  3360
agttgctggg gaatatcaat tggatacgac cttttctcaa gctcacaact ggcgaactga  3420
agccgttgtt cgaaatcctt aacggcgaca gtaatcccat ctccatccgc aaactcaccc  3480
ctgaggcctg caaggccttg caattggtga atgagcgact gagcattgcg agagtaaaaa  3540
gactcgattt gagccggcca tggagtctgt gtatattgaa aacggaatat actccaactg  3600
catgcttgtg gcagaacggc gtgctggaat ggattcatct tccccatatt tctcccaaag  3660
ttattacgcc atatgatata ttctgcacac aactcattat caaaggccga cataggtcta  3720
aggaactgtt cagtaaggac ccggattaca ttgtggtccc atacacaaag gtacagttcg  3780
atcttctttt gcaagaaaag gaagattggc cgatttcctt gttgggtttc cttggggagg  3840
tacactttca ccttccaaaa gatcccttgc ttacgtttac gcttcaaacg gctatcatct  3900
ttcctcatat gaccagtacg acgcccctgg agaagggaat agtcattttc actgatggaa  3960
gtgccaatgg aagaagcgtg acatatatcc aggggcgaga gccaattatc aaagagaaca  4020
cgcagaatac ggctcaacag gcagagatcg tggccgttat aacagcgttt gaagaggtaa  4080
gtcagagctt caatctctac accgactcaa agtacgttac tgggcttttc ccagaaattg  4140
aaacagcgac acttagcccc agaaccaaaa tatatacaga gctcaggcat cttcaacgac  4200
tgattcacaa acgacaagag aaattctata ttggccatat aaggggacat actggccttc  4260
ctggaccctt ggcgcaaggc aatgcttacg cggactcact gactaggatc ctgactgcct  4320
tggagagtgc tcaggaaagt catgcacttc atcaccaaaa cgcagcagct ctccgattcc  4380
aatttcatat aacgagagag caagccagag agattgtaaa actgtgccct aattgcccgg  4440
attggggtca tgctcctcaa ctcggagtaa atccgagggg gttgaaacca cgagttctgt  4500
ggcagatgga tgtaacacac gtaagcgagt tcggtaagct gaagtacgta cacgttacag  4560
ttgataccta cagccacttc acattcgcca ctgcacgaac aggagaggcc acaaaagatg  4620
tgttgcagca cttggcccaa agcttcgctt acatgggatt cccacaaaag atcaagactg  4680
acaatgcacc ggcatatgta tcacgcagta tccaagagtt tctcgcgcgg tggaaaatct  4740
ctcatgtgac gggcatcccc tacaatccgc agggtcaagc cattgtggag cgcactcacc  4800
agaatattaa ggctcagctg aataaattgc agaaggctgg aaagtactat acgccacacc  4860
acttgctggc acatgccctt ttcgtactca atcatgtgaa catggacaac caaggacata  4920
ccgctgcaga gcgacactgg ggaccgatca gcgccgatcc taaaccaatg gtaatgtgga  4980
```

```
aagatctttt ggcgggcagc tggaaggggc cggacgtcct gatcaccgcc ggccgaggat  5040
atgcttgcgt tttcccacaa gatgcggaga ctccaatatg ggtgcccgat cgattcatta  5100
gacctttac agagagaaaa gaagctactc caacgccggg gactgccgaa aagactcccc  5160
ctagggacga gaaggaccag cagaagagtc ctgaggatga gtccagccca caccagagag  5220
aggacggact ggcgacgtca gccggagtaa acctcaggag tggaggtgga agttaacccc  5280
tgtgagctag actggacagc caatgacggg taagagagtg acatttctca ctaacctaag  5340
acaggagggc cgtcaaagct actgcctaat ccaatgacgg gtaatagtga caagaaatgt  5400
atcactccaa cctaagacag gcgcagcctc cgagggatgt gtcttttgtt ttttataatt  5460
aaaaagggtg acatgtccgg agccgtgctg cccggatgat gtcttgg              5507

SEQ ID NO: 11          moltype = DNA  length = 1536
FEATURE                Location/Qualifiers
source                 1..1536
                       mol_type = other DNA
                       organism = Indiana vesiculovirus
SEQUENCE: 11
atgaagtgcc ttttgtactt agccttttta ttcattgggg tgaattgcaa gttcaccata  60
gtttttccac acaaccaaaa aggaaactgg aaaaatgttc cttctaatta ccattattgc  120
ccgtcaagct cagatttaaa ttggcataat gacttaatag gcacagcctt acaagtcaaa  180
atgcccaaga gtcacaaggc tattcaagca gacggttgga tgtgtcatgc ttccaaatgg  240
gtcactactt gtgatttccg ctggtatgga ccgaagtata taacacattc catccgatcc  300
ttcactccat ctgtagaaca atgcaaggaa agcattgaac aaacgaaaca aggaacttgg  360
ctgaatccag gcttccctcc tcaaagttgt ggatatgcaa ctgtgacgga tgccgaagca  420
gtgattgtcc aggtgactcc tcaccatgtg ctggttgatg aatacacagg agaatgggtt  480
gattcacagt tcatcaacgg aaaatgcagc aattacatat gccccactgt ccataactct  540
acaacctggc attctgacta taaggtcaaa gggctatgtg attctaacct catttccatg  600
gacatcacct tcttctcaga ggacggagag ctatcatccc tgggaaagga gggcacaggg  660
ttcagaagta actactttgc ttatgaaact ggaggcaagg cctgcaaaat gcaatactgc  720
aagcattggg gagtcagact cccatcaggt gtctggttcg agatggctga taaggatctc  780
tttgctgcag ccagattccc tgaatgccca gaagggtcaa gtatctctgc tccatctcag  840
acctcagtgg atgtaagtct aattcaggac gttgagagga tcttggatta ttccctctgc  900
caagaaacct ggagcaaaat cagagcgggt cttccaatct ctccagtgga tctcagctat  960
cttgctccta aaaacccagg aaccggtcct gctttcacca taatcaatgg taccctaaaa  1020
tactttgaga ccagatacat cagagtcgat attgctgctc caatcctctc aagaatggtc  1080
ggaatgatca gtggaactac cacagaaagg gaactgtggg atgactgggc accatatgaa  1140
gacgtggaaa ttggacccaa tggagttctg aggaccagtt caggatataa gtttccttta  1200
tacatgattg gacatggtat gttggactcc gatcttcatc ttagctcaaa ggctcaggtg  1260
ttcgaacatc ctcacattca agacgctgct tcgcaacttc ctgatgatga gagtttattt  1320
tttggtgata ctgggctatc caaaaatcca atcgagcttg tagaaggttg gttcagtagt  1380
tggaaaagct ctattgcctc ttttttcttt atcatagggt taatcattgg actattcttg  1440
gttctccgag ttggtatcca tctttgcatt aaattaaagc acaccaagaa aagacagatt  1500
tatacagaca tagagatgaa ccgacttgga aagtaa                          1536

SEQ ID NO: 12          moltype = DNA  length = 20
FEATURE                Location/Qualifiers
source                 1..20
                       mol_type = other DNA
                       organism = synthetic construct
SEQUENCE: 12
caattgttcc aggaaccagg                                            20

SEQ ID NO: 13          moltype = DNA  length = 15
FEATURE                Location/Qualifiers
source                 1..15
                       mol_type = other DNA
                       organism = synthetic construct
SEQUENCE: 13
gataccgctc gccgc                                                 15

SEQ ID NO: 14          moltype = DNA  length = 64
FEATURE                Location/Qualifiers
source                 1..64
                       mol_type = other DNA
                       organism = synthetic construct
SEQUENCE: 14
aggcctgtcg actatttacc ttagagcaag cttactagtg ttaacgcact cttttatatc  60
ttgg                                                             64

SEQ ID NO: 15          moltype = DNA  length = 64
FEATURE                Location/Qualifiers
source                 1..64
                       mol_type = other DNA
                       organism = synthetic construct
SEQUENCE: 15
cgttaacact agtaagcttg ctctaaggta aatagtcgac aggcctctga tttttgagt  60
aaac                                                             64

SEQ ID NO: 16          moltype = DNA  length = 39
FEATURE                Location/Qualifiers
```

```
source                  1..39
                        mol_type = other DNA
                        organism = synthetic construct
SEQUENCE: 16
gactatttac cttagagcaa gcactctttt atatcttgg                          39

SEQ ID NO: 17           moltype = DNA  length = 39
FEATURE                 Location/Qualifiers
source                  1..39
                        mol_type = other DNA
                        organism = synthetic construct
SEQUENCE: 17
cttgctctaa ggtaaatagt cctgattttt tgagtaaac                          39

SEQ ID NO: 18           moltype = DNA  length = 18
FEATURE                 Location/Qualifiers
source                  1..18
                        mol_type = other DNA
                        organism = synthetic construct
SEQUENCE: 18
ctcaggtcgg ccgactgc                                                 18

SEQ ID NO: 19           moltype = DNA  length = 23
FEATURE                 Location/Qualifiers
source                  1..23
                        mol_type = other DNA
                        organism = synthetic construct
SEQUENCE: 19
gccccgaatt catgcatatg gtg                                           23

SEQ ID NO: 20           moltype = DNA  length = 67
FEATURE                 Location/Qualifiers
source                  1..67
                        mol_type = other DNA
                        organism = synthetic construct
SEQUENCE: 20
gacgagctgt acaagtaaga agactcttgc gtttctgata ggcacctatt ggtcttactg  60
acatcca                                                             67

SEQ ID NO: 21           moltype = DNA  length = 72
FEATURE                 Location/Qualifiers
source                  1..72
                        mol_type = other DNA
                        organism = synthetic construct
SEQUENCE: 21
gaagactctt gcgtttctga taggcaccta ttggtcttac tgacatccac tttgcctttc  60
tctccacagg tg                                                       72

SEQ ID NO: 22           moltype = DNA  length = 18
FEATURE                 Location/Qualifiers
source                  1..18
                        mol_type = other DNA
                        organism = synthetic construct
SEQUENCE: 22
ggaggcctag gcttttgc                                                 18

SEQ ID NO: 23           moltype = DNA  length = 67
FEATURE                 Location/Qualifiers
source                  1..67
                        mol_type = other DNA
                        organism = synthetic construct
SEQUENCE: 23
cgttaacact agtaagcttg ctctaaggta aatagtcgac aggcctttca cctcttgtgt  60
gtttgtg                                                             67

SEQ ID NO: 24           moltype = DNA  length = 29
FEATURE                 Location/Qualifiers
source                  1..29
                        mol_type = other DNA
                        organism = synthetic construct
SEQUENCE: 24
cagggtaccg ctgccgcagt cggccgacc                                     29

SEQ ID NO: 25           moltype = DNA  length = 26
FEATURE                 Location/Qualifiers
source                  1..26
                        mol_type = other DNA
                        organism = synthetic construct
SEQUENCE: 25
```

-continued

```
ccactagtga gttgggacaa gatgtg                                     26

SEQ ID NO: 26          moltype = DNA  length = 28
FEATURE                Location/Qualifiers
source                 1..28
                       mol_type = other DNA
                       organism = synthetic construct
SEQUENCE: 26
cctctagatg cgaagagcct tgaccaag                                   28

SEQ ID NO: 27          moltype = DNA  length = 28
FEATURE                Location/Qualifiers
source                 1..28
                       mol_type = other DNA
                       organism = synthetic construct
SEQUENCE: 27
cctctagacc aaccttgcgg ttcccaag                                   28

SEQ ID NO: 28          moltype = DNA  length = 28
FEATURE                Location/Qualifiers
source                 1..28
                       mol_type = other DNA
                       organism = synthetic construct
SEQUENCE: 28
gtttaaccgg actactatcg acaagttc                                   28
```

RECOMBINANT RETROVIRAL VECTORS FOR GENE THERAPY

REFERENCE TO SEQUENCE LISTING

The present application is being filed along with a Sequence Listing in electronic format. The Sequence Listing is provided as a file entitled ROUS019.004AUS.xml, which was created and last modified on Sep. 11, 2025, and is 34,735 bytes in size. The information in the electronic Sequence Listing is hereby incorporated by reference in its entirety.

FIELD

The invention relates to novel recombinant retroviral vectors suitable for gene therapy of infections and diseases. Furthermore, specific uses and method of treatment are disclosed. The recombinant retroviral vectors are particularly efficient in splicing and transduction in a safe manner.

BACKGROUND

Viral vectors have been used for gene therapy for decades and recently improved designs, use for curing human disorders has become limitless. Of particular interest in the field of viral vectors are the vectors originating from mouse mammary tumor virus (MMTV) and Type B leukemogenic virus (TBLV). MMTV is a beta retrovirus, which causes breast cancer and T-cell lymphomas in mice. It is historically classified as a 'simple retrovirus' as it only contains the structural genes necessary for virus particle formation (gag/env) and those coding for enzymes required for virus replication (pro/pol). However, also other genes have been found in MMTV, such as those encoding additional viral factors, sag (superantigen) and rem. Previously presented is the DA024 MMTV-based vector (Rizvi et al, 2009), which was able to efficiently carry out marker gene delivery in human cells, independent of the viral accessory protein, Rem. However, for therapeutic gene delivery into humans, this vector had potential safety concerns since earlier, others and the inventors have shown that retroviruses have the ability to cross-package RNAs from phylogenetically-distant retroviruses (Rizvi et al., 1993; Yin and Hu, 1997; Motomura et al., 2008; Al Dhaheri et al., 2009; Al Shamsi et al., 2011; reviewed in Ali et al., 2016). DA024 contained the RNA packaging signal, which could allow encapsidation of the vector RNA by either endogenous or exogenous retroviral proteins present in the host, such as individuals infected with human retroviruses like HIV or HTLV.

Viruses overall for use in gene therapy are considered as efficient carriers of genes of interest, and at the same time show potential for replication in the recipient cells. Within the field of pharmaceutical products comprising a viral vector as the active pharmaceutical ingredient (API), more and more products have been approved by the regulatory authorities. However, safe and efficient gene therapy delivery systems is still needed for continued pharmaceutical development.

The present invention provides additional safety features to make in particular MMTV- and TBLV-based vectors safer, yet efficient, for gene delivery in a pharmaceutical and therapeutic setting.

SUMMARY

In one aspect, the present invention relates to a recombinant retroviral vector, which is a Split-Intron Self-Inactivating (SIN) vector, comprising: a viral major splice donor (mSD) comprising a mutation in each of the positions corresponding to positions 5, 6, 15 and 16 of SEQ ID NO: 1, and optionally in the positions corresponding to positions 4, 17 and 18 of SEQ ID NO: 1; a mouse mammary tumor vector long terminal repeat (MMTV-LTR) or a Type B leukemogenic virus long terminal repeat (TBLV-LTR); a eukaryotic splice acceptor (eSA); and a eukaryotic splice donor (eSD).

In a further aspect, the present invention relates to an expression plasmid comprising the recombinant viral vector of the present invention.

In another aspect, the present invention relates to a viral particle comprising the recombinant viral vector of the present invention.

In another aspect, the present invention relates to a producer cell comprising the recombinant viral vector and/or the viral particle of the present invention.

In another aspect, the present invention relation to a cell-line comprising the viral particle of the present invention.

In a further aspect, the present invention relates to a composition comprising the recombinant viral vector, the expression plasmid, the viral particle, the producer cell, or the cell-line of the present invention.

In another aspect of the present invention, a pharmaceutical composition comprising the viral particle or the cell line of the present invention, is disclosed.

In another aspect of the present invention, a kit comprising the recombinant retroviral vector and/or the expression plasmid of the present invention, is disclosed.

In yet other aspects of the present invention, method of producing a viral particle, method of treatment, method of gene therapy, and uses of the recombinant retroviral vector, viral particle, producer cell, and/or cell line of the present invention are disclosed.

BRIEF DESCRIPTION OF FIGURES

The patent or application file contains at least one drawing executed in color. Copies of this patent or patent application publication with color drawing(s) will be provided by the Office upon request and payment of the necessary fee.

1A) Design of MMTV three plasmids. 1B) HEK 293T cells used for transient transfection of three plasmids as packaging cell line for the production of pseudotyped viral particles. 1C) Infection of target human HeLa T4 cells with pseudotyped MMTV viral particles containing hygromycin as transgene for gene delivery FIG. 3: Design of the MMTV split intron (SIN) transfer vectors.

The vector design is shown A) before, and B) after transduction into target HeLa T4 cells. Large arrows illustrate the mRNAs produced from the CMV, SV40, and U3 promoters found in these vectors, before and after transduction. Small arrows show the location of primers used for integration and transcript analysis. The abbreviations are as follows: CMV, cytomegalovirus promoter; R, repeat sequences of MMTV LTR; U5, unique 5' sequences of MMTV LTR; U3, unique 3' sequences of MMTV LTR; SV, simian virus 40 promoter; CTE, constitutive transport element from MPMV; mSD, major splice donor; eSA, eukaryotic splice acceptor; eSD, eukaryotic splice acceptor from SV40. Psi (Ψ), RNA packaging signal.

FIG. 4: Secondary structure of MMTV bifurcated packaging signal stem loop 4. The abbreviations are as follows: WT, wild type; mSD, major splice donor; mSD1, mSD mutant 1; mSD2 mutant 2. Red color highlights the mutations introduced. Blue highlights the sequence of the mSD and Gag ATG within the sequence and SL4 loop.

Figure 5:
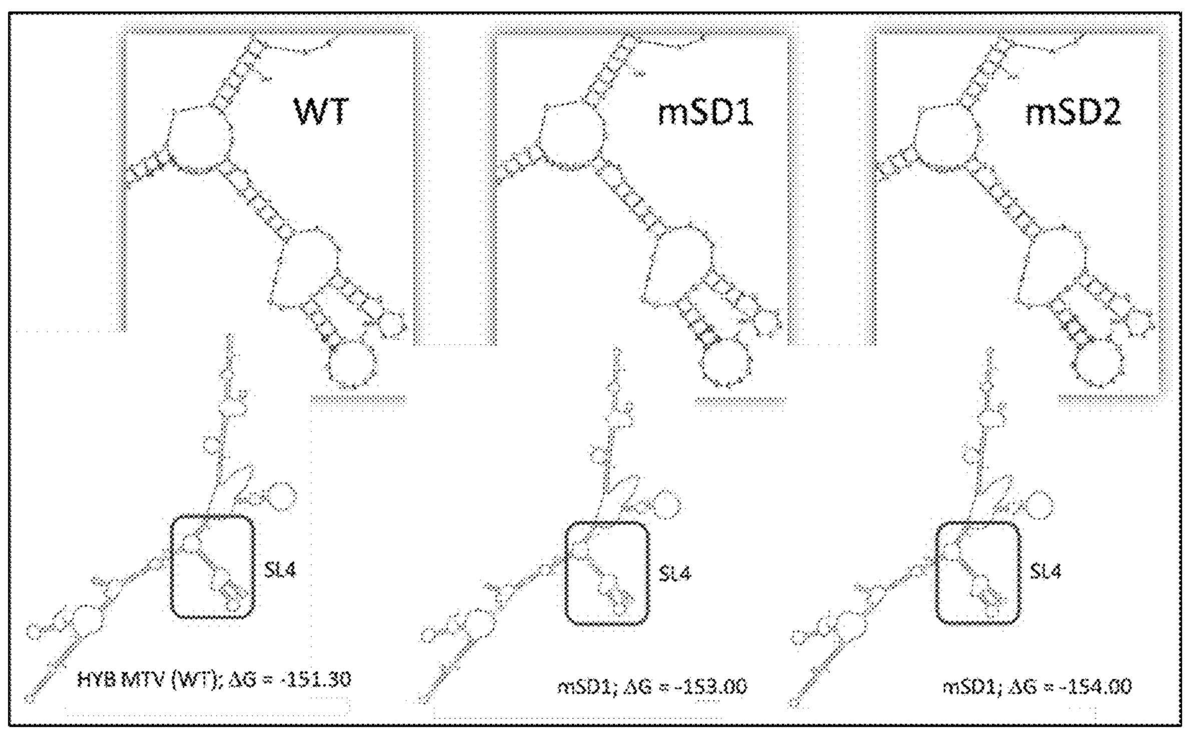

FIG. 5: Secondary structure analysis of the MMTV packaging signal RNA following introduction of mutations in the retroviral major splice donor, mSD. The abbreviations are as follows: WT, wild type; mSD1 & 2, mSD mutant 1 & 2. The bottom panels show the whole structure of the 5' end of MMTV genome, from R to the first 400 nucleotides of gag. The red box highlights the bifurcated stem loop 4 (SL4) of the MMTV RNA packaging signal shown as an enlargement above. Blue highlights the sequence of the mSD and Gag ATG in the WT structure, while orange highlights mutations introduced in the vectors.

Figure 6:
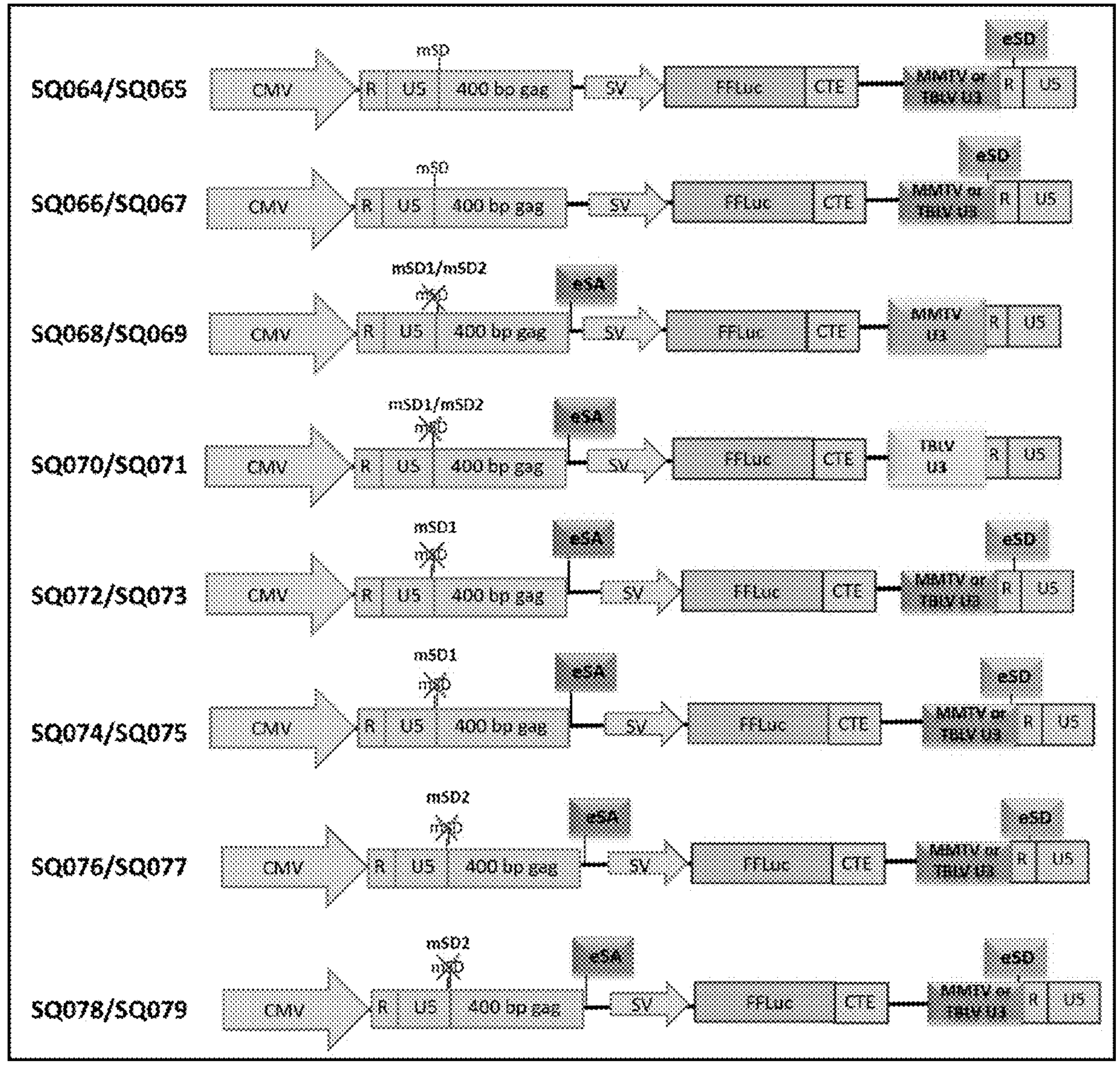

FIG. 6: Next generation of MMTV-based split intron SIN transfer vectors. The abbreviations are as follows: CMV, cytomegalovirus promoter; R, repeat sequences of MMTV LTR; U5, unique 5' sequences of MMTV LTR; U3, unique 3' sequences of TBLV LTR; SV, simian virus 40 promoter; CTE, constitutive transport element from MPMV; mSD, major splice donor; eSA, eukaryotic splice acceptor; eSD, eukaryotic splice acceptor from SV40; Red X, mutation of mSD. Even numbered vectors had the MMTV LTR, while the odd numbered vectors had the TBLV LTR.

Figure 7:
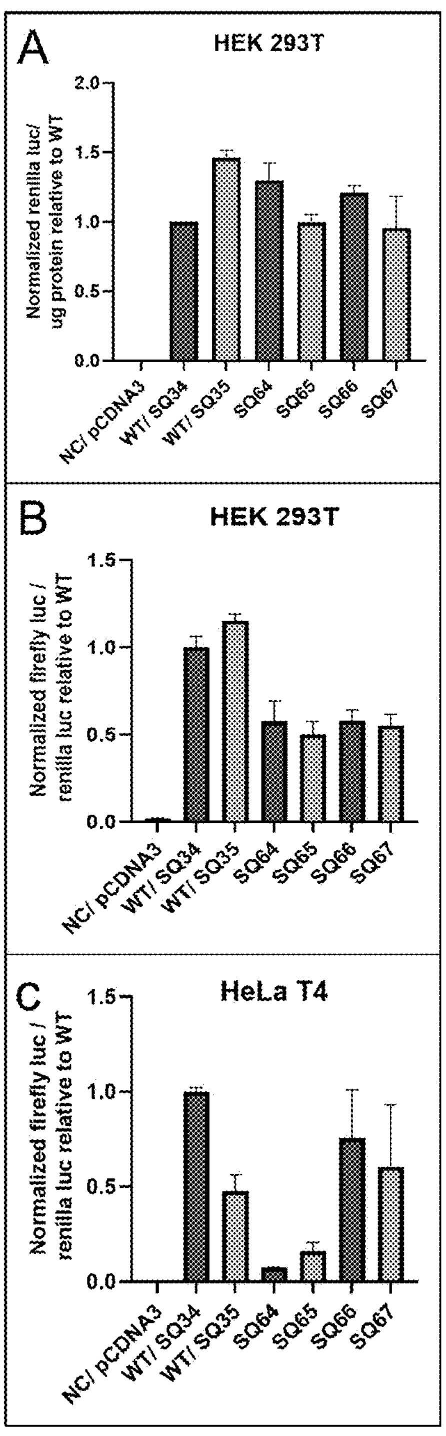

FIG. 7: Test of the split intron SIN transfer vectors with eSD insertions in the three plasmid trans-complementation assay. The test transfer vectors were transfected in HEK 293T cells along with the packaging construct JA10, the Env expression vector, MD.G, and the transfection control plasmid, RL-TK, expressing *Renilla* luciferase. 7A) Transfection efficiency of each transfer vector as measured by expression of *Renilla* luciferase activity per microgram protein. 7B) Analysis of the modified intermediate split intron SIN vectors, SQ64-SQ67, in HEK 293T producer cells via normalized reporter gene expression after transfection compared to the wild type (WT) transfer vectors. 7C) Transduction efficiency of the modified intermediate split intron SIN vectors, SQ64-SQ67 having an active eSD site inserted in 3' LTR compared to the wild type vectors. This experiment represents one of several representative experiments with similar results.

Figure 8:
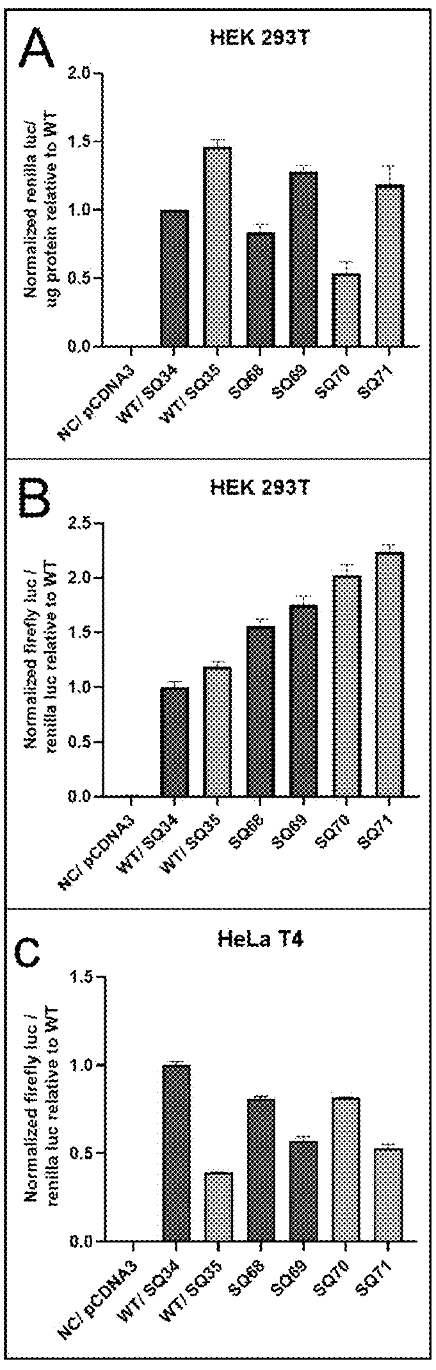

FIG. 8: Test of the intermediate split intron SIN vectors with mutations of mSD and eSA insertions in the three plasmid trans-complementation assay. The test transfer vectors were transfected in HEK 293T cells along with the packaging construct JA10, the Env expression vector, MD.G, and the transfection control plasmid, RL-TK, expressing *Renilla* luciferase. 8A) Transfection efficiency of each transfer vector as measured by expression of *Renilla* luciferase activity per microgram protein. 8B) Analysis of the modified intermediate split intron SIN vectors, SQ68-SQ71, in HEK 293T producer cells via normalized reporter gene expression after transfection compared to the wild type (WT) transfer vectors. 8C) Transduction efficiency of the modified intermediate split intron SIN vectors, SQ68-SQ71 having an active eSD site inserted in 3' LTR compared to the wild type vectors.

Figure 9:
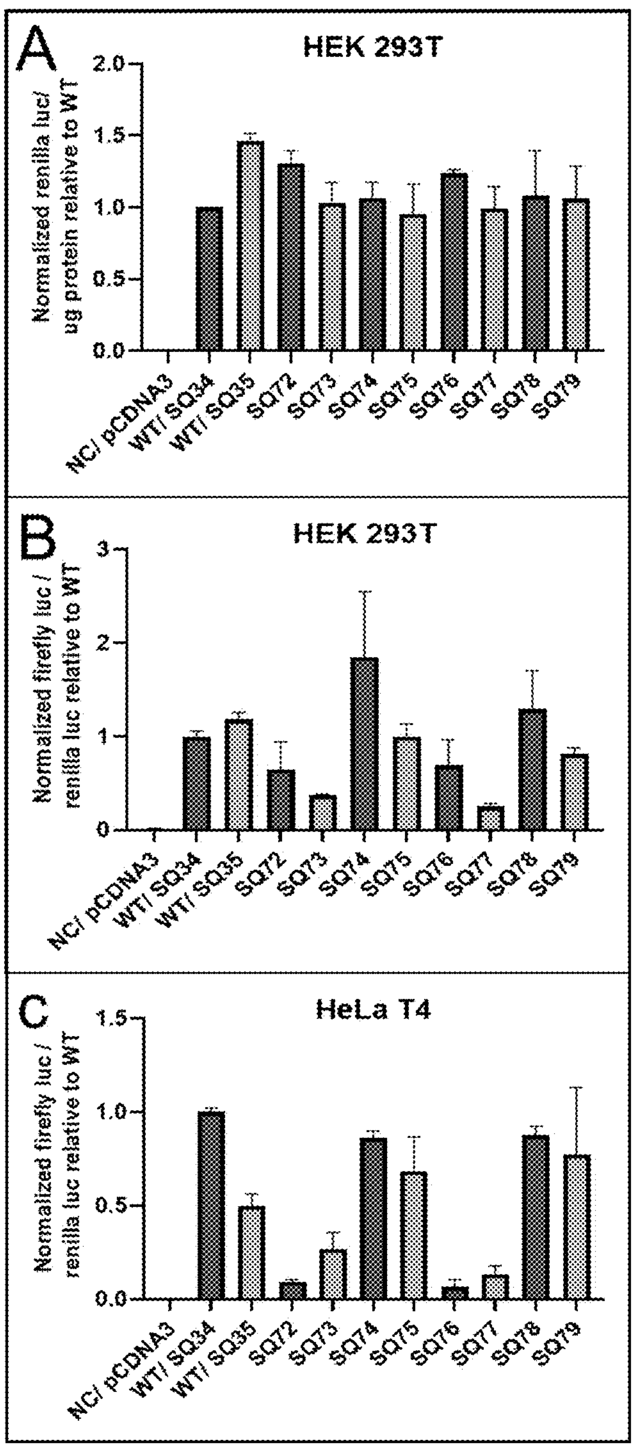

FIG. 9: Test of the final split intron SIN vectors in the three plasmid trans-complementation assay. The test transfer vectors were transfected in HEK 293T cells along with the packaging construct JA10, the Env expression vector, MD.G, and the transfection control plasmid, RL-TK, expressing *Renilla* luciferase. 9A) Transfection efficiency of each transfer vector as measured by expression of *Renilla* luciferase activity per microgram protein. 9B) Analysis of the modified intermediate split intron SIN vectors, SQ72-SQ79, in HEK 293T producer cells via normalized reporter gene expression after transfection compared to the wild type (WT) transfer vectors. 9C) Transduction efficiency of the modified final split intron SIN vectors, SQ72-SQ79, compared to their wild type vectors. This experiment represents one of several representative experiments with similar results.

Figure 10:
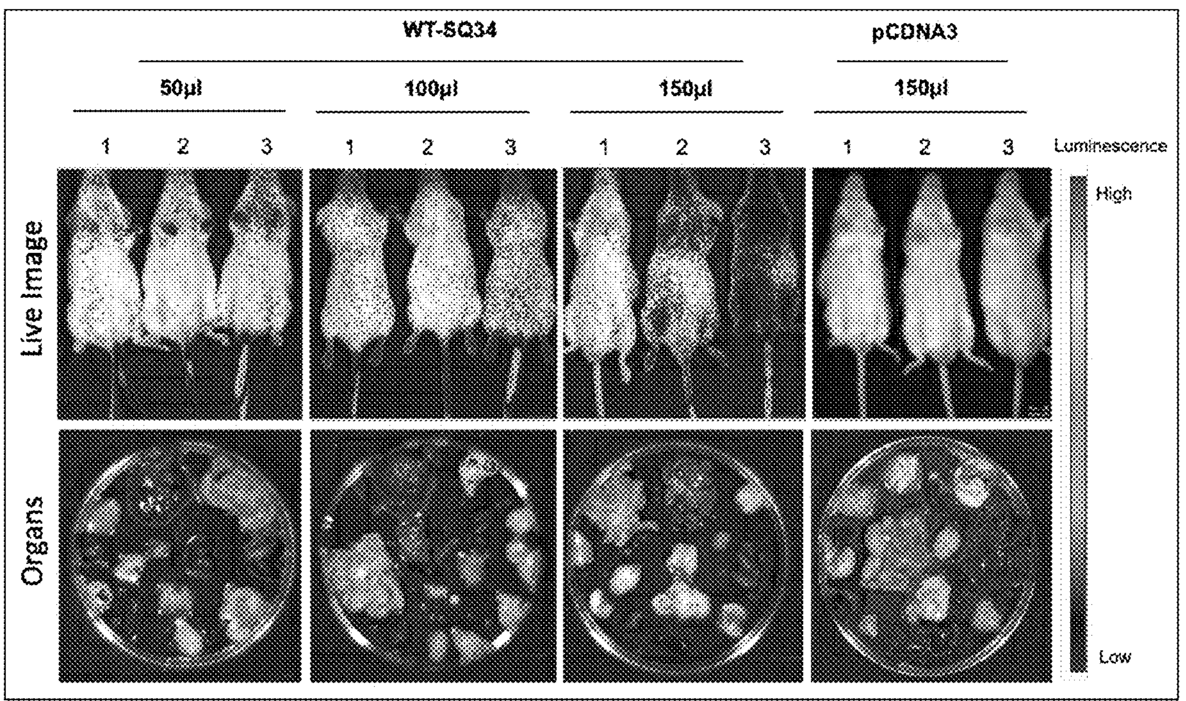

FIG. 10: Dose-dependent gene delivery of MMTV-based wild type (WT) vector, SQ034, in BALB/c mice. Upper panel. Live BALB/c mice imaged via In Vivo Imaging System (IVIS) 72 hours post viral vector delivery by intravenous injection. Lower panel. BALB/c mice organs imaged 1 month after wild type SQ034 viral vector delivery FIG. 11: Gene delivery of MMTV-based wild type (WT) and SIN virions in BALB/c. Upper panel. Live mice imaged via In Vivo Imaging System (IVIS) 72 hours post viral vector delivery. Lower panel. BALB/c mice organs imaged 1 month after intravenous injection showing MMTV WT (SQ034) and SIN (SQ074 and SQ078) viral vector delivery.

Figure 12:
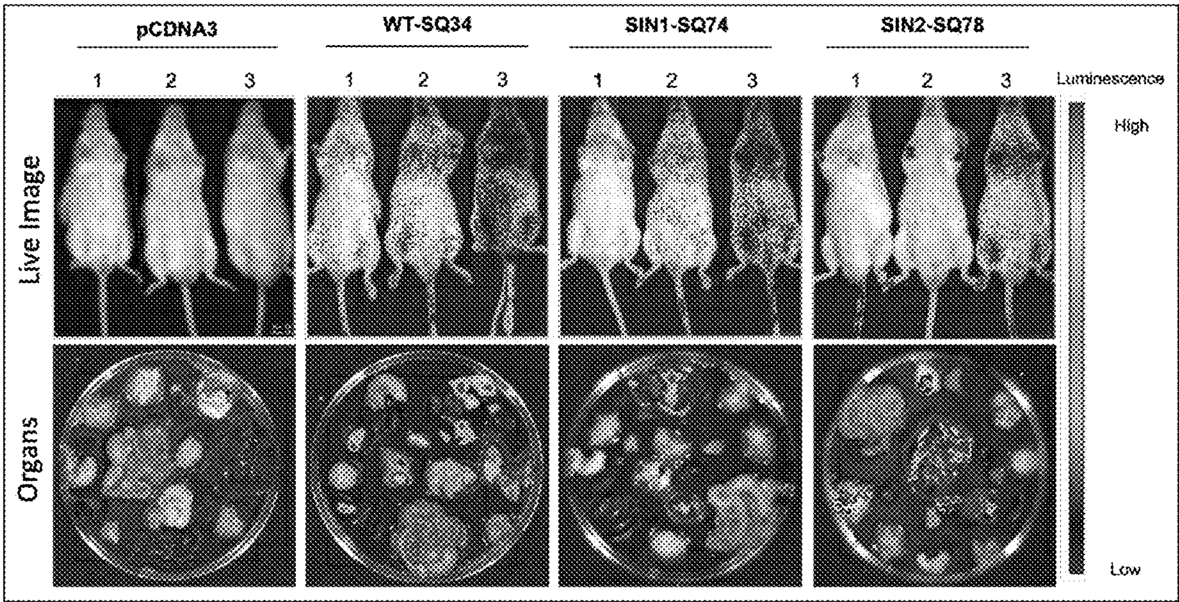

FIG. 12: Luciferase gene delivery in C57BL/6 mice brain using MMTV wild type (WT) and SIN vectors. Luciferase gene expression upon successful transgene delivery using MMTV-based WT (SQ034) and SIN (SQ074 & SQ078) vectors by stereotaxic injection in substantia nigra pars *compacta* (SNC) of mice brain which was monitored using In Vivo Imaging System (IVIS) imaging 48 hours after injections.

Figure 13:
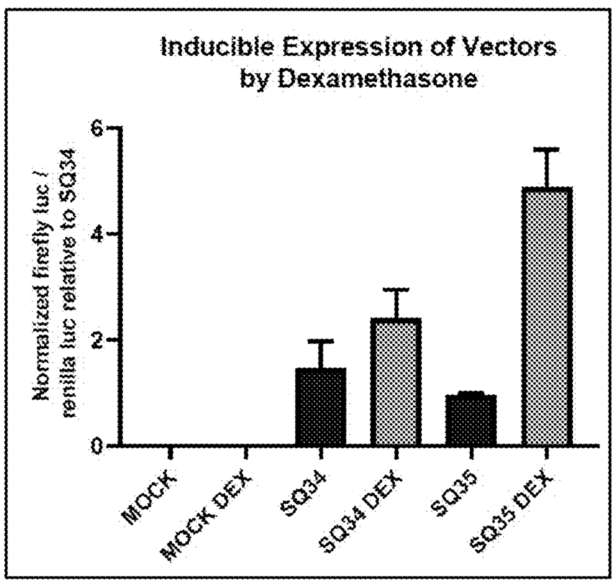

FIG. 13: Hormone inducibility of the wild type MMTV- and TBLV-based gene transfer vectors (SQ34 and SQ35, respectively) after infection of HEK293T cells. The transfer vectors, SQ34 or SQ35, were transfected into HEK293T cells along with the packaging construct JA10 and the VSV-G Env expression vector, MD.G. Virus produced in these transfected HEK293T cells was then used to infect fresh HEK293T cells either in the presence or absence of $10^{-6}$M Dexamethasone (DEX). Mock, the pCDNA3 expression vector was transfected along with JA10 and MD.G for mock virus production. A *Renilla* luciferase expression plasmid was co-transfected and used as a transfection control.

DETAILED DESCRIPTION

In a first aspect, the present invention relates to a recombinant retroviral vector, which is a Split-Intron Self-Inactivating (SIN) vector, comprising: a viral major splice donor (mSD) comprising a mutation in each of the positions corresponding to positions 5, 6, 15, and 16 of SEQ ID NO: 1, and optionally in the positions corresponding to positions 4, 17, and 18 of SEQ ID NO: 1; a mouse mammary tumor vector long terminal repeat (MMTV-LTR) or a Type B leukemogenic virus long terminal repeat (TBLV-LTR); a eukaryotic splice acceptor (eSA); and a eukaryotic splice donor (eSD).

The term "recombinant retroviral vector" as used herein refers to a retroviral vector well-known to the skilled person, but which has been modified. Modifications comprise introduction of specific regions, framework regions that may be considered relevant to introduce to the retroviral virus. Thus, a retroviral vector is a genetically engineered RNA virus modified to deliver genes of interest into cells. Such vectors are used in gene therapy and research, allowing for stable integration of the gene of interest into the host/target cell's DNA. The retroviral vector will naturally convert their RNA into DNA and insert it into the host genome.

The term "Split-Intron Self-Inactivating (SIN) vector" as used herein refers to a retroviral vector designed to improve gene expression and safety in gene therapy. Such SIN vectors achieve safer gene expression by strategically placing an intron around the viral packaging signal (psi) within the vector, allowing for its efficient removal from the vector transcripts after vector integration into the target cells.

The term "major splice donor (mSD)" as used herein refers to a specific location within a pre-mRNA sequence, specifically the 5' end of an intron, where the spliceosome initiates the removal of the intron during RNA splicing. It may be considered as the 'start' of the cutting process that removes the non-coding intron from the RNA transcript.

The term "mouse mammary tumor vector long terminal repeat" (MMTV-LTR) as used herein refers to the region of DNA that is essential for the virus's ability to replicate and integrate into a host's genome. Retroviral vectors based on the mouse mammary tumor vectors (MMTVs) were one of the earliest to be developed; however, they have been used mostly for research purposes and did not proceed to clinical trials. It is well-known for the skilled person what LTR's are, but for completeness, the LTR acts as both a promoter and a region where the viral RNA can be replicated.

The recombinant viral vector of the present invention may contain several regulatory elements, including a negative regulatory element (NRE) and/or a hormone response element (HRE). Such features are key for regulating the virus's expression. The present inventors have found certain embodiments of the present invention, wherein the lack of the negative regulatory element (NRE), such as in a TBLV-LTR, results in enhanced hormone responsiveness. One embodiment of the present invention thus describes the recombinant retroviral vector of the present invention, comprising a hormone response element (HRE). One embodiment of the present invention describes the recombinant retroviral vector of the present invention comprising a negative regulatory element (NRE). One embodiment of the present invention describes the recombinant retroviral vector of the present invention lacking a negative regulatory element (NRE). One embodiment of the present invention further describes the recombinant retroviral vector of the present invention, wherein said recombinant retroviral vector is inducible by use of hormones. One or more embodiments also describe expression of the gene of interest once integrated into the host's genome, which can be controlled by a relevant hormone suitable to practice the present invention.

The term "Type B leukemogenic virus long terminal repeat" (TBLV-LTR) as used herein, refers to the modified LTR observed in the TBLV variant of MMTV that causes T-cell lymphomas and leukemia in mice. This variant differs from MMTV only in its LTR which contains two general modifications: a 443 bp deletion and substitution of a 124-bp sequence (Ball et al., 1988). The deletion results in removal of the negative regulatory element (NRE) present in the MMTV LTR responsible for tissue-specific expression by MMTV. The substitution represents triplication of the regions flanking the deletion, creating a T-cell specific enhancer (Mertz et al., 2001). These modifications also result in truncation of the superantigen (sag) gene encoded within the LTR, an aspect shown to be dispensable for T-cell lymphomagenesis (Mustafa et al., 2003). In other words, the deletion and substitution in the LTR are sufficient for inducing lymphomas by TBLV. Retroviral vectors based on Type B leukemogenic virus (TBLV) have, to the best of the inventors' knowledge not been developed. This is partly due to the weak basal promoter of MMTV found within U3 requiring hormone stimulation for its induction.

The recombinant retroviral vector is based on the non-human retroviruses MMTV, and TBLV, which reduces the risk of recombination with human retroviruses, and therefore, potential generation of replication-competent retroviruses in treated patients due to the phylogenetic distance between primate and rodent species. Other advantages of the MMLV and TBLV, are that they do not contain the same potential to activate oncogenes via integration as other non-human retroviral vectors which are mainly based on murine leukemia virus (MLV) or feline immunodeficiency virus (FIV), and thereby the risk of developing cancer is non-present. Use of MLV-based vectors for human gene therapy is known, but for developing cancer, this particular retroviral vector is undesirable. In particular, the MMTV has an integration profile that is safer for gene therapy purposes since it seems to be the most random retroviral vector with no preference for any specific genomic location.

Furthermore, MMTV-based vectors, such as the MMTV and the TBLV of the present invention, are believed to be more effective for therapeutic gene delivery as MMTV can infect non-dividing cells. This is unlike other retroviruses and a property belonging to lentiviruses such as HIV. Hence, MMTV and/or TBLV-based vectors of the present invention can be efficiently used in gene therapy as most tissues amenable to gene therapy are composed of terminally differentiated, non-dividing cells, cells which are hard to deliver genes to, such as those of the brain, heart, and muscles.

The term "eukaryotic splice acceptor (eSA)" as used herein, refers to the region at the 3' end of an intron that signals the spliceosome to remove the intron and join the flanking exons. It is characterized by the conserved AG sequence, which is essential for the spliceosome's recognition and processing. This AG sequence, along with other elements like the polypyrimidine tract and branch point, helps the spliceosome recognize and remove the intron form the pre-mRNA.

The term "eukaryotic splice donor (eSD)" as used herein, refers to the 5' end of an intron. It is the location where the intron is cut out from the pre-mRNA during splicing, a process that removes introns and joins the remaining exons together to form mature mRNA. The splice donor site typically has a consensus sequence of GU at its 5' end. This sequence helps the spliceosome, the complex that carries out splicing, recognize and cut the intron at the correct location.

In one embodiment, the mSD has a sequence corresponding to SEQ ID NO: 2 or SEQ ID NO: 3, preferably SEQ ID NO: 3. In one embodiment, the mSD has a sequence corresponding to SEQ ID NO: 3. Sequences identified as SEQ ID NO: 2 and SEQ ID NO: 3 of the present invention contain specific modifications introduced into the mSD to disrupt its function as a splice donor.

Figure 1:
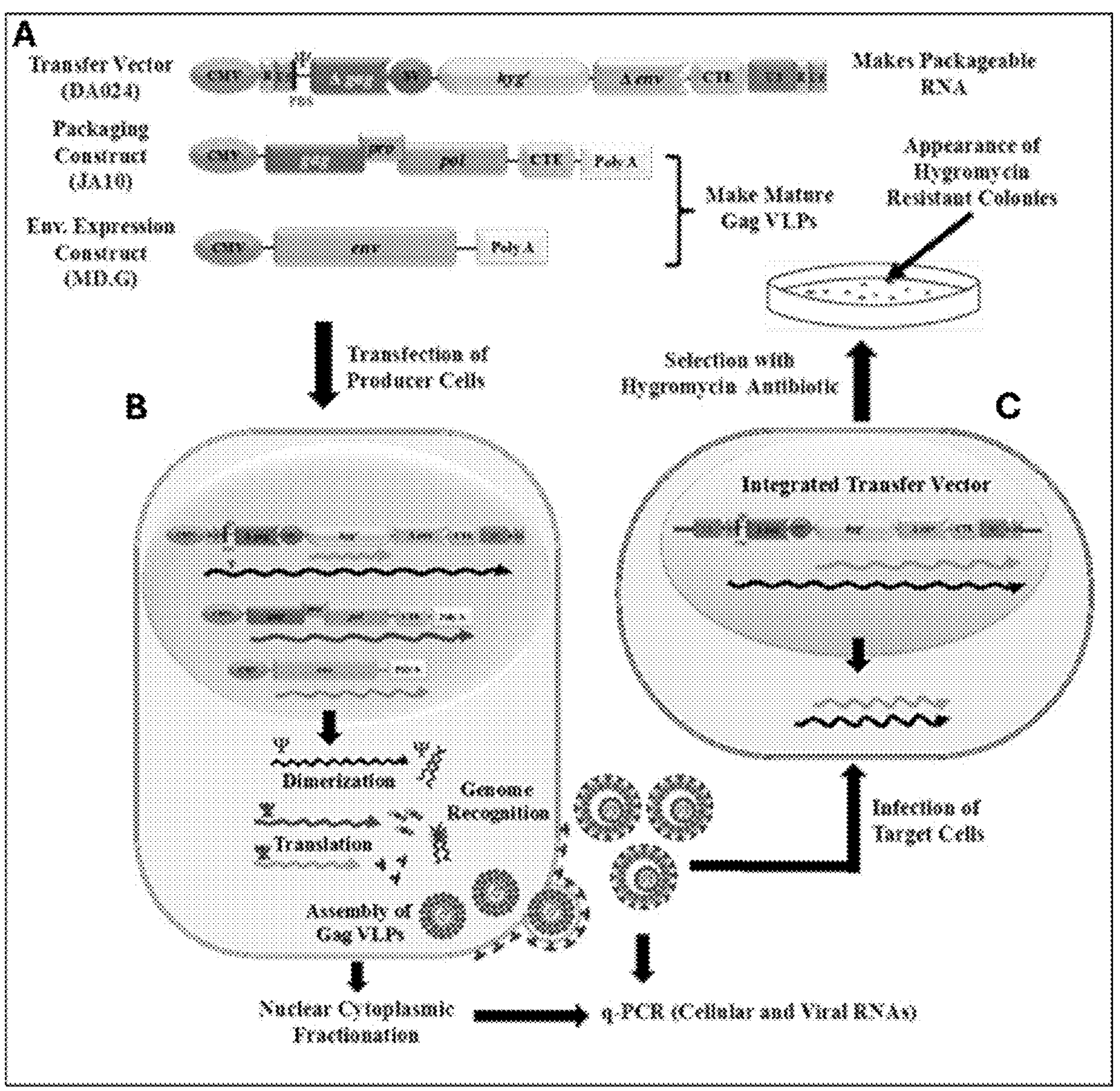
FIG. 1: MMTV-based three plasmid trans-complementation assay.

The mSD of the present invention comprises specific mutations which have been carefully placed as to not to disturb the secondary structure of the RNA. Thus, despite these mutations, the native structure of the RNA is maintained. In particular, the loops of the RNA region around the mSD are important for packaging of the virus particle. The specific mutations in the viral major splice donor (mSD) inactivate the splice donor activity. This ensures that the transfer vector RNA will not be completely spliced so that it will be incorporated into the newly forming virus particles. The mSD is found within the packaging signal or "psi (ψ)" of the virus—sequences found at the 5' of the viral genome that assume a three-dimensional (3D) structure (FIG. 1—upper panel). This structure is needed for packaging of the vector RNA into the virus particles by the viral structural proteins.

Mutations of the mSD can affect the secondary RNA structure of the packaging signal, rendering the vector RNA defective for encapsidation into the viral particles. However, the prior art vectors failed to provide the right set of mutations which compromised the packaging signal. The inventors of the present invention have identified mutations that specifically inactivate the mSD without affecting the 3D structure of the MMTV ψ (psi), thereby ensuring proper packaging of the vector RNA carrying the gene of interest into the virus particles during virion assembly.

In one embodiment, the eukaryotic splice acceptor (eSA) has at least 90% sequence identity with SEQ ID NO: 4, such as at least 95%, such as at least 97%, such as at least 99% sequence identity with SEQ ID NO: 4. The eSA of the present invention may be any eSA known in the field. However, in particular embodiments, the eSA will have at least some sequence identity with SEQ ID NO: 4, as disclosed herein. In one embodiment, the eSA is SEQ ID NO: 4.

In one embodiment, the eukaryotic splice donor (eSD) corresponds to positions 20-35 of SEQ ID NO: 5, and which has at least 90% sequence identity with positions 20-35 of SEQ ID NO: 5, such as at least 95%, such as at least 97%, such as at least 99% sequence identity with positions 20-35 of SEQ ID NO: 5. In one embodiment, the eSD is positions 20-35 of SEQ ID NO: 5.

The eSD of the present invention may be any eSD known in the field. However, in embodiments, the eSD will have at least some sequence identity with SEQ ID NO: 5, as disclosed herein.

The term 'U3 region' describes the unique sequences found at the 3' end of a viral genome, such as an MMTV viral genome and/or a TBLV viral genome.

The term 'U5 region' describes the unique sequences found at the 5' end of a viral genome, such as an MMTV viral genome and/or a TBLV viral genome.

The term 'R region' describes a repeat sequence flanking at least one of a U3 and/or U5 region.

The eSD introduced to the 3' U3 region of the retroviral vector creates an artificial "intron" upon reverse transcription and integration: The 3' U3 region gets duplicated to the 5' end of the retroviral vector wherein the CMV promoter is replaced by the 3' U3 after reverse transcription. In the presence of the mutations in mSD, the effect of this rearrangement of splice sites ensures that efficient splice sites are introduced into the vector once it is transduced into the target cells, but not at the stage of virion production. Insertion of eSD also ensures the complete and desired self-inactivation of the vector, limiting the ability of its RNA to be packaged following integration and subsequent transcription. The size of eSD used and its specific location within the U3 region is important in relation to its effective functioning and have been optimized by the present inventors. Insertion of the eSD at the end of U3, but before the polyA region led to viable vectors with efficient capability of gene expression and/or its delivery.

In one embodiment, the MMTV-LTR or the TBLV-LTR comprises the eSD. In one embodiment, the MMTV-LTR comprises the eSD. In one embodiment, the TBLV-LTR comprises the eSD.

In one embodiment, the MMTV-LTR or the TBLV-LTR comprises SEQ ID NO: 5. In one embodiment, the MMTV-LTR comprises SEQ ID NO: 5. In one embodiment, the TBLV-LTR comprises SEQ ID NO: 5.

In one embodiment, the eSD is comprised within the U3 region of the MMTV-LTR.

In one embodiment, the eSD is comprised within the U3 region of the TBLV-LTR.

In one embodiment, the eSD is comprised between the R region and the U5 region of the MMTV-LTR.

In one embodiment, the eSD is comprised between the R region and the U5 region of the TBLV-LTR.

In one embodiment, the eSD is comprised between positions 1160-1206 of SEQ ID NO:6.

In one embodiment, the eSD is comprised between positions 840-886 of SEQ ID NO:7.

In one embodiment, the eSD is comprised between positions 1150-1170 of SEQ ID NO:6.

In one embodiment, the eSD is comprised between positions 830-850 of SEQ ID NO:7.

Preferably, in one embodiment, the eSD is comprised at the end of the U3 region of the MMTV-LTR.

Preferably, in one embodiment, the eSD is comprised at the end of the U3 region of the TBLV-LTR.

More preferably, in one embodiment, the eSD is comprised between positions 1125-1171 of SEQ ID NO: 6.

More preferably, in one embodiment, the eSD is comprised between positions 805-851 of SEQ ID NO: 7.

More preferably, in one embodiment, the eSD is comprised between positions 1115-1135 of SEQ ID NO: 6.

More preferably, in one embodiment, the eSD is comprised between positions 795-815 of SEQ ID NO: 7.

More preferably, in one embodiment, the eSD is inserted in position 1125 of SEQ ID NO: 6.

More preferably, in one embodiment, the eSD is inserted in position 805 of SEQ ID NO: 7.

It is well-known in the art that viruses may alter their sequences over time to enhance the virus's properties. Therefore, it is understood that the sequence of the MMTV and/or TBLV of the present invention may have diverse sequence but still be useful and perform according to the purpose of the present invention. Thus, in one embodiment, the MMTV-LTR has at least 90% sequence identity with SEQ ID NO: 6, such as at least 95%, such as at least 97%, such as at least 99% sequence identity with SEQ ID NO: 6; or the TBLV-LTR has at least 90% sequence identity with SEQ ID NO: 7, such as at least 95%, such as at least 97%, such as at least 99% sequence identity with SEQ ID NO: 7. In one embodiment, the MMTV-LTR is SEQ ID NO: 6. In one embodiment, the TBLV-LTR is SEQ ID NO: 7.

As stated above, the MMTV and the TBLV are hormone inducible so that expression of the gene of interest can be controlled, i.e., where the gene of interest should only be expressed when required, administration of the relevant hormone will control when the gene of interest should be expressed. Thus, in one embodiment, the MMTV-LTR or the TBLV-LTR is inducible, such as by a hormone, such as a glucocorticoid hormone, such as dexamethasone (Dex).

When the vector is hormone inducible, the resulting expression plasmid which can express MMTV structural proteins at high levels to make virus particles. These virus particles carry the genetic material from the gene transfer vectors with the therapeutic gene of interest. Thereby, it is possible to make high titers of virus for successful gene delivery in humans, which is currently a limitation of any other retrovirus-based gene therapy.

In one embodiment, the recombinant retroviral vector comprises an exogenous gene of interest. The term "exogenous gene of interest" as used herein, refers to a gene that is introduced into an organism from an external source, rather than being part of the organism's own genetic markup. This gene may be any therapeutic gene that is useful for the gene therapy. Any such genes may be correcting the defects of certain genes in the patient, i.e., by introducing a healthy gene into the patient's cells.

In one embodiment, the recombinant retroviral vector comprises a promoter operably linked to the exogenous gene of interest.

In one embodiment, the recombinant retroviral vector comprises a constitutive transport element (CTE), such as a Mason-Pfizer monkey virus (MPMV), such as a CTE having at least 90% sequence identity with SEQ ID NO: 8. In one embodiment, the CTE is SEQ ID NO: 8. The term "constitutive transport element (CTE)" as used herein, refers to a conserved RNA sequence of the retrovirus that facilitates the nuclear export of unspliced RNA. CTEs are crucial for the life cycle of type D retroviruses, as they ensure that unspliced viral RNA is transported from the nucleus to the cytoplasm, where it can be translated and replicated. CTEs interact with cellular proteins, including Tap an dNXF1, which are part of the cellular RNA export machinery. This interaction allows the viral RNA to bypass the normal nuclear retention mechanisms that prevent intron-containing RNAs from being exported.

The inclusion of the CTE aids in the successful expression of the therapeutic gene without the need of an associated viral protein. Therapeutic genes can be expressed without the use of a fourth vector normally needed to facilitate gene expression through the preferable addition of the CTE.

Retroviral vectors based on the mouse mammary tumor vectors (MMTVs) were one of the earliest to be developed; however, they have been used mostly for research purposes and did not proceed to clinical trials. Retroviral vectors based on Type B leukemogenic virus (TBLV) have, to the best of the inventors' knowledge not been developed. This is partly due to the weak basal promoter of MMTV found within U3 requiring hormone stimulation for its induction. It was previously shown that this caveat could be overcome by using the strategy tested in feline immunodeficiency virus vector development (FIV; Poeschla et al, 1999). The inventors have overcome this problem through the creation of a hybrid MMTV LTR comprising a strong eukaryotic promoter from the cytomegalovirus (CMV) which replaced the U3 region of the LTR on the 5' end of the vector, creating a CMV/R/U5 LTR. Thus, one of the advantages of the present invention is that gene expression from such vectors becomes independent of the need of hormone stimulation necessary for virion production in the HEK 293T producer cells. After infection of target cells, the CMV promoter in the vector is replaced by the U3 region from the 3' LTR, while the gene of interest is expressed from an internal promoter, such as the SV40 promoter, independent of the weak U3 promoter present in the reconstituted 5' LTR. Furthermore, the replacement using a strong CMV promoter allows robust gene expression with a broad host-range from this LTR as opposed to the tissue-specific gene expression from the natural MMTV promoter.

Thus, in one embodiment, the recombinant retroviral vector comprises a promoter upstream of the mSD, preferably a CMV promoter. In another embodiment, the recombinant viral vector comprises a CMV/R/U5 LTR upstream of the mSD. In one embodiment, the recombinant viral vector of the present invention comprises a cytomegalovirus (CMV) promoter. In one embodiment, the CMV promoter is located upstream of the mSD. In one embodiment, the CMV promoter is a strong promoter. In one embodiment, the CMV promoter is a eukaryotic promoter. In one embodiment, the CMV promoter is a strong eukaryotic promoter. In one embodiment, the CMV promoter replaces the U3 region of the LTR on the 5' end of the vector. In one embodiment, the recombinant viral vector of the present invention comprises a CMV/R/U5 LTR. In one embodiment, the CMV/R/U5 LTR is located upstream of the mSD.

The inventors of the present invention have found that a retroviral virus with the following elements is of particular benefit. Thus, in one particular embodiment, the recombinant retroviral virus comprises in order from 5' to 3': the mSD, the eSA, and the MMTV-LTR comprising the eSD or the TBLV-LTR comprising the eSD. In another embodiment, the recombinant retroviral virus comprises in order from 5' to 3': a promoter upstream of the mSD, the mSD, the eSA, an exogenous gene of interest, a CTE, and the MMTV-LTR comprising the eSD or the TBLV-LTR comprising the eSD.

Incorporation in the particular order, makes the vectors safe, efficient, and stable for long term gene expression without the risk of creating TNA transcripts expressing the therapeutic gene that can be packaged by related endogenous or exogenous viruses that could spread in humans.

Sequence Identity

The term "sequence identity" as used herein describes the relatedness between two amino acid sequences or between two nucleotide sequences, i.e., a candidate sequence (e.g., a mALP gene) and a reference sequence based on their pairwise alignment. For purposes herein, the sequence identity between two amino acid or between two nucleotide sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 5.0.0 or later (available at https://www.ebi.ac.uk/Tools/psa/emboss needle/). The parameters used are gap open penalty of 10, gap extension penalty of 0.5, and the EBLOSUM62 (EMBOSS version of 30 BLOSUM62) substitution matrix. The output of Needle labelled "longest identity" (obtained using the -nobrief option) is used as the percent identity and is calculated as follows: (Identical Residues×100)/(Length of Alignment−Total Number of Gaps in Alignment).

Expression Plasmid

In a second aspect, the present invention relates to an expression plasmid comprising the recombinant viral vector of the present invention.

The term 'expression plasmid' as used herein refers to a form of vector designed for gene expression within a cell. Such expression plasmids are used in gene therapy and research, allowing for expression of one or more genes of interest in the host or target cell. Methods to develop expression plasmids are well known to the skilled person in the art.

Expression plasmids of the present invention are also suitable for delivery within producer cells, wherein said producer cells are capable of producing viral particles.

Viral Particle

In a third aspect, the present invention relates to a viral particle comprising the recombinant viral vector of the present invention.

The term viral particle as defined herein refers to a molecule, made up of genetic material and a capsid, which contains at least the minimal set of components necessary to induce viral material within one or more target cells. It is to be understood that the term 'viral particle' may be used interchangeably with the term 'virus particle'.

The viral particle is suitable for delivering a gene of interest or transgene into one or more cells.

Packaging a vector genome is a crucial step in the production of infectious, replication-defective viral particles, the actual virions needed for transduction. This is achieved by complementation of all the necessary viral factors/proteins, for example, in the context of a producer cell. The packaging technology has evolved with time to reduce sequences of viral origin for improving safety profile of viral vectors.

The inventors have developed virus particles defective for replication and limited to only a "single round" as the transduced cells will only have the transgene-expressing RNA and no genetic material to make the structural proteins is limited to a single round with no further chance of reinfection.

Viral particles of the present invention are therefore amenable for use in gene therapy and research, allowing for stable integration of the gene of interest into the host or target cell's DNA. One of the key advantages of the present invention is that the viral particles are defective for replication and limited to only a "single round" with no further chance of reinfection.

Thus, the inventors have developed viral particles with favorable efficacy and safety profiles, suitable for use in a range of medical applications, for example in gene therapy, such as ex vivo gene therapy; cancer immunotherapy, such as breast cancer immunotherapy; treatment of genetic diseases; treatment of immune disorders, such as severe combined immunodeficiency (SCID); and/or treatment of infectious diseases. The viral particles are a new generation of self-inactivating, non-lentiviral particles based on a rodent retrovirus that allows efficient therapeutic gene delivery into human dividing and non-dividing cells without the safety concerns arising from the use of primate lentiviral vectors.

In one embodiment, the viral particle is T-cell tropic.

The term 'tropic' refers to a virus, or a viral strain, that has a preference for infecting T cells. The present invention thus describes a viral particle of the present invention for infecting T cells and/or hematopoietic cells. Thus, it is understood that one embodiment of the viral particle of the present invention describes a viral particle which infects T cells, such as high expression T cells, such as CD4+ T cells. Furthermore, in another embodiment, the viral particle infects hematopoietic cells, such as hematopoietic stem cells (HSCs).

The T-cell tropic viral particles developed by the inventors allow for treatments based on lymphocytes to be particularly amenable, showing favourable expression profiles in lymphocytes (white blood cells), and are thus suitable for delivery and use within medical applications, such as gene therapy, immunotherapy and treatment of immune disorders and infectious diseases.

Producer Cell

In another aspect, the present invention relates to a producer cell comprising the recombinant viral vector and/or the viral particle of the present invention.

Thus, in one embodiment, the producer cell comprises the recombinant viral vector of the present invention. In another embodiment, the producer cell comprises the viral particle of the present invention. In another embodiment, the producer cell comprises the recombinant viral vector and the viral particle of the present invention.

The term 'producer cell' as used herein refers to any cell which is capable of producing viral particles, for example, viral particles of the present invention. The term 'producer cell' may be used interchangeably with the term 'packaging cell'.

The present inventors have generated producer cells capable of producing viral particles of the present invention. The producer cell may be transfected, for example in trans with necessary viral factors/proteins, where the genes encoding for these functions can be transfected as independent plasmids. As such, one or more vectors, such as one or more plasmids may be introduced to the cell to produce one or more viral particles of the present invention.

In particular, the producer cell of the present invention may, in a non-limited manner, comprise and/or be transfected with the recombinant viral vector of the present invention, expression plasmids of the present invention, a packaging construct, an envelope expression construct and/or one or more vectors comprising said packaging construct(s), and envelope expression construct(s).

The producer cell may be derived from any suitable cell known to the person in the art, for example, a cell that has been genetically engineered, or synthetic cell. A skilled person in the art would be able to find suitable cell types for producer cells. Examples for suitable cells used to generate producer cells include HEK 293T cells.

Packaging Construct

The producer cell may also comprise one or more packaging constructs.

The term 'packaging construct' as used herein, describes a vector that carries the genes necessary for producing the viral particles, but lacks the viral genome's "packaging signal" (psi, ψ) and thus cannot be packaged into virions itself. It provides the structural and enzymatic proteins (like Gag, Pol, and sometimes accessory proteins) that are required for assembling the viral core and processing the viral precursor proteins.

Packaging constructs have been previously developed with an eye to deliver the "machinery" for creating viral particles, but not the genetic information that the virus would normally carry.

The inventors have developed packaging constructs that express MMTV/TBLV structural genes wherein said packaging constructs allow for easy detection and construction of stable packaging cell lines for high titer virus production.

Envelope Expression Construct

The producer cell may also comprise one or more envelope expression constructs.

The term 'envelope expression construct' refers to an expression plasmid that expresses a viral envelope protein, such as VSV-G. The envelope expression construct may be expressed in either an inducible and/or constitutive manner. Such a manner allows pseudotyping of viral particles, such as MMTV viral particles, which may infect either a broad range of cells or a specific type of cell, depending upon the envelope used.

The present inventors have also developed an envelope expression construct. The envelope expression construct may be a vesicular stomatitis virus envelope G protein (VSV-G Env) expression construct. The envelope expression construct may comprise env. Furthermore, the envelope expression construct may comprise a Kozak sequence.

Kozak Sequences

The packaging construct and/or the envelope expression construct may also comprise Kozak sequences. Kozak sequences are specific nucleotide sequences found in eukaryotic mRNA that aid in initiating and increasing the efficiency of protein translation, acting as a signal for ribosomes to bind and start protein synthesis at the correct location on the mRNA.

Thus, Kozak sequences in the present invention are preferable to initiate and increase the efficiency of protein translation within the producer cell.

Methods to include Kozak sequences in a construct are well known to a skilled person in the art.

Thus, in one embodiment, the producer cell comprises a packaging construct and an envelope expression construct of the present invention. In one embodiment, the producer cell comprises a packaging construct of the present invention. In one embodiment, the producer cell comprises an envelope expression construct of the present invention.

In one embodiment, the producer cell comprises the recombinant viral vector, the packaging construct and the envelope expression construct of the present invention.

In one embodiment, the producer cell comprises the recombinant viral vector, the viral particle, the packaging construct and the envelope expression construct of the present invention.

In one embodiment, the producer cell comprises a HEK 293T cell.

In one embodiment, the packaging construct and/or the envelope expression construct is inducible.

In one embodiment, the packaging construct is inducible. In one embodiment, the envelope expression construct is inducible. In one embodiment, the envelope expression construct is constitutive. In one embodiment, the packaging construct is constitutive.

In one embodiment, the packaging construct comprises gag, pro, and/or pol.

In one embodiment, the packaging construct is a Gag/Pro/Pol expression construct.

In one embodiment, the packaging construct comprises a Kozak sequence.

In one embodiment, the packaging construct comprises a Kozak sequence which has at least 95% sequence identity with SEQ ID NO: 9.

In one embodiment, the Kozak sequence is SEQ ID NO: 9.

In one embodiment, the packaging construct comprises a sequence which has at least 80% sequence identity with SEQ ID NO: 10, such as 85%, such as 90%, such as 95%, such as 99% sequence identity with SEQ ID NO: 10.

In one embodiment, the packaging construct is SEQ ID NO: 10.

In one embodiment, the envelope expression construct comprises env.

In one embodiment, the envelope expression construct comprises a Kozak sequence.

In one embodiment, the envelope expression construct comprises a Kozak sequence which has at least 95% sequence identity with SEQ ID NO: 9.

In one embodiment, the envelope expression construct is a vesicular stomatitis virus envelope G protein (VSV-G Env) expression construct.

In one embodiment, the envelope expression construct comprises a sequence which has at least 80% sequence identity with SEQ ID NO: 11, such as 85%, such as 90%, such as 95%, such as 99% sequence identity with SEQ ID NO: 11.

In one embodiment, the envelope expression construct is SEQ ID NO: 11.

Cell-Line

In another aspect, the present invention relates to a cell-line comprising the viral particle of the present invention.

The term 'cell-line' as used herein refers to one or more cells that can be maintained in culture for a period of time, retaining specific characteristics and functions. The cell-line as used herein is suitable for infection of one or more viral particles of the present invention. The cell-line is also suitable for medical use, such as a method of treatment and method of gene therapy.

Thus, the cell-line as defined herein, is differentiated from a producer cell as defined herein, in that a producer cell is intended for the production of viral particles, whilst the cell-line may be infected with said viral particles and is suitable and may be intended for delivery and/or medical use.

The cell-line may comprise dividing or non-dividing cells. The cell-line may comprise, in a non-limiting manner, for example, mammal-derived cells, such as human (cervical carcinoma HeLa, embryonic kidney HEK293T (used both for particle production and infection), hepatocellular carcinoma Huh7, HepG2, & Hep3B, colorectal adenocarcinoma Caco-2, glioma/glioblastoma (U-373)), African green monkey (kidney Vero & Cos-7), mouse fibroblast cells (NIH3T3), baby hamster kidney (BHK-21) cells, human-derived cells, for example, from a patient, including peripheral blood mononuclear cells (PBMCs), dendritic cells, skin fibroblasts, melanocytes, cardiomyocytes, neurons, astrocytes, hematopoietic stem cells (HSCs), and mesenchymal stem cells (MSCs). Said infected cells may be used in a method of treatment, for example, gene therapy such as ex vivo gene therapy, and in cancer immunotherapy and the treatment of genetic and/or infectious diseases.

Gene therapy, including ex vivo gene therapy offers many advantages, including precise control over gene modification, the ability to select and expand desired cells, and the potential for safer treatment due to the ability to verify the genetic material before reintroduction into the patient.

In particular, the cell-line has been carefully modified such that it is potentially safe for delivery within a patient, wherein the cell-line has potentially reduced capacity of generating replication-competent retroviruses with pathogenic potential.

The cell-line thus has the potential advantage of targeted treatment with increased safety and efficacy in mammals.

In one embodiment, the cell-line comprises lymphocytes, such as T cells, such as CD4+ T cells; or hematopoietic cells, such as hematopoietic stem cells (HSCs).

Lymphocytes comprised within the cell-line of the present invention, such as T cells, such as CD4+ T cells; or hematopoietic cells, such as HSCs are suitable for medical use, such as a method of treatment and method of gene therapy, such as ex vivo gene therapy. Thus, gene therapy approaches using said cell-line may comprise modified patient T cells or hematopoietic stem cells, which later differentiate into immune cells, suitable for autologous delivery within said patient.

Modified lymphocytes, particularly T cells and T cells derived from HSCs, offer significant advantages in treating diseases like cancer and viral infections. These advantages include enhanced specificity and targeting of specific cells, increased persistence within the body, and improved anti-tumor activity. Thus, lymphocytes comprised within the cell-line may possess such advantages and in addition, may possess a reduced capacity of generating replication-competent retroviruses with pathogenic potential for such cells, and therefore potentially possess favourable safety and efficacy profiles in mammals, such as humans.

In one or more embodiments, the cell-line comprises dividing or non-dividing cells.

In one or more embodiments, the cell-line comprises mammal-derived cells.

In one or more embodiments, the cell-line comprises one or more cells selected from the group consisting of: human cervical carcinoma cells, such as HeLa, human embryonic kidney cells, such as HEK293T, hepatocellular carcinoma cells, such as Huh7, HepG2 or Hep3B, colorectal adenocarcinoma cells such as Caco-2, glioma/glioblastoma cells such as U-373, African green monkey cells, such as kidney Vero or Cos-7, mouse fibroblast cells, such as NIH3T3, baby hamster kidney cells, such as BHK-21, human-derived cells, such as cells derived from a patient, such as peripheral blood mononuclear cells (PBMCs), dendritic cells, skin fibroblasts, melanocytes, cardiomyocytes, neurons, astrocytes, hematopoietic stem cells (HSCs), and/or mesenchymal stem cells (MSCs).

In one embodiment, the cell-line is obtainable by infection of a cell by the viral particle of the present invention.

In one embodiment, the cell-line is for use in gene therapy.

In one embodiment, the cell-line is for use in a method of treatment, comprising gene therapy.

In another embodiment, the cell-line is for use in ex vivo gene therapy.

In another embodiment, the cell-line is for use in a method of treatment, comprising ex vivo gene therapy.

Compositions and Kits

In a further aspect, the present invention relates to a composition comprising the recombinant viral vector, the expression plasmid, the viral particle, the producer cell, or the cell-line of the present invention.

In one embodiment, the present invention relates to a composition comprising the recombinant viral vector of the present invention. In one embodiment, the present invention relates to a composition comprising the expression plasmid of the present invention. In one embodiment, the present invention relates to a composition comprising the viral particle of the present invention. In one embodiment, the present invention relates to a composition comprising the producer cell of the present invention. In one embodiment, the present invention relates to a composition comprising the cell-line of the present invention.

In another aspect of the present invention, a pharmaceutical composition comprising the viral particle or the cell-line of the present invention, is disclosed. Thus, in one embodiment, the present invention relates to a pharmaceutical composition comprising the viral particle. In one embodiment, the present invention relates to a pharmaceutical composition comprising the cell-line. In one or more embodiments, the pharmaceutical composition may be provided in the form of an injection, such as an intravenous or a subcutaneous injection. In one embodiment, the pharmaceutical composition may be provided in a form suitable for "intranasal" delivery.

In another aspect of the present invention, a kit comprising the recombinant retroviral vector and/or the expression plasmid of the present invention, is disclosed. Thus, in one embodiment, the present invention relates to a kit comprising the recombinant retroviral vector and instructions for use. In one embodiment, the present invention relates to a kit comprising the expression plasmid and instructions for use. In one embodiment, the present invention relates to a kit comprising the recombinant retroviral vector, the expression plasmid and instructions for use.

Methods and Uses

In yet other aspects of the present invention, method of producing a viral particle, method of treatment, method of gene therapy, and uses of the recombinant retroviral vector, viral particle, producer cell, and/or cell-line of the present invention are disclosed.

Various disorders and diseases, such as immune disorders and diseases have been difficult to treat. For example, Severe Combined Immunodeficiency (SCID) is a rare, inherited disorder where the body's immune system is severely weakened or absent, making individuals highly susceptible to infections.

The recombinant retroviral vector, viral particle, and/or cell-line exhibits a potential ability to deliver effective and therapeutic gene delivery for the treatment of such disorders. The developed vector system produces virus particles that can stably transduce either dividing or non-dividing cells, such as hematopoietic stem cells, allowing repopulation of these cells upon replication, laying the groundwork for ex vivo applications, such as stem cell gene therapy.

Thus, in one embodiment, the recombinant viral vector of the present invention is for use in gene therapy, such as ex vivo gene therapy; cancer immunotherapy, such as breast cancer immunotherapy; treatment of genetic diseases; treatment of immune disorders, such as severe combined immunodeficiency (SCID); treatment of lung disorders, and/or treatment of infectious diseases. In another embodiment, the expression plasmid of the present invention is for use in gene therapy, such as ex vivo gene therapy; cancer immunotherapy, such as breast cancer immunotherapy; treatment of genetic diseases; treatment of immune disorders, such as severe combined immunodeficiency (SCID); treatment of lung disorders, and/or treatment of infectious diseases. In another embodiment, the viral particle of the present invention is for use in gene therapy, such as ex vivo gene therapy; cancer immunotherapy, such as breast cancer immunotherapy; treatment of genetic diseases; treatment of immune disorders, such as severe combined immunodeficiency (SCID); treatment of lung disorders, and/or treatment of infectious diseases. In another embodiment, the cell-line is for use in gene therapy, such as ex vivo gene therapy; cancer immunotherapy, such as breast cancer immunotherapy; treatment of genetic diseases; treatment of immune disorders, such as severe combined immunodeficiency (SCID); treatment of lung disorders and/or treatment of infectious diseases. In another embodiment, the composition is for use in gene therapy, such as ex vivo gene therapy; cancer immunotherapy, such as breast cancer immunotherapy; treatment of genetic diseases; treatment of immune disorders, such as severe combined immunodeficiency (SCID); treatment of lung disorders and/or treatment of infectious diseases. In another embodiment, the pharmaceutical composition is for use in gene therapy, such as ex vivo gene therapy; cancer immunotherapy, such as breast cancer immunotherapy; treatment of genetic diseases; treatment of immune disorders, such as severe combined immunodeficiency (SCID); treatment of lung disorders and/or treatment of infectious diseases. In another embodiment the kit is for use in gene therapy, such as ex vivo gene therapy; cancer immunotherapy, such as breast cancer immunotherapy; treatment of genetic diseases; treatment of immune disorders, such as severe combined immunodeficiency (SCID); treatment of lung disorders and/or treatment of infectious diseases. In one or more embodiments, the recombinant viral vector of the present invention is for use in diseases and/or disorders related to the brain, heart, lungs and/or muscle.

One aspect of the present invention describes a method of producing a viral particle, comprising the steps:

a. Introducing the recombinant viral vector of the present invention or the expression plasmid of the present invention to a cell, optionally wherein the cell is the producer cell of the present invention;
b. Extracting one or more viral particle(s) of the present invention from the cell of step a.

One aspect of the present invention describes a method of treatment, comprising the steps of:

a. Introducing the recombinant viral vector of the present invention or the expression plasmid of the present invention to a cell, optionally wherein the cell is the producer cell of the present invention;
b. Extracting one or more viral particle(s) of the present invention from the cell of step a;
c. Administering the viral particle(s) of step b. to a mammal in need of treatment, optionally wherein the mammal is a human.

In one embodiment, the method of treatment comprises gene therapy.

In one embodiment, the method of treatment is gene therapy.

One aspect of the present invention describes a method of treatment, comprising the steps of:

a. Introducing the recombinant viral vector of the present invention or the expression plasmid of the present invention to a cell, optionally wherein the cell is the producer cell of the present invention;
b. Extracting one or more viral particle(s) of the present invention from the cell of step a.;
c. Introducing the viral particle(s) of step b. to one or more cells in vitro to generate a cell-line of the present invention;
d. Optionally performing a selection for the cell-line in step c.;
e. Administering the cell-line of step c. or d. to a mammal in need of treatment, optionally wherein the mammal is a human.

SEQUENCES

TABLE 1

Table of sequences

| SEQ ID NO: | Description | Species | Sequence |
|---|---|---|---|
| 1 | WT mSD | *Mus musculus* | GCCTACGGAGAAGAGGTAGGTTACGGTGAGCCATTG GAAATG |
| 2 | mSD1 | Synthetic construct | GCCTGGGGAGAAGACCTAGGTTACGGTGAGCCATTG GAAATG |
| 3 | mSD2 | Synthetic construct | GCCAGGGGAGAAGAACCTGGTTACGGTGAGCCATTG GAAATG |
| 4 | eSA | Synthetic construct | AACTGTGCTTGTCGAGACAGAGAAGACTCTTGCGTTT CTGATAGGCACCTATTGGTCTTACTGACATCCACTTT GCCTTTCTCTCCACAGGTGTCCACTCC |
| 5 | eSD (with flanks) | Synthetic construct | CGTTAACACTAGTAAGCTTGCTCTAAGGTAAATAGTC GACAGGCCT |
| 6 | MMTV-LTR | Mus musculus | CCTAGGGGAGAAGCAGCCAAGGGGTTGTTTCCCACC AAGGACGACCCGTCTGCGCACAAACGGATGAGCCCA TCAGACAAAGACATATTCATTCTCTGCTGCAAACTTG GCATAGCTCTGCTTTGCTGGGGGCCATTGGGGGAAG TTGCGGTTCGTGCTCGCAGGGCTCTCACCCTTGACT CTTTTAATAGCTCTTCTGTGCAAGATTACAATCTAAAC AATTCGGAGAACTCGACCTTCCTCCTGAGGCAAGGA CCACAGCCAACTTCCTCTTACAAGCCGCATCGATTTT GTCCTTCAGAAATAGAAATAAGAATGCTTGCTAAAAAT TATATTTTTACCAATAAGACCAATCCAATAGGTAGATT ATTAGTTACTATGTTAAGAAATGAATCATTATCTTTTA GTACTATTTTTACTCAAATTCAGAAGTTAGAAATGGGA ATAGAAAATAGAAAGAGACGCTCAACCTCAATTGAAG AACAGGTGCAAGGACTATTGACCACAGGCCTAGAAG TAAAAAAGGGAAAAAAGAGTGTTTTTGTCAAAATAGG AGACAGGTGGTGGCAACCAGGGACTTATAGGGGACC TTACATCTACAGACCAACAGATGCCCCCTTACCATAT ACAGGAAGATATGACTTAAATTGGGATAGGTGGGTTA CAGTCAATGGCTATAAAGTGTTATATAGATCCCTCCC TTTTCGTGAAAGACTCGCCAGAGCTAGACCTCCTTGG TGTATGTTGTCTCAAGAAGAAAAAGACGACATGAAAC AACAGGTACATGATTATATTTATCTAGGAACAGGAAT GCACTTTTGGGGAAAGATTTTCCATACCAAGGAGGG GACAGTGGCTGGACTAATAGAACATTATTCTGCAAAA ACTTATGGCATGAGTTATTATGAATAGCCTTTATTGGC CCAACCTTGCGGTTCCCAAGGCTTAAGTAAGTTTTTG GTTACAAACTGTTCTTAAAACGAGGATGTGAGACAAG TGGTTTCCTGACTTGGTTTGGTATCAAAGGTTCTGAT |

TABLE 1-continued

Table of sequences

| SEQ ID NO: | Description | Species | Sequence |
|---|---|---|---|
| | | | CTGAGCTCTGAGTGTTCTATTTTCCTATGTTCTTTTGG<br>AATTTATCCAAATCTTATGTAAATGCTTATGTAAACCA<br>AGATATAAAAGAGTGCTGATTTTTTGAGTAAACTTGCA<br>ACAGTCCTAACATTCACCTCTTGTGTGTTTGTGTCTGT<br>TCGCCATCCCGTCTCCGCTCGTCACTTATCCTTCACT<br>TTCCAGAGGGTCCCCCCGCAGACCCCGGCGACCCT<br>CAGGTCGGCCGACTGCGGCAGCGGTACCC |
| 7 | TBLV-LTR | *Mus musculus* | CCTAGGGGAGAAGCAGCCAAGGGGTTGTTTCCCACC<br>AAGGACGACCCGTCTGCGCACAAACGGATGAGCCCA<br>TCAGACAAAGACATATTCATTCTCTGCTGCAAACTTG<br>GCATAGCTCTGCTTTGCCTGGGGCTATTGGGGGAAG<br>TTGCGGTTCGTGCTCGCAGGGCTCTCACCCTTGACT<br>CTTTTAATAGCTCTTCTGTGCAAGATTACAATCTAAAC<br>AATTCGGAGAACTCGACCTTCCTCCTGAGGCAAGGA<br>CCACAGCCAACTTCCTCTTACAAGCCGCATCGATTTT<br>GTCCTTCAGAAATAGAGATAAGAATGCTTGCTAAAAA<br>ATATATTTTTACCAATAAGACCAATCCAATAGGTAGAC<br>TATTAGTCACTATGTTAAGAAATGAATCATTATCTTTTA<br>GTACTATTTTTACTCAAATTCAGAAGTTAAAATGGAAA<br>TAGAAAATAGAAAGAGACGCTCAACCTCAGTTGAAGA<br>ACAGGTGCGGTTCCCAAGGCTTAAGTAGGTTTATGGT<br>TACAAACTGTTCTTACAGTTGAAGAACAGGTGCGGTT<br>CCCAAGGCTTAAGTAGGTTTATGGTTACAAACTGTTC<br>TTACAGTTGAAGAACAGGTGCGGTTCCCAAGGCTTAA<br>GTAAGTTTATGGTTACAAACTGTTCTTAAAACAAGGAT<br>GTGAGACAAGTGGTTTCCTGAGTTGGTTTGGTATCAA<br>ATGTTCTGATCTGAGCTCTGAGTGTTCTATTTTCCTAT<br>GTTCTTTTGGAATTTATCCAAATCTTATGTAAATGCTT<br>ATGTAAACCAAGATATAAAAGAGTGCTGATTTTTTGAG<br>TAAACTTGCAACAGTCCTAACATTCACCTCTTGTGTGT<br>TTGTGTCTGTTCGCCATCCCGTCTCCGCTCGTCACTT<br>ATCCTTCACTTTCCAGAGGGTCCCCCCGCAGACCCC<br>GGCGACCCTCAGGTCGGCCGACTGCGGCAGCGGTA<br>CCC |
| 8 | CTE | *Simian* | TGTGAGCTAGACTGGACAGCCAATGACGGGTAAGAG<br>AGTGACATTTCTCACTAACCTAAGACAGGAGGGCCGT<br>CAAAGCTACTGCCTAATCCAATGACGGGTAATAGTGA<br>CAAGAAATGTATCACTCCAACCTAAGACAGGCGCAG<br>CCTCCGAGGGATGTGTCTTTTGTTTTTTATAATTAAAA<br>AGGGTGACATGTCCGGAGCCGTGCTGCCCGGATGAT<br>GTCTTGGATCCGGCTAG |
| 9 | KOZAK consensus (R describes a purine, either A or G) | Unknown | GCCGCCRCC |
| 10 | Codon-optimized MMTV Gag/Dut-Pro/Pol-CTE gene | Synthetic construct | GCCGCCACC ATG GGT GTT TCT GGG TCA AAG GGC<br>CAA AAA CTT TTT GTC AGC GTA CTG CAG CGA CTC<br>TTG TCC GAG CGA GGG CTT CAC GTA AAA GAA AGC<br>TCA GCG ATT GAA TTC TAT CAG TTC CTC ATA AAA<br>GTT TCC CCC TGG TTC CCG GAG GAG GGA GGG<br>CTG AAT CTT CAA GAC TGG AAA CGA GTC GGT CGG<br>GAG ATG AAA CGA TAC GCA GCC GAG CAT GGA ACT<br>GAT AGC ATA CCC AAA CAA GCA TAC CCT ATT TGG<br>TTG CAA CTG CGG GAG ATA CTT ACA GAG CAG AGT<br>GAC CTG GTT CTC CTC AGC GCT GAG GCC AAA TCC<br>GTC ACC GAA GAA GAG CTC GAG GAG GGT TTG ACC<br>GGC CTG CTG TCA ACT TCT TCC CAG GAG AAA ACA<br>TAT GGT ACG AGG GGC ACA GCT TAC GCC GAG ATT<br>GAC ACC GAG GTT GAC AAA CTC AGT GAG CAC ATT<br>TAT GAT GAA CCC TAC GAA GAA AAA GAA AAG GCT<br>GAT AAG AAT GAG GAA AAG GAC CAT GTA AGG AAA<br>GTT AAA AAA ATA GTA CAG CGC AAA GAG ATA TCC<br>GAG GGC AAA CGA AAA GAA AAA GAC CAG AAA GCC<br>TTT CTG GCA ACG GAC TGG AAC GAT GAC GAC CTG<br>AGC CCT GAA GAC TGG GAT GAC CTG GAG GAG CAA<br>GCA GCC CAT TAC CAC GAC GAC GAT GAA CTG ATC<br>CTC CCG GTA AAG AGA AAG GTA GTT AAG AAG AAA<br>CCT CAG GCA CTG CGC CGA AAG CCG CTG CCA<br>CCG GTC GGA TTT GCC GGC GCA ATG GCT GAG<br>GCG AGA GAA AAG GGT GAC CTT ACT TTC ACA TTC |

TABLE 1-continued

Table of sequences

| SEQ ID NO: | Description | Species | Sequence |
|---|---|---|---|
| | | | CCG GTG GTA TTT ATG GGG GAA TCT GAC GAT GAT<br>GAC ACT CCT GTC TGG GAG CCC CTG CCT CTC AAG<br>ACC CTT AAG GAG TTG CAG CTC GCC GTT AAG ACT<br>ATG GGC CCT TCT GCG CCT TAT ACT TTG CAA GTA<br>GTG GAC ATG GTT GCA AGC CAG TGG CTC ACC CCG<br>AGT GAC TGG CAC CAA ACG GCG AGA GCT ACC CTC<br>TCC CCA GGA GAC TAT GTT TTG TGG CGG ACG GAG<br>TAC GAA GAG AAA AGT AAG GAG ACT GTA CAG AAA<br>GCC GCT GGA AAG AGG AAA GGG AAA GTC TCT TTG<br>GAT ATG TTG CTC GGA ACA GGT CAA TTT TTG AGC<br>CCA TCA TCT CAG ATA AAG CTC AGC AAA GAC GTG<br>TTG AAG GAC GTA ACA ACC AAC GCG GTT CTC GCA<br>TGG CGC GCA ATC CCA CCC CCA GGT GTG AAG AAG<br>ACG GTT TTG GOG GGC CTT AAA CAG GGA AAT GAA<br>GAA TCC TAC GAG ACT TTC ATA TCA CGA CTT GAA<br>GAG GCC GTA TAT CGC ATG ATG CCT CGC GGT GAA<br>GGA TCT GAC ATC CTC ATC AAG CAG CTG GCG TGG<br>GAA AAC GCT AAT TCC CTC TGT CAG GAC TTG ATT<br>AGG CCA ATT AGA AAG ACC GGC ACC ATC CAG GAT<br>TAT ATA CGA GCG TGC TTG GAT GCA TCT CCA GCA<br>GTC GTG CAA GGA ATG GCC TAC GCG GCA GCA ATG<br>CGA GGC CAA AAA TAC TCA ACC TTC GTG AAA CAA<br>ACA TAC GGA GGT GGG AAA GGT GGG CAA GGT TCA<br>GAA GGA CCC GTT TGC TTC AGC TGT GGA AAA ACG<br>GGG CAT ATA AAA AAA GAT TGC AAG GAG GAG AAA<br>GGG AGT AAG CGA GCC CCT TCC GGT CTG TGT CCT<br>AGG TGT AAA AAA GGG TAT CAC TGG AAG TCA GAG<br>TGC AAA TCT AAG TTT GAC AAG GAC GGA AAT CCT<br>CTT CCA CCC CTG GAG ACC AAT ACT GAA AAT TCA<br>AAA AAC TTG TAA AG GGC CAG AGC CCG TCA CCT<br>ACA CAG AAG GGA GAC GGG GTA AAA GGT TCC GGT<br>TTG AAT CCG GAA GCA CCA CCA TTT ACT ATA CAC<br>GAT TTG CCT AGG GGC ACT CCT GGG AGT GCG GGT<br>CTT GAC CTT TCT TCA CAA AAG GAC TTG ATC CTG<br>TCC CTT GAA GAT GGG GTT TCT TTG GTA CCC ACA<br>CTG GTC AAA GGT ACC TTG CCC GAG GGC ACA ACG<br>GGG CTG ATT ATA GGC AGA TCA TCA AAC TAC AAG<br>AAA GGA TTG GAA GTG CTG CCG GGC GTC ATA GAT<br>TCT GAC TTC CAA GGG GAA ATT AAG GTT ATG GTA<br>AAG GCC GCA AAA AAT GCA GTT ATA ATC CAC AAA<br>GGT GAA AGG ATC GCA CAG CTT CTG CTT CTG CCC<br>TAC TTG AAA CTC CCC AAC CCC ATC ATA AAA GAG<br>GAA CGA GGG AGT GAA GGA TTC GGG TCT ACT TCT<br>CAT GTT CAT TGG GTC CAG GAG ATT TCC GAC TCA<br>AGG CCC ATG TTG CAT ATT TCC TTG AAT GGA AGA<br>CGC TTC CTC GGG TTG CTT GAT ACG GGA GCT GAC<br>AAG ACC TGC ATA GCA GGT CGA GAC TGG CCA GCC<br>AAC TGG CCT ATA CAT CAA ACG GAG AGT TCA CTG<br>CAG GGT TTG GGC ATG GCA TGC GGT GTC GCA AGG<br>AGT TCA CAG CCT CTT CGA TGG CAA CAT GAG GAT<br>AAA AGC GGT ATT ATA CAC CCG TTC GTG ATT CCA<br>ACA TTG CCT TTC ACA CTG TGG GGC CGG GAC ATT<br>ATG AAA GAA ATT AAA GTG AGA CTT ATG ACC GAC<br>AGT CCT GAT GAT TCA CAG GAT TTA TGA TA GGC<br>GCC ATA GAA AGT AAC TTG TTT GCC GAC CAG ATT<br>TCT TGG AAA AGT GAC CAA CCG GTC TGG CTT AAT<br>CAA T TGG CCG CTC AAA CAA GAG AAG TTG CAA<br>GCG CTC CAA CAA CTC GTC ACA GAA CAG CTT CAG<br>CTT GGT CAT CTT GAG GAA TCC AAT TCT CCA TGG<br>AAC ACA CCG GTA TTC GTA ATA AAA AAA AAA TCA<br>GGT AAG TGG AGG CTT CTT CAA GAC TTG CGC GCC<br>GTC AAC GCT ACG ATG CAT GAC ATG GGG GCC CTG<br>CAG CCC GGC CTT CCA AGC CCA GTG GCT GTA CCA<br>AAG GGT TGG GAG ATA ATA ATT ATA GAC CTT CAG<br>GAC TGT TTT TTC AAC ATC AAA TTG CAC CCG GAG<br>GAT TGC AAG AGA TTT GCC TTT AGT GTT CCT AGC<br>CCG AAT TTC AAG AGA CCG TAT CAG CGA TTC CAG<br>TGG AAA GTG CTG CCC CAA GGA ATG AAA AAT TCT<br>CCA ACA CTC TGC CAA AAA TTC GTC GAC AAG GCA<br>ATC CTG ACG GTG CGC GAC AAG TAT CAA GAC TCC<br>TAC ATC GTC CAT TAT ATG GAT GAT ATT TTG CTC<br>GCT CAC CCC AGC CGA AGC ATA GTA GAC GAA ATA<br>CTC ACG AGC ATG ATC CAG GCC CTG AAT AAA CAC<br>GGA CTG GTC GTA AGT ACG GAG AAA ATT CAG AAG<br>TAT GAT AAT CTG AAA TAC CTT GGC ACG CAT ATT |

TABLE 1-continued

| SEQ ID NO: | Description | Species | Sequence |
|---|---|---|---|
| | | | CAA GGG GAC GTA GTT AGT TAC CAG AAG CTT CAG ATA CGA ACG GAT AAA CTG CGA ACT CTC AAC GAT TTC CAG AAG TTG CTG GGG AAT ATC AAT TGG ATA CGA CCT TTT CTC AAG CTC ACA ACT GGC GAA CTG AAG CCG TTG TTC GAA ATC CTT AAC GGC GAC AGT AAT CCC ATC TCC ATC CGC AAA CTC ACC CCT GAG GCC TGC AAG GCC TTG CAA TTG GTG AAT GAG CGA CTG AGC ATT GCG AGA GTA AAA AGA CTC GAT TTG AGC CGG CCA TGG AGT CTG TGT ATA TTG AAA ACG GAA TAT ACT CCA ACT GCA TGC TTG TGG CAG AAC GGC GTG CTG GAA TGG ATT CAT CTT CCC CAT ATT TCT CCC AAA GTT ATT ACG CCA TAT GAT ATA TTC TGC ACA CAA CTC ATT ATC AAA GGC CGA CAT AGG TCT AAG GAA CTG TTC AGT AAG GAC CCG GAT TAC ATT GTG GTC CCA TAC ACA AAG GTA CAG TTC GAT CTT CTT TTG CAA GAA AAG GAA GAT TGG CCG ATT TCC TTG TTG GGT TTC CTT GGG GAG GTA CAC TTT CAC CTT CCA AAA GAT CCC TTG CTT ACG TTT ACG CTT CAA ACG GCT ATC ATC TTT CCT CAT ATG ACC AGT ACG ACG CCC CTG GAG AAG GGA ATA GTC ATT TTC ACT GAT GGA AGT GCC AAT GGA AGA AGC GTG ACA TAT ATC CAG GGG CGA GAG CCA ATT ATC AAA GAG AAC ACG CAG AAT ACG GCT CAA CAG GCA GAG ATC GTG GCC GTT ATA ACA GCG TTT GAA GAG GTA AGT CAG AGC TTC AAT CTC TAC ACC GAC TCA AAG TAC GTT ACT GGG CTT TTC CCA GAA ATT GAA ACA GCG ACA CTT AGC CCC AGA ACC AAA ATA TAT ACA GAG CTC AGG CAT CTT CAA CGA CTG ATT CAC AAA CGA CAA GAG AAA TTC TAT ATT GGC CAT ATA AGG GGA CAT ACT GGC CTT CCT GGA CCC TTG GCG CAA GGC AAT GCT TAC GCG GAC TCA CTG ACT AGG ATC CTG ACT GCC TTG GAG AGT GCT CAG GAA AGT CAT GCA CTT CAT CAC CAA AAC GCA GCA GCT CTC CGA TTC CAA TTT CAT ATA ACG AGA GAG CAA GCC AGA GAG ATT GTA AAA CTG TGC CCT AAT TGC CCG GAT TGG GGT CAT GCT CCT CAA CTC GGA GTA AAT CCG AGG GGG TTG AAA CCA CGA GTT CTG TGG CAG ATG GAT GTA ACA CAC GTA AGC GAG TTC GGT AAG CTG AAG TAC GTA CAC GTT ACA GTT GAT ACC TAC AGC CAC TTC ACA TTC GCC ACT GCA CGA ACA GGA GAG GCC ACA AAA GAT GTG TTG CAG CAC TTG GCC CAA AGC TTC GCT TAC ATG GGA TTC CCA CAA AAG ATC AAG ACT GAC AAT GCA CCG GCA TAT GTA TCA CGC AGT ATC CAA GAG TTT CTC GCG CGG TGG AAA ATC TCT CAT GTG ACG GGC ATC CCC TAC AAT CCG CAG GGT CAA GCC ATT GTG GAG CGC ACT CAC CAG AAT ATT AAG GCT CAG CTG AAT AAA TTG CAG AAG GCT GGA AAG TAC TAT ACG CCA CAC CAC TTG CTG GCA CAT GCC CTT TTC GTA CTC AAT CAT GTG AAC ATG GAC AAC CAA GGA CAT ACC GCT GCA GAG CGA CAC TGG GGA CCG ATC AGC GCC GAT CCT AAA CCA ATG GTA ATG TGG AAA GAT CTT TTG GCG GGC AGC TGG AAG GGG CCG GAC GTC CTG ATC ACC GCC GGC CGA GGA TAT GCT TGC GTT TTC CCA CAA GAT GCG GAG ACT CCA ATA TGG GTG CCC GAT CGA TTC ATT AGA CCT TTT ACA GAG AGA AAA GAA GCT ACT CCA ACG CCG GGG ACT GCC GAA AAG ACT CCC CCT AGG GAC GAG AAG GAC CAG CAG AAG AGT CCT GAG GAT GAG TCC AGC CCA CAC CAG AGA GAG GAC GGA CTG GCG ACG TCA GCC GGA GTA AAC CTC AGG AGT GGA GGT GGA AGT TAA CCCCTGTGAGCTAGACTGGACAGCCAATGACGGGTA AGAGAGTGACATTTCTCACTAACCTAAGACAGGAGG GCCGTCAAAGCTACTGCCTAATCCAATGACGGGTAAT AGTGACAAGAAATGTATCACTCCAACCTAAGACAGGC GCAGCCTCCGAGGGATGTGTCTTTTGTTTTTTATAATT AAAAAGGGTGACATGTCCGGAGCCGTGCTGCCCGGA TGATGTCTTGG |
| 11 | VSV-G Env | Vesicular stomatitis virus | ATGAAGTGCCTTTTGTACTTAGCCTTTTTATTCATTGG GGTGAATTGCAAGTTCACCATAGTTTTTCCACACAAC CAAAAAGGAAACTGGAAAAATGTTCCTTCTAATTACC ATTATTGCCCGTCAAGCTCAGATTTAAATTGGCATAAT GACTTAATAGGCACAGCCTTACAAGTCAAAATGCCCA AGAGTCACAAGGCTATTCAAGCAGACGGTTGGATGT |

TABLE 1-continued

| Table of sequences | | | |
|---|---|---|---|
| SEQ ID NO: | Description | Species | Sequence |
| | | | GTCATGCTTCCAAATGGGTCACTACTTGTGATTTCCG CTGGTATGGACCGAAGTATATAACACATTCCATCCGA TCCTTCACTCCATCTGTAGAACAATGCAAGGAAAGCA TTGAACAAACGAAACAAGGAACTTGGCTGAATCCAGG CTTCCCTCCTCAAAGTTGTGGATATGCAACTGTGACG GATGCCGAAGCAGTGATTGTCCAGGTGACTCCTCAC CATGTGCTGGTTGATGAATACACAGGAGAATGGGTT GATTCACAGTTCATCAACGGAAAATGCAGCAATTACA TATGCCCCACTGTCCATAACTCTACAACCTGGCATTC TGACTATAAGGTCAAAGGGCTATGTGATTCTAACCTC ATTTCCATGGACATCACCTTCTTCTCAGAGGACGGAG AGCTATCATCCCTGGGAAAGGAGGGCACAGGGTTCA GAAGTAACTACTTTGCTTATGAAACTGGAGGCAAGGC CTGCAAAATGCAATACTGCAAGCATTGGGGAGTCAG ACTCCCATCAGGTGTCTGGTTCGAGATGGCTGATAA GGATCTCTTTGCTGCAGCCAGATTCCCTGAATGCCCA GAAGGGTCAAGTATCTCTGCTCCATCTCAGACCTCAG TGGATGTAAGTCTAATTCAGGACGTTGAGAGGATCTT GGATTATTCCCTCTGCCAAGAAACCTGGAGCAAAATC AGAGCGGGTCTTCCAATCTCTCCAGTGGATCTCAGCT ATCTTGCTCCTAAAAACCCAGGAACCGGTCCTGCTTT CACCATAATCAATGGTACCCTAAAATACTTTGAGACC AGATACATCAGAGTCGATATTGCTGCTCCAATCCTCT CAAGAATGGTCGGAATGATCAGTGGAACTACCACAG AAAGGGAACTGTGGGATGACTGGGCACCATATGAAG ACGTGGAAATTGGACCCAATGGAGTTCTGAGGACCA GTTCAGGATATAAGTTTCCTTTATACATGATTGGACAT GGTATGTTGGACTCCGATCTTCATCTTAGCTCAAAGG CTCAGGTGTTCGAACATCCTCACATTCAAGACGCTGC TTCGCAACTTCCTGATGATGAGAGTTTATTTTTTGGTG ATACTGGGCTATCCAAAAATCCAATCGAGCTTGTAGA AGGTTGGTTCAGTAGTTGGAAAAGCTCTATTGCCTCT TTTTTCTTTATCATAGGGTTAATCATTGGACTATTCTT GGTTCTCCGAGTTGGTATCCATCTTTGCATTAAATTAA AGCACACCAAGAAAAGACAGATTTATACAGACATAGA GATGAACCGACTTGGAAAGTAA |

TABLE 2

| List of primers | | | | |
|---|---|---|---|---|
| SEQ ID NO: | Primer Name | Primer Sequence- Direction | Target | Purpose/ Reference |
| 12 | OFM330 | CAATTGTTCCAGGAACCAGG- Reverse | pG3LC | Firefly luciferase nt 381-400 |
| 13 | OFM600 | GATACCGCTCGCCGC- Reverse | DA024 | Sequencing of SIN vectors |
| 14 | OFM622 | AGGCCTGTCGACTATTTACCTTAG AGCAAGCTTACTAGTGTTAACGCA CTCTTTTATATCTTGG- Reverse | SV40- splice donor | Substitution of SV40 eSD at the end of U3 of 3'LTR with 5' and 3' flanks |
| 15 | OFM623 | CGTTAACACTAGTAAGCTTGCTCT AAGGTAAATAGTCGACAG GCC TCTGATTTTTTGAGTAAAC- Forward | SV40- splice donor | Substitution of SV40 eSD at the end of U3 of 3'LTR with 5' and 3' flanks |
| 16 | OFM624 | GACTATTTACCTTAGAGCAAGCAC TCTTTTATATCTTGG- Reverse | SV40 splice donor | Substitution of SV40 eSD at the end of U3 of 3'LTR with 5' and 3' flanks |

TABLE 2-continued

List of primers

| SEQ ID NO: | Primer Name | Primer Sequence- Direction | Target | Purpose/ Reference |
|---|---|---|---|---|
| 17 | OFM625 | CTT GCT CTA AGG TAA ATA GTC CTG ATT TTT TGA GTA AAC-Forward | SV40 splice donor | Substitution of SV40 eSD at the end of U3 of 3'LTR with 5' and 3' flanks |
| 18 | OFM626 | CTCAGGTCGGCCGACTGC-Forward | HYBMTV U5 | JA010 packaging signal deletion clones |
| 19 | OFM642 | GCCCCGAATTCATGCATATGGTG-Forward | PCI vector | Insertion of eSA branch sequence from PCI vector |
| 20 | OFM643 | GACGAGCTGTACAAGTAAGAAGA CTCTTGCGTTTCTGATAGGCACCT ATTGGTCTTACTGACATCCA-Reverse | PCI vector | Insertion of eSA branch sequence from PCI vector |
| 21 | OFM644 | GAAGACTCTTGCGTTTCTGATAGG CACCTATTGGTCTTACTGACATCC ACTTTGCCTTTCTCTCCACAGGTG-Forward | PCI vector | Insertion of eSA branch sequence from PCI vector |
| 22 | OFM645 | GGAGGCCTAGGCTTTTGC-Reverse | PCI vector | Insertion of eSA branch sequence from PCI vector |
| 23 | OFM652 | CGTTAACACTAGTAAGCTTGCTCT AAGGTAAATAGTCGACAGGCCTTT CACCTCTTGTGTGTTTGTG-Forward | SV40 eSD | SV40 eSD inner primers for insertion between end of R and start of U5 |
| 24 | OTR554 | CAGGGTACCGCTGCCGCAGTCGG CCGACC- Reverse | HYB-MTV | HYB MTV nt 9877-9857 3' U5 end |
| 25 | OTR606 | CCACTAGTGAGTTG GGACAAGATGTG- Forward | HYB-MTV | MMTV nt 8111-8129 of env |
| 26 | OTR643 | CCTCTAGATGCGAA GAGCCTTGACCAAG- Forward | HYB-MTV | MMTV nt 8482-8501 3' LTR |
| 27 | OTR650 | CCTCTAGACCAACC TTGCGGTTCCCAAG-Forward | HYB-MTV | MMTV nt 9521-9532 poly A |
| 28 | OTR977 | GTTTAACCGGACTAC TATCGACAAGTTC- Forward | HYB-MTV | HYB-MTV nt1828-1855 |

EXAMPLES

Materials

- Restriction endonucleases (New England Biolabs or Promega, USA)
- Phusion Hi-Fidelity DNA polymerase (Thermo Fisher Scientific, USA)
- Agarose gels (Thermo Fisher Scientific, USA)
- DNA Polymerase I (Klenow Large Fragment) (New England Biolabs, USA)
- T4 DNA Polymerase (New England Biolabs or Promega, USA)
- Calf intestinal phosphatase (New England Biolabs or Promega, USA)
- Qiaquick Gel Extraction kit (Qiagen, USA)
- Quick T4 DNA ligase (New England Biolabs or Promega, USA)
- LB broth (Merck, USA)
- Calcium chloride (Merck, USA)
- Glycerol (Merck, USA)
- *Escherichia coli* (*E. coli*) strains: DH5 alpha (New England Biolabs, USA), STBL2 (New England Biolabs, USA), and JM109 (New England Biolabs, USA)
- Luria Bertani (LB) broth (HiMEDIA, India)
- Ampicillin (Merck, USA)
- Kanamycin (Merck, USA)
- Chloramphenicol (Merck, USA)
- Qiagen Maxi Plasmid Purification kit (Qiagen)
- Isopropanol (Merck, USA)
- Ethanol (Merck, USA)

pCI (Promega, USA)
Dulbecco's Modified Eagle's Medium (DMEM) (Hyclone, USA)
Fetal bovine serum (FBS) (Hyclone, USA)
1% penicillin and streptomycin (Thermo Fisher Scientific, USA)
0.1% gentamycin (50 mg/ml w/v solution) (Thermo Fisher Scientific, USA)
HEPES-buffered saline (HBS) (Merck, USA)
Phosphate-buffered saline (Hyclone, USA)
Dexamethasone (Merck, USA)
Hygromycin antibiotic containing media (Merck, USA)
TNE buffer (Thermo Fisher Scientific, USA)
TRizol reagent (Thermo Fisher Scientific, USA)
DEAE-dextran sulfate (Merck, USA)
Trypsin EDTA (Gibco or Hyclone, USA)
Passive Lysis Buffer (Promega, USA)
Luciferase Assay Reagent II (LAR II) (Promega, USA)
Chloroform (Merck, USA)
Recombinant RNasin (Promega, USA)
Turbo DNase Inactivation Reagent (Thermo Fisher scientific, USA)
Moloney Murine Leukemia Virus Reverse Transcriptase (M-MLV RT) (Thermo Fisher Scientific, USA)
RNase inhibitor (Promega, USA)
Radioimmunoprecipitation assay (RIPA) buffer (Merck, USA)
β-mercaptoethanol (Merck, USA)
Phenylmethylsulfonyl fluoride (PMSF) (Merck, USA)
SDS—loading buffer (Merck, USA)
Bradford reagent (BioRad, USA)
SDS polyacrylamide gels (Merck, USA)
Acrylamide (Merck, USA)
Bis-acrylamide (Merck, USA)
Protran BA85 nitrocellulose membranes (GE Healthcare, USA)
1×PBS with 0.1% Tween-20 (PBST) (GE Healthcare, USA)
anti-MMTV Gag/Pol (anti-MTV p27) (Prof. Susan Ross, The University of Chicago, IL, USA)
envelope protein, anti-gp52 (Prof. Jaquelin P. Dudley, The University of Texas at Austin, TX, USA)
Luc antibody (Merck, USA)
Monoclonal anti-β-actin peroxidase antibody (A3854) produced in mice (Merck, USA)
HRP conjugated anti-mouse and anti-goat secondary antibodies (Merck, USA)
D-luciferin (Thermo Fisher Scientific, USA)
Isofluorane (Merck, USA)

Some Abbreviations Used:

BSA: Bovin Serum Albumin
dNTP: Deoxynucleoside triphosphastes
RT: room temperature
CIP: calf intestinal phosphatase
LB broth: Luria Bertani broth
Tris-Cl: Tris (hydroxymethyl)aminomethane hydrochloride
EDTA: ethylenediaminetetraacetic acid
SDS: sodium dodecyl sulfate
WT: wild type
PMSF: phenylmethylsulfonyl fluoride
DMEM: Dulbecco's Modified Eagle's Medium
FBS: fetal bovine serum
HBS: HEPES-buffered saline
PBS: phosphate-buffered saline
DEAE: diethylaminoethyl
RIPA: radioimmunoprecipitation
SNC: Substantia Nigra pars compacta The abbreviation 'aX' denotes the dilution factor wherein 'a' indicates the extent of dilution, e.g., 1× denotes a dilution factor of 1, 2× denotes a dilution factor of 2, etc.

Example 1: Preparation of Materials

Methods

Construction of Plasmids

The pre-existing plasmids from the MMTV trans-complementation assays were modified using various cloning strategies described below herein. These modifications afforded the next generation of MMTV-based vectors. The cloning strategies described below herein provided two types of self-inactivating transfer plasmids to generate self-inactivating viral vectors using producer cells for transduction of target cells.

Preparation of DNA Fragments for Cloning

For restriction digestion, 1-2 μg of plasmid was digested with 10 units of required restriction endonucleases in 1× compatible buffer (provided by manufacturer) supplemented with 0.1 mg/ml BSA in a final volume of 20 μl. All enzymatic reactions were performed at optimum temperature for enzymatic activity in water bath or thermomixer for 1 to 2 hours.

PCR Amplification of Fragments for Sub-Cloning

The spliced-overlap extension (SOE) PCR strategy, as described in Gibbs et al., 1994 was mainly used to amplify PCR fragments for cloning using Phusion Hi-Fidelity DNA polymerase for up to 20 cycles with optimum primer annealing temperature ranging from 50-65° C., depending upon the primer. For each PCR reaction, 100 ng DNA template, 1 M of specific primer, 200 M each dNTP, 1.25 unites Phusion polymerase, and 1× Phusion polymerase buffer (provided by Thermo Fisher Scientific USA)) in a total 50 μl volume was added. Initial denaturation at 98° C. for 30 seconds, followed by 20 amplification cycles consisting of denaturation at 98° C. for 10 seconds, primer annealing at 55-62° C. for 30 seconds, extension at 72° C. for 30 seconds/kb, and final extension was set at 72° C. for 5 minutes. The resulting PCR products were analyzed by electrophoresis on 0.8-2% agarose gels, stained with ethidium bromide, and visualized using a gel documentation system (UVP BioSpectrum 610 Imaging System).

Plasmid End Preparation for Blunt or Sticky End Ligations (i) Filling of 5' Single-Stranded DNA Overhangs The restriction digested plasmid DNA fragments required for blunt end cloning was used to fill 5' overhangs using the 5'-3' polymerase activity of DNA Polymerase I (Klenow Large Fragment) in 1×DNA Polymerase I buffer supplemented with 0.1 mg/ml BSA, and M of all four dNTPs in 20 μl for 15 minutes at RT.

(ii) Exonuclease Removal of 3' Single-Stranded DNA Overhangs

The restriction digested ends of fragments were digested to remove 3' overhangs in 1 μg digested DNA using the 3'-5' exonuclease activity of 10 units of T4 DNA Polymerase in 1×T4 DNA Polymerase buffer (provided by, New England Biolabs, USA) supplemented with 0.1 mg/ml BSA, and 100 M of all four dNTPs in a total volume of 20 μl for 15 minutes at 37° C.

(iii) Dephosphorylation of 5' End of Backbone

1 μg of restriction digested linearized DNA backbones generating sticky ends were end modified to remove 5' phosphate using CIP for dephosphorylation with 1 unit of CIP in 1×CIP buffer (provided by the enzyme manufacturer) in a total volume of 20 μl for 60 minutes at 37° C.

(iv) Agarose Gel Electrophoresis and Gel Purification

The DNA fragments were size-fractionated on agarose gels (0.8-2.5%) via electrophoresis. The desired DNA bands were excised from the gel using a scalpel using handheld UV lamp with long wavelength and purified using the Qiaquick Gel Extraction kit. The kit protocol involved the steps to dissolve agarose gel matrix using salt solution and reversible DNA binding to a silica filter to purify the DNA from impurities and finally elute the required DNA fragment in water for downstream cloning steps.

(v) Ligations 50-100 ng of restriction digested and end modified plasmid backbones were ligated to insert DNA in a 1:3 or 1:7 molar ratio using 10 unites of Quick T4 DNA ligase and 1× Quick T4 DNA ligase buffer (provided by the enzyme manufacturer) in a 20 μl of reaction volume. Ligation of sticky ends was performed for 15 minutes at RT while blunt end ligation was performed at 16° C. overnight. The ligation reactions were subsequently transformed into competent bacterial cells to recover successful constructs.

Preparation of Competent Cells

The bacterial cells used for transformation of plasmids were chemically treated with $CaCl_2$ to make them competent to take up plasmid DNA. A 10 ml pre-inoculum culture of LB broth was made by inoculation with a single colony of the correct clone and shaken at 37° C. overnight at 200 rpm. Overnight grown culture was used to inoculate 200 ml of LB broth (autoclaved) and culture was shaken at 18° C. to an OD600 of 0.8 (logarithmic growth phase). The culture was split into centrifuged tubes to be chilled on ice for 15 minutes and centrifuged at 6000 rpm for 10 minutes at 4° C. to pellet the cells. The bacterial cell pellets were gently resuspended in 80 ml of 100 mM $CaCl_2$ (pH6.7), chilled on ice before use, and centrifuged as before. The pellets were resuspended in 10 ml of 100 mM $CaCl_2$ supplemented with 15% glycerol, and chilled on ice for 10 mins. Aliquots containing 100 μl of competent cells were snap frozen in liquid nitrogen and stored at −80° C. for later use.

Transformation of *E. coli*

*Escherichia coli* (*E. coli*) strains DH5 alpha, STBL2, and JM109 were used in this study for. transformation and cloning. These strains were grown in LB broth (1% bacto-tryptone, 0.5% yeast extract, 1% NaCl) with shaking at 300 rpm or streaked on LB agar plates and maintained at 37° C. for selection and making master stocks. Ampicillin was used as selection in LB broth or agar at a concentration 200 μg/ml for screening antibiotic resistant (plasmid containing) clones. After confirmation of positive clones through sequencing, bacterial cultures containing the correct plasmids were stored at −80° C. in LB broth containing 15% (v/v) glycerol.

Large Scale Preparation of Plasmid DNAs

Large-scale preparation of plasmid DNAs were carried out using Qiagen Maxi columns, employing the alkaline lysis method, as outlined in the Sambrook Manual. A single colony of transformed *Escherichia coli* DH5a was selected to establish a pre-inoculum in either 10 or 25 ml of Luria Bertani (LB) broth. The LB media was supplemented with appropriate antibiotics, either Ampicillin or Kanamycin, at a working concentration of 2000 μg/ml or 100 μg/ml, respectively. These cultures were subjected to overnight shaking at 37° C. in an appropriate incubator. For high copy number plasmids, a 10-ml overnight culture was added to 100 ml of fresh LB media with antibiotics in 500 ml Erlenmeyer flasks and grown overnight at 37° C. with shaking. For low-copy number plasmids, a 25 ml pre-inoculum was added to 500 ml freshly autoclaved LB media with the corresponding antibiotics.

For low copy plasmids, the cultures were allowed to grow at 37° C. with shaking in 2-liter flasks until they reached an OD at A600 value of 0.9-1.2. Plasmid amplification was then initiated by adding chloramphenicol (34 mg/ml stock solution prepared in ethanol) to a working concentration of 170 μg/ml. The cultures were further grown for 16 hours with shaking until ready for plasmid isolation.

Bacterial cell pellets were harvested the following day by centrifugation using an Avanti J-26 XPI centrifuge from Beckman Coulter at 6000 rpm (JA10 rotor, Beckman Coulter USA) for 10 minutes at 4° C. These pellets were then resuspended in Qiagen P1 Buffer, which contains 50 mM Tris-Cl pH 8.0, 10 mM EDTA, and 100 μg/ml RNase A, all kept on ice. To achieve lysis, the suspension was transferred to 50 ml tubes, lysed in P2 Buffer (containing 200 mM NaOH and 1% SDS w/v). The mixture was thoroughly mixed by inverting the tubes to ensure efficient lysis and incubated at room temperature for 5 minutes. Neutralization was achieved by adding P3 Buffer (3.0 M potassium acetate, pH 5.5) with the tube being inverted several times, followed by incubation on ice for 20 minutes. The precipitated lysate was then spun by centrifugation (rotor JA25.50, Beckman Coulter) at 9000 rpm for 40 minutes at 4° C. to remove protein debris.

Meanwhile, Qiagen-tips 500 were equilibrated by adding an appropriate volume of QBT Buffer and allowed to run by gravity flow. The cleared lysates were carefully poured onto the equilibrated columns, leaving the cellular debris at the tube's bottom. The mixtures were allowed to flow by gravity to enable plasmid DNAs to bind to the column. After washing the tips twice with QC buffer, the column-bound plasmid DNAs were eluted using QF Buffer. Next, plasmid DNAs were concentrated by adding 0.7× the volume of room-temperature isopropanol. After thorough mixing, they were centrifuged (Allerga X15R centrifuge, Beckman Coulter) at 3,500 rpm for 30 minutes at 4° C. The precipitated DNA pellets were washed once with 5 ml of 70% ethanol, spun as before, and air-dried. Finally, the dried plasmid DNA pellets were resuspended in 400 μl of Tris-EDTA buffer, pH 8.0, and the quality of plasmid DNA was assessed by measuring its absorbance at 260 and 280 nm UV wavelengths using a NanoDrop 2000C Spectrophotometer (Thermo Fisher Scientific). The plasmid DNAs were stored at 4° C. for short-term or −20° C. for long-term storage.

Cloning Details

Details of the cloning of the vectors are described below herein. The design of the vectors and expression plasmids developed were verified by restriction enzyme digestion followed by sequencing. The list of primers used, and the constructs made are summarized in Table 2 above and Table 3 below herein.

TABLE 3

Summary of transfer vectors

| Construct Name | Sub/Final Clone | Construct Description |
|---|---|---|
| SQ034 | Final- MMTV WT | LUC 3' MMTV LTR |
| SQ035 | Final- TBLV WT | LUC-3' TBLV LTR |
| SQ064 | Modified Intermediate-split intron SIN | eSD insertion between R-U5 SQ034 backbone (MMTV-LTR-based) |

TABLE 3-continued

Summary of transfer vectors

| Construct Name | Sub/Final Clone | Construct Description |
|---|---|---|
| SQ065 | Modified Intermediate-split intron SIN | eSD insertion between R-U5 SQ035 backbone (TBLV-LTR-based) |
| SQ066 | Modified Intermediate-split intron SIN | eSD insertion at the end of U3 SQ034 backbone (MMTV-LTR-based) |
| SQ067 | Modified Intermediate-split intron SIN | eSD insertion at the end of U3 SQ035 backbone (TBLV-LTR-based) |
| SQ068 | Modified Intermediate-split intron SIN | Mutated 5' retroviral mSD1; inserted eSA SQ034 backbone (MMTV-LTR-based) |
| SQ069 | Modified Intermediate-split intron SIN | Mutated 5' retroviral mSD2; inserted eSA SQ034 backbone (MMTV-LTR-based) |
| SQ070 | Modified Intermediate-split intron SIN | Mutated 5' retroviral mSD1; inserted eSA SQ035 backbone (TBLV-LTR-based) |
| SQ071 | Modified Intermediate-split intron SIN | Mutated 5' retroviral mSD2; inserted eSA SQ035 backbone (TBLV-LTR-based) |
| SQ072 | Modified Final Split Intron SIN Vector | Mutated 5' retroviral mSD1; inserted eSA eSD insertion between R-U5 SQ034 backbone (MMTV-LTR-based) |
| SQ073 | Modified Final Split Intron SIN Vector | Mutated 5' retroviral mSD1; inserted eSA eSD insertion between R-U5 SQ035 backbone (TBLV-LTR-based) |
| SQ074 | Modified Final Split Intron SIN Vector | Mutated 5' retroviral mSD1; inserted eSA eSD insertion at the end of U3 SQ034 backbone (MMTV-LTR-based) |
| SQ075 | Modified Final Split Intron SIN Vector | Mutated 5' retroviral mSD1; inserted eSA eSD insertion at the end of U3 SQ035 backbone (TBLV-LTR-based) |
| SQ076 | Modified Final Split Intron SIN Vector | Mutated 5' retroviral mSD2; inserted eSA eSD insertion between R-U5 SQ034 backbone (MMTV-LTR-based) |
| SQ077 | Modified Final Split Intron SIN Vector | Mutated 5' retroviral mSD2; inserted eSA eSD insertion between R-U5 SQ035 backbone (TBLV-LTR-based) |
| SQ078 | Modified Final Split Intron SIN Vector | Mutated 5' retroviral mSD2; inserted eSA eSD insertion at the end of U3 SQ034 backbone (MMTV-LTR-based) |
| SQ079 | Modified Final Split Intron SIN Vector | Mutated 5' retroviral mSD2; inserted eSA eSD insertion at the end of U3 SQ035 backbone (TBLV-LTR-based) |

(i) SQ034 and SQ035

These vectors were created by replacing the SV hygromycin resistance gene cassette in the classical MMTV transfer vector, DA024, with the SV firefly luciferase (Luc) gene cassette. The NheI-XbaI fragment containing SV-luciferase was obtained from pGL3C and subcloned into PP68 plasmid upstream of the MPMV CTE sequence through directional cloning, resulting in subclone PP68-Luc.

Next, the NheI cassette containing SV-Luc-CTE was removed from subclone PP68-Luc to replace the NheI cassette of SV-Hygro-CTE in DA024, resulting in the clone named SQ034. We also modified SQ034 to create SQ035 in which the 3' LTR of MMTV was replaced with TBLV, a MMTV strain which is highly active in T lymphocytes.

SQ034 and SQ035 are considered to be the 'wild-type' or 'parent' constructs of the invention.

(ii) SQ064 to SQ067

To remove the eGFP and insert new mutations in the mSD, the split intron vectors were reengineered as follows herein. First, the eukaryotic splice donor (eSD) sequence was inserted at the end of U3 of the 3' LTR in SQ034 and SQ035 backbone through SOE PCR. Primer pairs OTR643/OFM 622 and OFM623/OFM 554 were used to amplify fragment A (~1236 nt) and fragment B (~160 nt), respectively. The sequence and fragment size details are shown in Table 2. Additionally, the eukaryotic splice donor (eSD) sequence was also inserted near R and start of U5 in the 3' LTR of SQ034 and SQ035 plasmid backbone through SOE PCR. The primer pairs OTR 643/OFM653 and OFM 652/OFM 554 were used to amplify fragment C and fragment D, respectively, using the Phusion Hi-Fidelity DNA polymerase.

After successful amplification and gel purification of fragments, outer primer set OTR643/OTR554 was used to amplify second round PCR products (~1396 nt) by using gel purified and combined fragments from first PCR round as template. The PCR products from second round containing insertion of eSD (~69 nt) were digested with AvrII and KpnI and resulting fragments were gel purified for directional cloning into SQ034 and SQ035 backbones. Insertion of eSD in SQ034 and SQ035 was confirmed in R-U5 of resulting plasmids, named SQ064 and SQ065, and at the end of U3 of resulting plasmids (SQ066 and SQ067 respectively), through restriction digestion and sequencing.

(iii) SQ068 to SQ071

The suboptimal retroviral major mSD present downstream of the 5' LTR was also mutated to prevent pre-mature splicing of packaging signal from transfer RNA in packaging cell line upon insertion of eSA. Mutation of mSD and insertion of eSA after the packaging signal (downstream to 400 bp of gag) was completed simultaneously using synthetic g-block sequences containing BstEII and SmaI restriction sites. Two types of g-blocks were custom-designed and synthesized from Macrogen, Korea to incorporate two different sets of mutations in mSD (mSD1 and mSD2) which showed stable structural dynamics of RNA secondary structure using the online in-silico MFold tool. The backbones of SQ034 and SQ035 were prepared by sequential digestion using BstEII and SmaI restriction enzymes and g-blocks were cloned directionally. The final plasmids showing the successful mutation of either mSD1 or mSD2 along with eSA insertion in SQ034 backbone were named as SQ068 and SQ069. The same mSD1 and mSD2 mutations along with eSA insertion carrying g-blocks cloned in SQ035 backbone were named, SQ070 and SQ071, respectively.

(iv) SQ072 to SQ079

To construct the modified final split intron vectors, SQ064, SQ065, SQ066 and SQ067 vectors were used as backbones to replace the sequences between BstEII and SmaI with G-blocks containing the new mutations of the mSD as well as insertion of eSA. The G-blocks with these mutations were synthesized using Macrogen gene synthesis service and cloned into SQ034 (WT) backbone which does not contain eGFP sequences to prevent any potential down-regulation of transgene expression previously observed in split intron SIN vectors. The consensus splice acceptor (eSA) branchpoint sequence was inserted downstream of 400 bp of gag gene in the same G-blocks for simultaneous insertion of eSA sequence derived from sequence 899 to 992 of pCI. The original retroviral mSD present in the 5' UTR of the viral genome was mutated to prevent any pre-mature splicing in the producer cells and to ensure availability of packageable transgene transcripts because of the presence of inserted eSA downstream to 400 bp of gag. The final SIN transfer vectors were named SQ072, SQ073, SQ074 and SQ075 for vectors with mSD1 mutation with eSA insertion and SQ076, SQ077, SQ078, SQ079 for mSD2 mutation and eSA insertion.

Mammalian Cell Lines

Two cell lines, human embryonic kidney (HEK) 293T cells and HeLa T4 cells were mainly used in this study. HEK 293T cells were used for the transient transfections of the three plasmids for the generation of viral particles, while human HeLa T4 cells were used for the transduction and expression studies. The cell lines were maintained in Dulbecco's Modified Eagle's Medium (DMEM) supplemented with 10% heat inactivated fetal bovine serum (FBS). The FBS was heat inactivated by placing for 1 hour at 55° C. Furthermore, 1% penicillin and streptomycin, and 0.1% gentamycin (50 mg/ml w/v solution) were added in all media. The lines were maintained at 37° C. and 5% $CO_2$ level in a water jacketed incubator (Forma series II, Thermo Fisher Scientific) set with humidity.

Transient Transfection of MMTV Plasmids

The transfection of HEK 293T cells was performed using the classical calcium phosphate method of DNA transfection (Graham and van der Eb 1973a). The MMTV-based plasmids were transiently transfected in these cells using the Invitrogen $CaPO_4$ precipitation kit. Briefly, 0.5×106 HEK 293T cells were plated in 6-well plates for 16-24 hours in 3 ml of complete DMEM media. The three-plasmid cocktail, including relevant transfer (6 μg/well), packaging (6 μg/well) and envelop plasmids (6 μg/well) were prepared in 1.8 ml microcentrifuge tubes and the final volume was adjusted to 60 μl with nuclease-free $H_2O$. The DNA cocktail buffer (525 μl for 6 wells) was prepared by combining nuclease-free water (67 μl per well), 2M $CaCl_2$ (10.5 μl per well), and pre-mixed DNAs (60 μl per well). This DNA cocktail mixture was added dropwise to a 4-ml snap cap tube containing 525 μl of 2×HEPES-buffered saline (HBS) while continuously bubbling the mixture. After briefly vortexing, the mixture was incubated at room temperature for 30 minutes. Following this incubation period, the mixture was added to the cells drop-by-drop with gentle shaking. Approximately 24 hours post-transfection, the cells were thoroughly washed with phosphate-buffered saline (1×PBS) in order to eliminate any DNA precipitates, after which fresh media was added. The transfected cells were then harvested 72 hours post-transfection for estimating transfection efficiency, while supernatants containing virus particles were collected for infection of target cells. Cells that were transfected with MMTV WT or SIN transfer plasmid were induced by 10-6M dexamethasone 24 hours after transfection, as described previously (Salmons et al., 1989).

For large scale virus production for test in mice, multiple 6-well plates were transfected with each plasmid, and the supernatants harvested were pre-cleared and ultracentrifuged on sucrose gradients for concentration purposes, as described previously (Mustafa et al., 2018). The resulting virion pellets were resuspended in PBS and the titers determine by infecting a small proportion on HeLaT4 cells. The remaining pelleted virions were frozen in 100 μl aliquots at −80° C., till further use.

Generation of Stable Packaging Cell Line

The SQ048 plasmid was co-transfected with pTREG 3G plasmid in 293Tet-ON cells as per manufacturer's (Takara Bio, USA) instructions. After 2-3 days of transient transfection, the stable Gag/Pol expressing cells were selected using 0.8 mg/ml of hygromycin antibiotic containing media for 2-3 weeks. Periodically, dead cells were removed by slow speed centrifugation until the stable cell culture survived.

Virus Harvesting and Concentration

To remove cellular debris, supernatants from transfected cultures were centrifuged at 4000 rpm for 10 minutes. Next, the clarified supernatant was filtered using 0.2-micron syringe filters and pelleted by ultracentrifugation using the SW28 rotor at 24,000 rpm for 2 hours at 4° C. TNE buffer 40 (50 mM Tris-Cl, pH 7.4, 100 mM NaCl, and 1 mM EDTA, pH 8.0) was used to resuspend the viral pellets for infection as well as to isolate viral RNA using TRizol reagent.

Transduction and Cell Processing

Virus particles released in the supernatants were harvested 72 hours post transfection, cleared of any cellular debris, and used to infect HeLa T4 cells, which were plated a day prior to infection at a density of $0.4\times10^6$ per 60-millimeter plate in the presence of DEAE-dextran sulfate, as described previously (Browning et al., 2001). Forty-eight hours post infection, the transduced HeLa T4 cells were either selected with media containing hygromycin B or trypsinized for luciferase assays, or prepared for analysis by flow cytometry, depending upon the marker gene used. For flow cytometry, cells were washed with PBS and analyzed on a Becton Dickinson Fluorescent Activating Cell Sorting (FACS) using the CellQuest software. For the selection of hygromycin resistant colonies (Hygr), antibiotic resistant colonies were selected for 10-12 days with media containing hygromycin B, stained with crystal violet dye, and counted, as described previously (Browning et al. 2001).

To harvest HEK 293T cells transiently transfected with the three-plasmid for virus production, the cells were collected 48 hours after transfection for further analysis. To eliminate any dead cells, the supernatants were removed from the 6 well plate, and each well was treated with a mixture of 1 ml of DMEM media and 1 ml of ice-cold 1×PBS. The cells were gently detached from the plate surface by pipetting on ice, followed by a wash with 5 ml of cold 1×PBS. Subsequently, the cells were resuspended in 1 ml of cold 1×PBS. The cell pellets, obtained from a single 6-well plate, were divided into separate fractions for protein (luciferase assay), DNA, and RNA extractions.

Specifically, 100 μl (1/10th) of the cell suspension was used for the dual luciferase assay (Promega, Madison, WI). For cell lysis, the cells were subjected to at least three freeze/thaw cycles, alternating between dry ice and a 37° C. water bath, using 1× Passive Lysis Buffer. After thermal lysis, the cell lysates were centrifuged at 13,000 rpm for 5 minutes at 4° C. in a benchtop microcentrifuge (Eppendorf Centrifuge 5424R) to remove cellular debris. The clear supernatants were then transferred to fresh tubes for the luciferase assay, following the manufacturer's instructions. To determine protein content, the cell lysates were assessed using the BioRad protein quantification dye kit with bovine serum albumin (BSA) as standards. RNA and DNA were isolated from the remaining cells using TRizol reagent, as per manufacturer's directions.

Reporter Gene Assays

Single or dual luciferase assays were performed as described below herein.

(i) Firefly Luciferase Assay

To quantify the activity of firefly luciferase in cell lysates, we employed the Luciferase Assay Reagent II (LAR II). For each 2 μl of lysate, we added 25 μl of LAR II substrate, thoroughly mixed the components, and then measured luciferase activity using the Glomax 20/20 Luminometer also from Promega. The luminometer settings included a 5-second delay and a 20-second integration time. The obtained values were normalized to the quantity of protein used, and transfection efficiency was expressed as the ratio of luciferase activity to μg of protein.

(ii) Dual Luciferase Assay

The dual luciferase reporter assay from Promega was conducted according to the manufacturer's instructions. To maintain a consistent ratio between cell lysates and substrate for both Firefly and *Renilla* luciferase activities, we initially combined 4 μl of cell lysate with 25 μl of LAR II substrate. Subsequently, readings were taken using the Promega Dual-Glo program, which had preset parameters of a 0-second delay and a 10-second integration time on a luminometer. To determine *Renilla* luciferase activity, 25 μl of Stop & Glo Reagent from Promega was added. Both readings were recorded in relative light units and normalized to the protein quantities obtained from the Bradford protein quantification assay.

Cellular RNA Isolation

Total cellular RNA extraction was performed by using TRizol reagent from Invitrogen. After resuspending the cell pellets in TRizol reagent, the samples were incubated at room temperature for 5-10 minutes to achieve complete lysis. Subsequently, 100 μl of chloroform was added for RNA extraction for each ml of TRizol used. Following thorough mixing, centrifugation was done to separate the organic phase from the aqueous phase, which contained the RNA. The top aqueous layer, rich in RNA, was transferred to clean tubes containing 600 μl of isopropanol. RNA was allowed to precipitate at room temperature for 10 minutes and then pelleted by centrifugation at 13,000 rpm for 20 minutes at room temperature. The RNA pellets were washed with 70% ice-cold ethanol and the resulting RNA pellets were left to air dry at room temperature for 30-60 minutes before being reconstituted in RNase-free water. To ensure complete resuspension, the RNA pellets were briefly vortexed and incubated at 55° C. for 10 minutes before being stored at −80° C. for subsequent use.

Animal Experiments and Ethical Approval

BALB/c and C57BL/6 mice were procured from the breeding colony housed at the animal facility in UAE University. All animals receiving intraperitoneal (ip) injection directly, intravenous (iv) tail vain injection, or stereotaxic injection in SNC of brain were older than two months of age at the time of injection. The proposed study and all procedures were approved by the Animal Ethics and Care Committee at the United Arab Emirates University.

IVIS Imaging on Live Animals and Organs

In this study, the In Vivo Imaging System (IVIS) was used for both live animals and animal organs to monitor firefly luciferase activity following gene delivery by WT and SIN viral vector injected intraperitoneally, intravenously or through stereotaxic injections. For live animal experiments, D-Luciferin (either the potassium or sodium salt) was thawed at room temperature and dissolved in 1×PBS (without calcium or magnesium) to achieve a final concentration of 15 mg/mL. A 0.22 μm filter was pre-wet with sterile $H_2O$ and subsequently used to filter sterilize the D-Luciferin solution. Mice were then intraperitoneally injected with D-Luciferin at a final concentration of 15 mg/kg prior to imaging. Following the injection, a waiting period of 10-30 minutes was observed to allow for the luciferase signal to reach its maximum plateau before imaging.

For investigations involving animal organs, a two-tiered luciferin solution was prepared in 1×PBS and filter sterilized using a 0.2 μm filter: one solution at 15 mg/ml for in vivo injection prior to euthanasia and another at 300 μg/ml for ex vivo tissue imaging. Just prior to euthanasia, the mice received an intraperitoneal injection of D-luciferin from the 15 mg/mL stock at a dose of 150 mg/kg. Immediately after harvesting, the individual tissues of interest were placed on a 10 cm petri plate. These tissues were then covered with the 300 μg/mL luciferin solution, and 10-20 μl of the 15 mg/mL luciferin stock was directly injected into each organ. A 5-minute waiting period was observed before initiating imaging. The initial imaging of tissues was conducted at 1 minute, and image times and binning settings were adjusted as needed. Subsequently, the tissues were frozen in TRizol for further DNA and gene expression analysis. This comprehensive IVIS protocol allowed for the effective assessment of firefly luciferase activity in both live animals and their respective organs, providing valuable data about viral vector transgene delivery.

Stereotaxis Injections in Adult Mice Brain

BALB/c or C57 black 6 (C57/B6) mice (n=6) were anesthetized with isofluorane and secured in a stereotaxic frame (David Kopf Instruments, Tujunga, CA). Small holes, matching the size of the injection needle were drilled into the skull, and injections were injected into the striatum (coordinates from bregma: anterior-posterior, +0.5 mm; medial-lateral, −2.2 mm; dorsal ventral, −3.4 mm) with 5 μl of WT or SIN vector per brain region. The injection syringe (Hamilton, Reno, NV) injected viral vector at a constant steady volume of 0.5 μl/min using a syringe automatic pump (World Precision Instruments, USA). Moreover, the needle was left in the same place for 2 min after each injection to reduce the flow of viral vector solution in opposite direction after raising the needle. For each mice strain, the coordinates were set according to the SNC part of brain. The injected mice were put in individual cages and monitored on a routine basis.

Example 2: The Three Plasmid Trans-Complementation Assay

The three plasmid trans-complementation assay contains the packaging and Env-expression plasmids, JA10 and MD.G, respectively and a transfer vector DA024 that produces the packageable RNA expressing the hygromycin resistance gene cassette as the marker/reporter transgene. These three vectors are transfected together in HEK 293T producer cells to make infectious viral particles for marker/reporter gene delivery into target cells.

The three plasmids, JA10, MD.G and DA024 are co-transfected into the producer cells HEK 293T cells, resulting in the generation of viral particles containing the packaged transfer vector RNA encoding hygromycin as a transgene (FIG. 1B) that is used to deliver the gene of interest (GOI) or transgene into the target cells, typically, HeLa T4. Among these three plasmids, only the transfer vector RNA contains the packaging signal due to which this RNA selectively gets packaged into the viral particles transcribed by the Gag/Pro/Pol expression plasmids (FIG. 1B). The so produced virus particles generated are defective for replication and limited to only a "single round" as the transduced cells will only have the transgene-expressing RNA and no genetic material to make the structural proteins is limited to a single round with no further chance of reinfection (FIG. 1C).

JA10, MD.G or MD2.G, and DA024 plasmids were systematically modified to create recombinant retroviral vector according to the present invention with the potential to deliver the transgene safely and efficiently into human cells, but in the process result in their own self-inactivation by removal of the packaging signal.

Example 3: Preparation of Recombinant Retroviral Vector

Modification of DA024 Classical Transfer Vector

Figure 2:
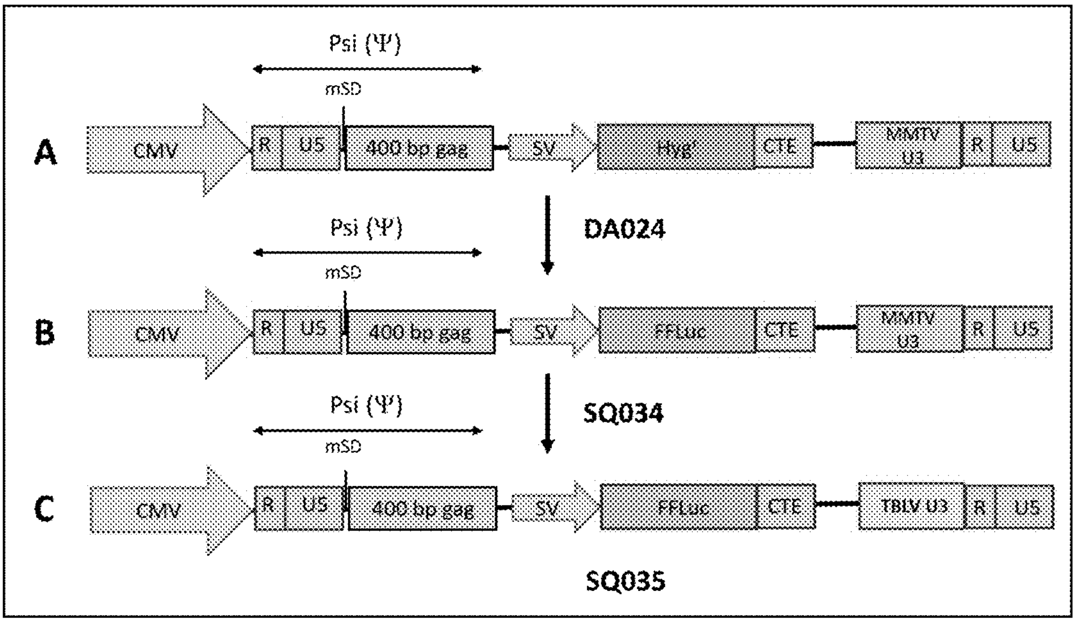
FIG. 2: Modifications introduced into DA024 to create the MMTV- and TBLV-based vectors, wherein the abbreviations are as follows: CMV, cytomegalovirus promoter; R, repeat sequences of MMTV LTR; U5, unique 5' sequences of MMTV LTR; U3, unique 3' sequences of TBLV LTR; Psi (Ψ), the MMTV RNA packaging signal; mSD, major splice donor; SV, simian virus 40 promoter; FFLuc, Firefly luciferase gene; CTE, constitutive transport element from MPMV. Psi (Ψ), RNA packaging signal

The classical MMTV transfer vector, DA024, containing the hygromycin resistance gene as a transgene for delivery and selection post transduction in target cells was modified to generate the SIN vectors. The hydromycin resistance gene of DA024 was replaced by the firefly luciferase (Luc) gene, creating SQ034. The Luc gene allowed for a more robust quantitative analysis of transduction efficiency with reduced time as compared to the time taken for transduction computation using colony forming unit (CFU) quantification. SQ034 was also modified to create SQ035 in which the 3' LTR of MMTV was replaced with that from TBLV, the lymphotropic strain of MMTV which is highly active in T lymphocytes due to the deletion of NREs within the LTV and the presence of an enhancer that improves gene expression in lymphocytes. The two modified vectors, SQ034 and SQ035 served as basis for creating the MMTV- or TBLV-based SIN vectors. FIG. 2 shows the modifications introduced into DA024 to create SQ034 and SQ035.

Preparation of Split Intron-Based SIN Transfer Vectors

The idea behind the design of split intron-based SIN transfer vectors according to the present invention is to mutate the original suboptimal major splice of the virus (mSD), rendering it defective (FIG. 3A). Simultaneously, efficient eukaryotic splice acceptors and donors (eSA and eSD) are introduced into the vector in a strategic manner so that upon reverse transcription and integration, the packaging signal of the transfer vector is deleted since now it is surrounded by the artificially cloned splice sites, creating an intron (FIG. 3B). Accomplishing this requires cloning the eSA downstream of the packaging signal while the eSD is cloned in the U3 region of the 3' LTR. Thus, upon reverse transcription and integration in the transduced cells, the U3 region is copied to the 5' end of the vector, upstream of the packaging signal, creating the intron that now houses the packaging signal. This strategy prevents cleavage of the packaging signal during virus production, which takes place in the HEK 293T cells, allowing packaging of the transfer vector RNA containing the transgene or therapeutic gene. When the vector RNA is expressed in the transduced cells, the splice sites become active, removing the packaging signal from the RNA, rendering it defective for further steps in virus replication, such as RNA encapsidation and virion assembly (FIG. 3B).

To create these vectors, a step-by-step approach was used using both the SQ034 and SQ035 backbones to provide versatility to the vectors. The mSD mutation was carefully designed so that it did not disrupt the structure of the MMTV packaging signal, psi(Ψ). The MMTV psiforms a bifurcated stem loop 4 (SL4) with one of the stem loops important for gRNA dimerization due to the presence of a palindrome (Pal II) in the apical loop (Aktar et al., 2014), while the other stem loop important for recognition of the gRNA by the retroviral Gag proteins due the presence of a single-stranded purine-rich loop (ssPurines as shown in FIG. 4) (Aktar et al. 2014; Mustafa et al. 2018; Chameettachal et al. 2018 & 2021; Prabhu et al. 2024). As can be seen, the major splice donor of MMTV is located right next to ssPurines; therefore, it is expected that mutations in and around the mSD affected the structure of the psi. To ensure that the new mutations in the mSD were functional for RNA packaging, two different mutations, mSD1 and mSD2, were introduced in the major splice donor (FIG. 4). These mutations were designed such that they replaced the conserved splice donor consensus sequences while maintaining the secondary RNA structure of the packageable transfer RNA.

A number of mutation combinations in the region in and around the mSD were tested, followed by analyzing the effect of these changes on the RNA secondary structure of the MMTV psias evaluated in-silico using Mfold (Zuker et al., 2003). If the mutation affected the RNA secondary structure, it was discarded and another one tested. Two mutations, mSD1 and mSD2, were finally shortlisted that did not affect the structure of psior the SL4 loop (FIG. 5). They maintained the overall structure of the 5' end of the MMTV genome shown at the bottom of the figure and maintained integrity of the SL4 loop so that both the ssPurine and the Pal II loops were maintained (FIG. 5).

The WT vectors SQ034 and SQ035 were used as basis for the construction of the modified vectors. First, a synthetic but efficient splice donor (eSD) derived from the SV40 small-T antigen gene was inserted between the R region and U5' or at the end of U3 of the 3' LTR, creating intermediate SIN vectors, SQ064/SQ065 and SQ066/SQ067, respectively (FIG. 6). Similarly, G-blocks with the two mSD mutations, mSD1 & mSD2, were cloned into SQ034 and SQ035 along with the consensus splice acceptor (eSA) branchpoint sequences downstream of the 400 bp of gag gene using the same G-blocks, creating intermediate SIN vectors, SQ068/SQ069 and SQ070/SQ071, respectively (FIG. 6). Finally, fragments containing the mSD mutations along with the insertion of eSA were cloned into SQ064, SQ065, SQ066 and SQ067 backbones to create the final SIN vectors named, SQ072, SQ073, SQ074 and SQ075 for mSD1 with eSA insertion, and SQ076, SQ077, SQ078, SQ079 for mSD2 with eSA insertion (FIG. 6). The even numbered clones had the MMTV LTR at the 3' end, while the odd numbered vectors had the TBLV LTR at the 3' end.

The final SIN vectors were made with either the MMTV or TBLV LTRs at the end to introduce more versatility to these vectors in terms of their tissue specificity and variable hormone inducibility in different types of cells.

Results: Evaluation of the Modified Intermediate Split Intron SIN Vectors with eSD Insertions First, the intermediate SIN vectors with eSD in the 3' LTR at the two different locations, within R but before U5 region, SQ064/SQ065, and at the end of U3, SQ066/SQ067, were tested in the three plasmid trans-complementation assay for functionality in HEK 293T cells. All vectors were transfected within 1.5-fold of each other (FIG. 7A). The normalized firefly luciferase expression of these vectors was compared with wild type vectors, SQ034 and SQ035. As can be seen, all four vectors expressed the firefly luciferase at similar levels; i.e., ~50-60% of the levels expressed by the wild type vectors, irrespective to where the eSD was inserted within the 3' LTR (FIG. 7B). This result revealed that manipulation of sequences during eSD cloning did not completely disrupt reporter gene expression in producer cells, but it was half of that observed for the wild type vectors. This reduction suggests that the observed difference can be attributed to some negative effect of the eSD insertion near the polyA signal due to the cloning.

Next, the viral supernatants harvested from the intermediate SIN- and WT-transfer vectors transfected producer cells were used to infect HeLa T4 target cells. The transduced cells were processed for firefly luciferase expression 48 hours post infection to analyze the gene delivery ability of modified SIN transfer vectors compared to the WT. This analysis revealed that the first set of the intermediate SIN vectors, SQ064 and SQ065, where the eSD was cloned between the R-U5, led to highly reduced levels (10-20%) of luciferase gene transduction compared to their respective wild type vectors (FIG. 7C). Considering that these vectors were able to express quite well at the transfection levels, these results suggest that the mutation introduced affected either reverse transcription and/or integration of the transfer vectors constructed. However, the second set of intermediate SIN vectors, SQ066 and SQ067, containing the eSD at the end of U3 did not show any such defect with transduction efficiencies comparable to their respective wild type (FIG. 7C).

Results: Evaluation of the Intermediate Split Intron SIN Vectors with Mutations of mSD and eSA Insertions The intermediate vectors, SQ068-SQ071, containing mutations of the retroviral mSD which were inserted after extensive in-silico secondary structure analysis of the mutated MMTV packaging signal RNA along with eSA sequences were tested in the three plasmid trans-complementation assay (FIG. 8). Test of these vectors in the HEK 293T cells upon transfection revealed that all of them expressed the firefly luciferase transgene better than their relative wild type controls, SQ034 or SQ035, by 1.5- to 2-folds, when normalized to the transfection efficiency (FIGS. 8A and 8B). Among the mSD mutants, the vectors containing the mSD2 mutation showed better expression than those with mSD1 mutation (FIG. 8B). Furthermore, the TBLV LTR containing vectors consistently expressed the transgene better than the MMTV LTR-based vectors.

Transduction of HeLa T4 target cells revealed that the MMTV LTR-based vectors, SQ068 and SQ070, could transduce the FFLuc transgene nearly as efficiently as the wild type vector SQ034, while the TBLV LTR-based vectors, SQ069 and SQ071, showed an improved transduction efficiency when compared to their respective wild type vector, SQ035 (FIG. 8C). However, the transduction efficiency of the MMTV LTR-based vectors was consistently better than those of the TBLV LTR-based vectors. These mutations were combined in the final self-splicing SIN vectors to develop the final set of SIN vectors.

Results: Evaluation of the Final Split Intron SIN Transfer Vectors

After confirming the functional preservation of transgene expression from split intron SIN transfer vectors with each modification (mutation of mSD, insertion of eSA, and cloning of eSD in the 3' LTR), the final SIN vectors and tested for functionality in the three plasmid trans-complementation assay. The final vectors, SQ072, SQ073, SQ074, SQ075 contained mSD1, while vectors SQ076, SQ077, SQ078, SQ079 contained mSD2 (FIG. 9).

The transfection efficiency was within 1.5-folds for all vectors (FIG. 9A). The normalized firefly luciferase expression in producer cells transfected with SQ074 & SQ075 (containing mSD1, eSA, eSD at the end of U3) and SQ078 and SQ079 (containing mSD2, eSA, eSD at the end of U3), was equivalent or higher than their respective WTs (SQ034 and SQ035) (FIG. 9B). However, the vectors with insertion of eSD in the R-U5 region, SQ072 and SQ073 (containing mSD1, eSA, eSD R-U5) and SQ076 and SQ077 (containing mSD2, eSA, eSD R-U5) showed strong inhibition of firefly luciferase transgene expression (FIG. 9B). This was expected since a similar inhibition (though not to the same extent) was observed earlier in the intermediate vectors, SQ064 and SQ065, containing the eSD in the same location upon transfection (FIG. 9B). This confirmed that there was no pre-mature splicing of packaging signal in producer cells and successful inactivation of mSD in 5' LTR due to introduced mutations.

The lower transgene expression of vectors SQ072, SQ073, SQ076, and SQ077 upon transfection translated into significantly reduced transgene expression from integrated split intron SIN vectors compared to their WT vectors (FIG. 9C). This could partially be associated with what was observed after the insertion of eSD in between R-U5. However, the overall reduction in transgene expression from integrated split intron SIN vectors could be a synergistic effect due to the absence of full-length genomic RNA from the MMTV or TBLV 5' LTR as a result of packaging signal deletion in these split intron SIN vectors. On the other hand, SQ074, SQ075, SQ078 and SQ079 that expressed the transgene equal or better than WT vectors showed WT or better levels of transgene expression from the transduced vectors (FIG. 9C), revealing that we were finally successful in constructing self-splicing MMTV-based SIN vectors with efficient transduction capabilities.

Example 4: Evaluation of the SIN Transfer Vectors in Mice

The non-SIN transfer vector SQ034 and the two SIN transfer vectors, SQ074 and SQ078 were tested for in mice for their ability to deliver the firefly luciferase transgene to different mice organs. High titer virus was prepared from each test vector together with a negative control plasmid, pCDNA3, by scaling up the three-plasmid trans-complementation assay, using JA10 and MD.G. The virions were harvested from transfected cultures and concentrated via ultracentrifugation, followed by virus titration on HeLa cells using luciferase assays. The viral titers thus obtained were in the range of $10^6$ TU/ml (transduction units/mL) viral vector suspension.

Dose-Dependent In Vivo Gene Delivery Using MMTV-Based Non-SIN Vector

The transduction capability of the non-SIN vector, SQ034, into BALB/c mice. Different volumes of the virus stock prepared using either pCDNA3 or SQ034 via tail-vein IV injections, three mice per dose. The reporter gene expression from infected animals was evaluated using IVIS imaging of live animals at 72 hours post injection, while organs were harvested from the injected mice after sacrificing them one month later. Imaging of live mice was conducted by injecting them intraperitoneally with D-luciferin substrate 30 minutes prior to imaging. Live animals were then monitored under the IVIS instrument for luciferase enzymatic activity expressed from cells successfully infected with the viral vectors that had undergone proper reverse transcription and integration of the viral vector into the mouse genome. Thus, presence of luciferase activity suggested successful delivery of the firefly luciferase marker gene into the animal via the viral vector used. The animals were re-imaged after another week and then allowed to live for another three weeks after which they were euthanized and their organs collected and analyzed via IVIS for luciferase activity.

Results:

The results of the live imaging as well as imaging of the harvested organs one-month post injection are shown in FIG. 10. Virions prepared from control empty vector, pCDNA3, served as the negative control. No luciferase expression was observed in mice injected with virions prepared from pCDNA3 after administration of D-luciferin substrate intraperitoneally. Thus, the negative control was confirmed to be deficient of any non-specific luciferase expression under the IVIS reading conditions used (FIG. 10—Upper right panel). Using the same settings, the mice injected with the test virions were imaged. An increase in luciferase expression could be observed in mice injected with increasing volumes of virions prepared from SQ034 (50 μl, 100 μl, & 150 μl of $10^6$ TU/ml concentrated viral particles) upon intraperitoneal administration of D-luciferin substrate. The increase of luciferase expression in a dose-dependent manner confirmed the specific delivery and functional enzymatic activity of luciferase transgene delivered through MMTV-based non-SIN vector into live animals (FIG. 10—Upper left panel). However, within each group, variability of expression of the transgene was observed which probably reflects differences in the amount of virus actually delivered via the tail vein injections which are a bit tricky to master.

The injected mice were maintained for up to 1 month to assess long-term expression of the firefly luciferase transgene in different mice organs. Mice were injected with D-luciferin substrate 30 minutes prior to euthanasia, and the various organs were harvested for imaging via IVIS. Once again, the organs from the negative control mice were used for setting up IVIS imaging settings to establish lack of any non-specific luciferase enzymatic activity. Imaging of organs from mice injected with virions prepared from SQ034 revealed the specific delivery and expression of luciferase activity in the liver, stomach, lungs and kidneys, predominantly (FIG. 10—Lower left panel). This viral vector was found to be specifically targeting these organs as increasing the virus dose from 50 μl to 150 μl did not contribute towards wider organ targeting or increased biodistribution of luciferase expression.

Comparison of MMTV-Based WT and SIN Vectors for In Vivo Gene Delivery

The MMTV SIN vectors (SQ074 and SQ078) were tested for in vivo delivery and functionality of the transgene in the BALB/c mice using tail vein injections. The firefly reporter gene expression from infected animals was evaluated using live animal IVIS imaging. Organs were harvested after sacrificing the injected mice to confirm long-term transgene expression from integrated viral vectors. Live animal imaging was performed 72 hrs post-injection. Mice injected with virions prepared from MMTV-based WT and SIN viral vectors were imaged after intraperitoneal injection of D-luciferin substrate 30 mins before imaging. Transgene expression of luciferase and enzymatic activity in mice injected with MMTV WT (S0Q34) and SIN viral vectors (S0Q74 and S0Q78) were compared, including transgene activity expressed from injected viral vectors through IVIS imaging.

Figure 11:
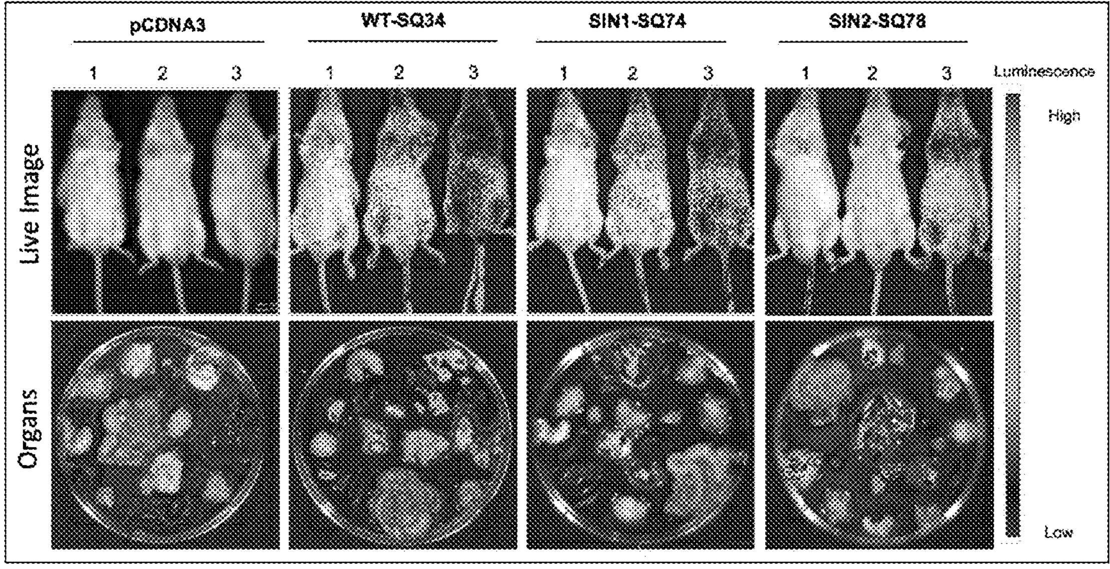

Results:

Equivalent luciferase expression was observed in mice injected with the same concentration (100 μl of $10^6$ TU/ml concentrated viral particles) of WT (SQ034) and SIN MMTV (S0Q74 and S0Q78) viral vectors carrying luciferase transgene upon intraperitoneal administration of D-luciferin substrate (FIG. 11—Upper panel). Measurable luciferase expression through WT (SQ034) and SIN vectors (S0Q74 and S0Q78) confirmed successful transgene delivery in live animals.

These injected mice were maintained for up to 1 month to observe long-term expression of luciferase in different mice organs from integrated vectors. Mice were injected 30 minutes before sacrifice with D-luciferin substrate and the organs were harvested from WT and SIN virion infected mice for imaging of luciferase as before. IVIS imaging confirmed a lack of any non-specific luciferase enzymatic activity in the organs of the negative control set of mice (FIG. 11—Lower right panel). Imaging of organs from mice injected with virions prepared from WT and SIN viral vectors confirmed similar biodistribution and enzymatic activity of luciferase transgene in the liver, stomach, lungs, and kidneys, predominantly as previously observed (FIG. 11—Lower panel). Some organs, such as heart, were completely deficient of any luciferase expression/activity. These results show that the SIN vectors were efficient in gene delivery not only in human cells, but also in mice.

Luciferase Transgene Delivery to Mice Brain Using MMTV-Based WT and SIN Vectors

MMTV-based WT (SQ34) and SIN vectors (SQ74 and SQ78) were tested for luciferase gene delivery and enzymatic activity in adult C57BL/6 mice brain using direct injection. The same viral stocks were used for these injections (5 μl of $10^6$ TU/ml concentrated viral particles). These concentrated viral particles carrying luciferase as transgene were injected into the substantia nigra pars *compacta* (SNC) of mice brain through stereotaxic injection (FIG. 12). The injection coordinates were set according to SNC location, allowing vectors to transduce cells on the SNC side of the brain. After mice recovered from surgery post injections, D-luciferin was injected in mice for imaging of firefly luciferase expression using IVIS imaging.

Results

Luciferase transgene expression was observed in live animals of WT and SIN injected mice, suggesting successful gene delivery through our WT and SIN viral vectors (FIG. 12—Upper right panel). To confirm these findings, mice brains were harvested after sacrificing the injected mice and reimaged under IVIS. Direct brain imaging confirmed the positive nature of the luciferase expression observed upon live animal imaging (FIG. 12—Lower right panel). The level of expression from the SIN vectors appeared greater than WT virions. This could reflect potential differences in the amount of virus delivered during the brain injection which can be quite tricky. No non-specific luciferase expression was observed in SNC portion of mice brains injected with viral vectors carrying no luciferase transgene (pCDNA3) after administration of D-luciferin substrate intraperitoneally. Therefore, negative control was confirmed to be deficient of any non-specific luciferase expression.

These data reveal that the MMTV-based WT and the SIN vectors were functional for transgene delivery and expression into human cells and mice. Among the mice, we were successful in delivering the transgene to two different mice strains, BALB/c and C57BL/6. Transgene expression could be observed for at least one month after injection. The transgene could be delivered to the liver, stomach, lungs, and kidneys of the mice using both IV and IP injections, though the IV injections were more efficient in transgene delivery. Direct injection of WT and SIN virions into the brain revealed that the transgene could be delivered to the SNC brain region and expressed successfully.

Example 5: Hormone-Inducibility of the Wild Type MMTV- and TBLV-Based Transfer Vectors (SQ034) and (SQ035)

As shown in FIG. 13, upon infection of HEK293T cells with virions produced from SQ34, the MMTV LTR-based vector, expression of the firefly transgene was enhanced by ~1.25-1.5 folds upon the addition of dexamethasone (Dex), a glucocorticoid hormone. Compared to that, expression of the firefly transgene from virions produced from the TBLV-based vector, SQ35, was increased by ~5-folds in the presence of Dex. This reveals that both LTRs are hormone responsive, but MMTV LTR is less so than the TBLV LTR.

While both LTRs contain the hormone responsive element, HRE, this difference could be attributed to the lack of the negative regulatory element (NRE) in the TBLV LTR, resulting in enhanced hormone responsiveness of the TBLV-based vector. Furthermore, the overall hormone responsiveness was less in these cells than what is observed in other cell types, such as the human Jurkat cells or the rat XC cells. This could be attributed to differences in cell-type specific factors, especially the levels of the hormone receptors.

For gene therapy, this result suggests that depending upon the cell type to be treated and whether they respond to hormones, one could choose between these two types of vectors according to the level of transgene expression desired. Thus, in hormone responsive cells, one could choose vectors based on the TBLV LTR for inducible and high-level transgene expression, while in cells non-responsive to hormones, either of the two vectors should work effectively.

Example Embodiments

Certain embodiments of the present disclosure can be described in view of the following examples:

Example 1. A recombinant retroviral vector, which is a Split-Intron Self-Inactivating (SIN) vector, comprising:
- a. A viral major splice donor (mSD) comprising a mutation in each of the positions corresponding to positions 5, 6, 15, and 16 of SEQ ID NO: 1, and optionally in the positions corresponding to positions 4, 17, and 18 of SEQ ID NO: 1;
- b. A mouse mammary tumor vector long terminal repeat (MMTV-LTR) or a Type B leukemogenic virus long terminal repeat (TBLV-LTR);
- c. A eukaryotic splice acceptor (eSA); and
- d. A eukaryotic splice donor (eSD).

Example 2. The recombinant retroviral vector according to example 1, wherein the mSD has a sequence corresponding to SEQ ID NO: 2 or SEQ ID NO: 3, preferably SEQ ID NO: 3.

Example 3. The recombinant retroviral vector according to any one of the preceding examples, wherein the eukaryotic splice acceptor (eSA) has at least 90% sequence identity with SEQ ID NO: 4, such as at least 95%, such as at least 97%, such as at least 99% sequence identity with SEQ ID NO: 4.

Example 4. The recombinant retroviral vector according to any one of the preceding examples, the eukaryotic splice donor (eSD) corresponding to positions 20-35 of SEQ ID NO: 5, and which has at least 90% sequence identity with positions 20-35 of SEQ ID NO: 5, such as at least 95%, such as at least 97%, such as at least 99% sequence identity with positions 20-35 of SEQ ID NO: 5.

Example 5. The recombinant retroviral vector according to any one of the preceding examples, wherein the MMTV-LTR has at least 90% sequence identity with SEQ ID NO: 6, such as at least 95%, such as at least 97%, such as at least 99% sequence identity with SEQ ID NO: 6; or the TBLV-LTR has at least 90% sequence identity with SEQ ID NO: 7, such as at least 95%, such as at least 97%, such as at least 99% sequence identity with SEQ ID NO: 7.

Example 6. The recombinant retroviral vector according to any one of the preceding examples, comprising an exogenous gene of interest.

Example 7. The recombinant retroviral vector according to example 6, comprising a promoter operably linked to the exogenous gene of interest.

Example 8. The recombinant retroviral vector according to any one of the preceding examples, comprising a constitutive transport element (CTE), such as a Mason-Pfizer monkey virus (MPMV) CTE, such as a CTE having at least 90% sequence identity with SEQ ID NO: 8.

Example 9. The recombinant retroviral vector according to any one of the preceding examples, comprising a promoter upstream of the mSD, preferably a cytomegalovirus (CMV) promoter.

Example 10. The recombinant retroviral vector according to any one of the preceding examples, comprising, in order from 5' to 3': the mSD, the eSA, and the MMTV-LTR comprising the eSD or the TBLV-LTR comprising the eSD.

Example 11. The recombinant retroviral vector according to any one of the preceding examples, comprising, in order from 5' to 3': a promoter upstream of the mSD, the mSD, the eSA, an exogenous gene of interest, a CTE, and the MMTV-LTR comprising the eSD or the TBLV-LTR comprising the eSD.

Example 12. An expression plasmid comprising the recombinant viral vector according to any one of the preceding examples.

Example 13. A viral particle comprising the recombinant viral vector according to any one of examples 1 to 11.

Example 14. The viral particle according to example 13, wherein the viral particle is T-cell tropic.

Example 15. A producer cell comprising the recombinant viral vector according to any one of examples 1 to 11, the viral particle according to any one of examples 13-14, a packaging construct and/or an envelope expression construct.

Example 16. A cell-line comprising the viral particle according to any one of examples 13-14.

Example 17. The cell-line according to example 16, comprising lymphocytes, such as T cells, such as CD4+ T cells; or hematopoietic cells, such as hematopoietic stem cells (HSCs).

Example 18. A composition comprising the recombinant retroviral vector according to any one of examples 1-11, the expression plasmid according to example 12, the viral particle according to any one of examples 13-14, the producer cell according to example 15, and/or the cell-line according to any one of examples 16-17.

Example 19. A pharmaceutical composition comprising the viral particle according to any one of examples 13-14, or the cell-line according to any one of examples 16-17.

Example 20. A kit comprising:
- a. The recombinant retroviral vector according to any one of examples 1-11 and/or the expression plasmid according to example 12; and
- b. Instructions for use.

Example 21. The recombinant vector according to any one of examples 1-11, the expression plasmid according to example 12, the viral particle according to any one of examples 13-14, the cell-line according to any one of examples 16-17, the composition according to example 18, the pharmaceutical composition according to example 19, or the kit according to example 20, for use in gene therapy, such as ex vivo gene therapy; cancer immunotherapy, such as breast cancer immunotherapy; treatment of genetic diseases; treatment of immune disorders, such as severe combined immunodeficiency (SCID); treatment of lung disorders and/or treatment of infectious diseases.

Example 22. A method of producing a viral particle, comprising the steps:

a. Introducing the recombinant viral vector according to any one of examples 1-11 or the expression plasmid according to example 12 to a cell, optionally wherein the cell is the producer cell according to example 15;

b. Extracting one or more viral particle(s) according to any one of examples 13-14 from the cell of step a.

Example 23. A method of treatment, comprising the steps of:

a. Introducing the recombinant viral vector according to any one of examples 1-11 or the expression plasmid according to example 12 to a cell, optionally wherein the cell is the producer cell according to example 15;

b. Extracting one or more viral particle(s) according to any one of examples 13-14 from the cell of step a;

c. Administering the viral particle(s) of step b. to a mammal in need of treatment, optionally wherein the mammal is a human.

Example 24. The method of treatment according to example 23, wherein the method of treatment comprises gene therapy.

Example 25. A method of treatment, comprising the steps of:

a. Introducing the recombinant viral vector according to any one of examples 1-11 or the expression plasmid according to example 12 to a cell, optionally wherein the cell is the producer cell according to example 15;

b. Extracting one or more viral particle(s) according to any one of examples 13-14 from the cell of step a.;

c. Introducing the viral particle(s) of step b. to one or more cells in vitro to generate a cell-line according to any one of examples 16-17;

d. Optionally performing a selection for the cell-line in step c.;

e. Administering the cell-line of step c. or d. to a mammal in need of treatment, optionally wherein the mammal is a human.

REFERENCES

Rizvi, T. A.; Panganiban, A. T. Simian immunodeficiency virus RNA is efficiently encapsidated by human immunodeficiency virus type 1 particles, J. Virol., 1993, 67, 2681-2688

Yin PH, Hu W-S; RNAs from genetically distinct retroviruses can copackage and exchange genetic information in vivo. J Viro. 1997, 71: 6237-6242

Motomura K, Chen J, Hu WS: Genetic recombination between human immunodeficiency virus type 1 (HIV-1) and HIV-2, two distinct human lentiviruses, J Virol. 2008, 82: 1923-1933

Al Shamsi I R, Al Dhaheri N S, Phillip P S, Mustafa F, Rizvi T A. Reciprocal cross-packaging of primate lentiviral (HIV-1 and SIV) RNAs by heterologous non-lentivriral MPMV protins. Virus Res. 2011 January; 155(1):352-7. Doi:10.1016/j.virusres.2010.09.018.Epub 2010 Sep. 25. PMID: 20875467

Al Dhaberi N S, Phillip P S, Ghazawi A, Ali J, Beebi E, Jaballah S A, Rizvi T A. Cross-packaging of genetically distinct mouse and primate retroviral RNAs. Retrovirology. 2009 Jul. 14; 6:66. Doi:10.1186/1742-4690-6-66. PMID: 19602292, PMCID: PMC2723071

Ali L M, Rizvi T A, Mustafa F. Cross. And Co-Packaging of Retroviral RNAs and Their Consequences. Viruses. 2016 Oct. 11; 8(10):278. Doi: 10.3390/v8100276. PMID: 27727192; PMCID:PMC5086612

Poeschla E M, Wong-Staal F, Looney D J. Efficient transduction of nondividing human cells by immunodeficiency virus lentiviral vectors. Nat Med. 1998 March; 4(3):354-7.doi:10.1038/nm0398-354 Ball, J. K., H. Diggelmann, G. A. Dekaban, G. F. Grossi, R. Semmler, P. A. Waight, and R. F. Fletcher, 1988. Alterations in the U3 region of the long terminal repeat of an infectious thymotropic type B retrovirus. J. Virol. 62:2985-2993.

Mertz, J., F. Mustafa, s. Meyers, and J. P. Dudley. Type B leukemogenic virus has a T-cell specific enhancer that binds AML-1. J. Virol. 75:2174-2184.2001. DOI: https://doi.org/10.1128/JVI.75.5.2174-2184.2001

Mustafa, F., S. Bhadra, D. Johnston, M. Lozano, and J. P. Dudley. The type B leukemogenic virus superantigen is dispensable for T-cell lymphomagenesis. *J. Virol.* 77:3866-70. 2003.

Sambrook J, Russell D (2001) Molecular Cloning: A Laboratory Manual, 3rd edn. Cold Spring Harbor, NY: Cold Spring Harbor Laboratory Press.

Mustafa, F., Vivet-Boudou, V., Jabeen, A., Ali, L. M., Kalloush, R. M., Marquet, R., Rizvi, T. A. The bifurcated stem loop 4 (SL4) is crucial for efficient packaging of mouse mammary tumor virus (MMTV) genomic RNA. *RNA Biol.* 8:1047-1059. 2018.

Aktar, S. J., Vivet Boudou, V., Ali, L. M., Jabeen, A., Kalloush, R. M., Richter, D., Mustafa, F., Marquet, R., and Rizvi, T. A. Structural basis of genomic RNA (gRNA) dimerization and packaging determinants of mouse mammary tumor virus (MMTV). *Retrovirology* 11:96. 2014.

Chameettachal A., Pillai, V. N., Ali, L. M., Pitchai, F. N. N., Ardah, M. T., Mustafa, F., Marquet, R., Rizvi, T. A. Biochemical and functional characterization of mouse mammary tumor virus (MMTV) full-length Pr77Gag expressed in prokaryotic and eukaryotic cells. *Viruses,* 10(6):334. 2018. DOI: https://doi.org/10.3390/v10060334.

Zuker M. Mfold web server for nucleic acid folding and hybridization prediction. Nucleic Acids Res. 2003 Jul. 1; 31(13):3406-15. doi: 10.1093/nar/gka595. PMID: 12824337; PMCID: PMC169194.

Aktar, Suriya J., Valérie Vivet-Boudou, Lizna M. Ali, Ayesha Jabeen, Rawan M. Kalloush, Delphine Richer, Farah Mustafa, Roland Marquet, and Tahir A. Rizvi. 2014. "Structural Basis of Genomic RNA (gRNA) Dimerization and Packaging Determinants of Mouse Mammary Tumor Virus (MMTV)." *Retrovirology* 11 (November):96. https://doi.org/10.1186/s12977-014-0096-6.

Browning, M. T., R. D. Schmidt, K. A. Lew, and T. A. Rizvi. 2001. "Primate and Feline Lentivirus Vector RNA Packaging and Propagation by Heterologous Lentivirus Virions." *Journal of Virology* 75 (11): 5129-40. https://doi.org/10.1128/JVI.75.11.5129-5140.2001.

Chameettachal, Akhil. 2021. "Insights into the Packaging of Mouse Mammary Tumor Virus (MMTV) Genomic RNA by Identifying PR77$^{GAG}$ Binding Sites Involved during Its Selective Encapsidation." *Dissertations*, June. https://scholarworks.uaeu.ac.ae/all_dissertations/187.

Chameettachal, Akhil, Farah Mustafa, and Tahir A. Rizvi. 2023. "Understanding Retroviral Life Cycle and Its Genomic RNA Packaging." *Journal of Molecular Biology* 435 (3): 167924. https://doi.org/10.1016/j.jmb.2022.167924.

Gibbs, J. S., D. A. Regier, and R. C. Desrosiers. 1994. "Construction and in Vitro Properties of SIVmac Mutants with Deletions in 'Nonessential' Genes." *AIDS Research and Human Retroviruses* 10 (5): 607-16. https://doi.org/10.1089/aid.1994.10.607.

Graham, F. L., and A. J. van der Eb. 1973a. "A New Technique for the Assay of Infectivity of Human Adenovirus 5 DNA." *Virology* 52 (2): 456-67. https://doi.org/10.1016/0042-6822(73)90341-3.

Mustafa, Farah, Dhuha Al Amri, Farah Al Ali, Noor Al Sari, Sarah Al Suwaidi, Preethi Jayanth, Pretty S. Philips, and Tahir A. Rizvi. 2012. "Sequences within Both the 5' UTR and Gag Are Required for Optimal in Vivo Packaging and Propagation of Mouse Mammary Tumor Virus (MMTV) Genomic RNA." *PloS One* 7 (10): e47088. https://doi.org/10.1371/journal.pone.0047088.

Mustafa F, Lozano M, Dudley J P. 2000. C3H Mouse Mammary Tumor Virus Superantigen Function Requires a Splice Donor Site in the Envelope Gene. J Virol 74:

Prabhu S G, Pillai V N, Ali L M, Vivet-Boudou V, Chameettachal A, Bernacchi S, et al 2024 MMTV RNA packaging requires an extended long-range interaction for productive Gag binding to packaging signals. PLoS Biol 22(10): e3002827. https://doi.org/10.1371/journal.pbio.300282.

Puig-Saus, Cristina, Giulia Parisi, Angel Garcia-Diaz, Paige E. Krystofinski, Salemiz Sandoval, Ruixue Zhang, Ameya S. Champhekar, et al. 2019. "IND-Enabling Studies for a Clinical Trial to Genetically Program a Persistent Cancer-Targeted Immune System." *Clinical Cancer Research: An Official Journal of the American Association for Cancer Research* 25 (3): 1000-1011. https://doi.org/10.1158/1078-0432.CCR-18-0963.

Rizvi, Tahir A., Jahabar Ali, Pretty Susan Phillip, Akela Ghazawi, Preethi Jayanth, and Farah Mustafa. 2009. "Role of a Heterologous Retroviral Transport Element in the Development of Genetic Complementation Assay for Mouse Mammary Tumor Virus (MMTV) Replication." *Virology* 385 (2): 464-72. https://doi.org/10.1016/j.virol.2008.12.027.

Salmons, B., S. Moritz-Legrand, I. Garcha, and W. H. Gunzburg. 1989. "Construction and Characterization of a Packaging Cell Line for MMTV-Based Conditional Retroviral Vectors." *Biochemical and Biophysical Research Communications* 159 (3): 1191-98. https://doi.org/10.1016/0006-291x(89)92236-5.

The invention claimed is:

1. A recombinant retroviral vector, which is a Split-Intron Self-Inactivating (SIN) vector, comprising:

a. A viral major splice donor (mSD) consisting of the nucleotide sequence of SEQ ID No: 2 or SEQ ID No. 3 b. A mouse mammary tumor vector long terminal repeat (MMTV-LTR), wherein the MMTV-LTR has at least 90% sequence identity with the nucleotide sequence of SEQ ID NO: 6, or a Type B leukemogenic virus long terminal repeat (TBLV-LTR), wherein the TBLV-LTR has at least 90% sequence identity with the nucleotide sequence of SEQ ID NO: 7;

c. A eukaryotic splice acceptor (eSA), wherein the eSA has at least 90% sequence identity with the nucleotide sequence of SEQ ID NO: 4; and d. A eukaryotic splice donor (eSD), wherein the eSD has at least 90% sequence identity with the positions 20-35 of the nucleotide sequence of SEQ ID NO: 5; and e. A constitutive transport element (CTE), wherein the CTE has at least 90% sequence identity with the nucleotide sequence SEQ ID NO: 8.

2. The recombinant retroviral vector according to claim 1, wherein the eukaryotic splice acceptor (eSA) has at least 95% sequence identity with SEQ ID NO: 4.

3. The recombinant retroviral vector according to claim 1, comprising an exogenous gene of interest.

4. The recombinant retroviral vector according to claim 3, comprising a promoter operably linked to the exogenous gene of interest.

5. The recombinant retroviral vector according to claim 1, comprising a promoter upstream of the mSD.

6. The recombinant retroviral vector according to claim 1, comprising, in order from 5' to 3': the mSD, the eSA, the CTE, and the MMTV-LTR comprising the eSD or the TBLV-LTR comprising the eSD.

7. The recombinant retroviral vector according to claim 1, comprising, in order from 5' to 3': a promoter upstream of the mSD, the mSD, the eSA, an exogenous gene of interest, the CTE, and the MMTV-LTR comprising the eSD or the TBLV-LTR comprising the eSD.

8. An expression plasmid comprising the recombinant viral vector according to claim 1.

9. A viral particle comprising the recombinant viral vector according to claim 1.

10. The viral particle according to claim 9, wherein the viral particle is T-cell tropic.

* * * * *